Figure 1:
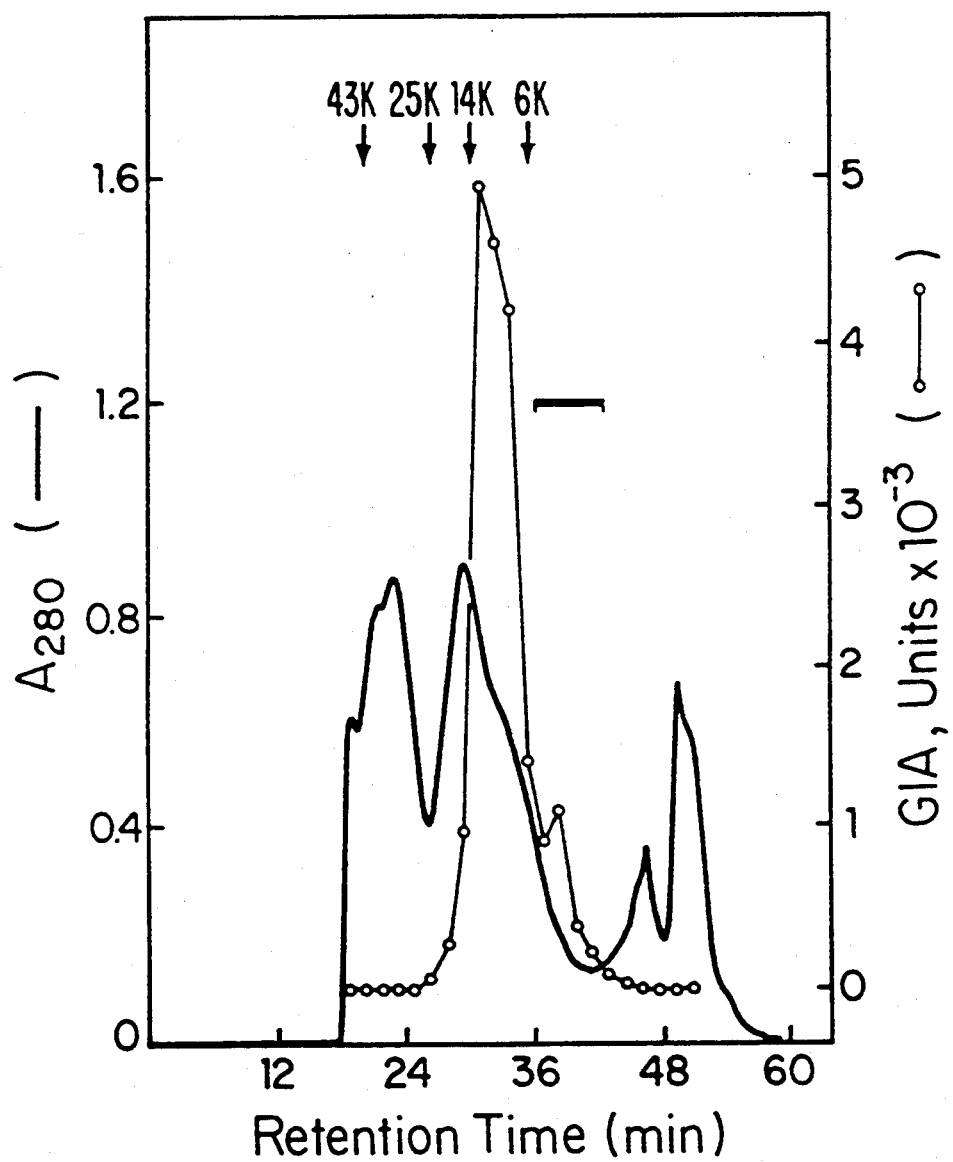

United States Patent [19]
Shoyab et al.

[11] Patent Number: 5,416,192
[45] Date of Patent: May 16, 1995

[54] EPITHELINS: NOVEL CYSTEINE-RICH GROWTH MODULATING PROTEINS

[75] Inventors: Mohammed Shoyab; Gregory D. Plowman, both of Seattle, Wash.

[73] Assignee: Bristol-Myers Squibb Company, New York, N.Y.

[21] Appl. No.: 668,648

[22] Filed: Mar. 13, 1991

Related U.S. Application Data

[63] Continuation-in-part of Ser. No. 504,508, Apr. 3, 1990, abandoned.

[51] Int. Cl.$^6$ .......................................... C07K 14/475
[52] U.S. Cl. ................................. 530/324; 435/69.1; 530/399
[58] Field of Search ...................... 530/324, 350, 399

[56] References Cited
PUBLICATIONS

Shoyab et al., "Structure & Function of Human Amphiregulia . . . ", Science, 243:1074–1076, Feb. 1989.
Mohammed Shoyab et al., (1990), "Epithelins 1 and 2: Isolation and characterization of two cysteine-rich growth-modulating proteins", *Proc. Natl. Acad. Sci. USA*, 87:7912–7916.
Andrew Bateman et al., (1990), "Granulins, a novel class of peptides from leukocytes", *Biochemical and Biophysical Research Communications*, 173:1161–1168.

Primary Examiner—Garnette D. Draper
Assistant Examiner—L. Spector
Attorney, Agent, or Firm—Pennie & Edmonds; S. Leslie Misrock

[57] ABSTRACT

A novel family of growth regulatory proteins termed "epithelins" are described. The epithelins comprise several distinct members sharing significant structural homology. Two members of the epithelin family, epithelin 1 and epithelin 2, have been purified from natural sources. In addition, cDNA and PCR clones encoding mature and precursor epithelins from various chordate sources have been obtained and sequenced, including the complete human, mouse and rat epithelin precursors. The recombinant expression of rat epithelin precursor and mature forms is described. Purified epithelin 1 is a bifunctional growth regulator, capable of stimulating the growth of some cell types while inhibiting the growth of others. Purified epithelin 2 is functionally similar to epithelin 1 with respect to growth inhibitory bioactivity. In contrast, however, epithelin 2 is apparently not capable of eliciting the growth stimulatory activity characteristic of epithelin 1 and, in fact, antagonizes this epithelin 1 activity.

3 Claims, 31 Drawing Sheets

Figure 7A
Figure 7B
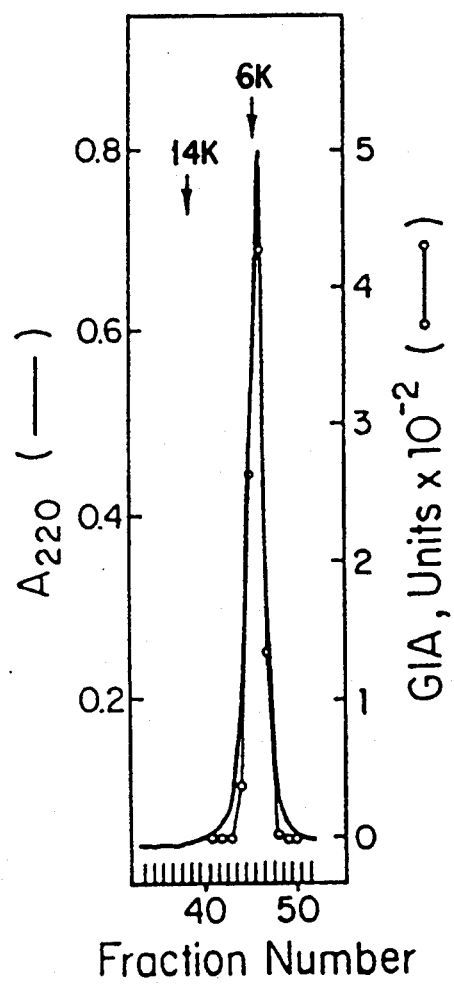
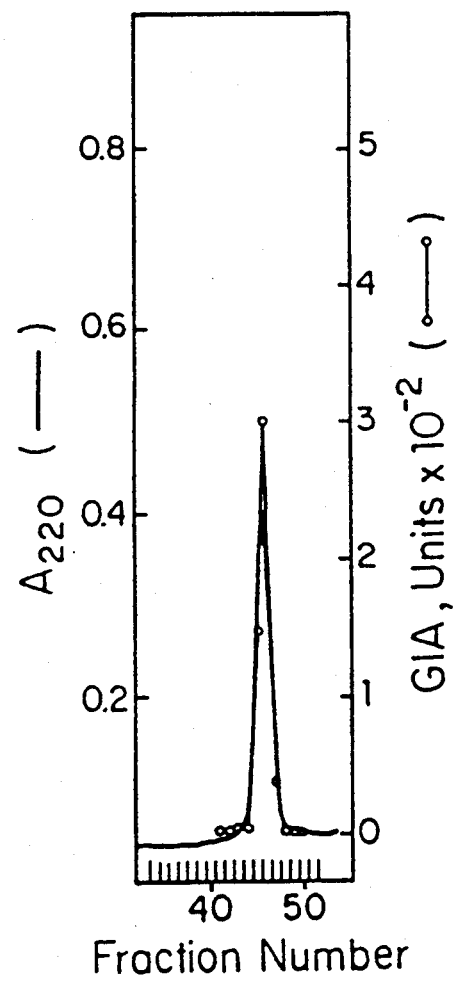

Figure 20A

```
Human   ..T....V..T.G.....R................P...S....R....K..TTL..H.G .P     60
  Rat   MWILVSWLALVARLVAGTQCPDGQFCPVACCLDQGGANYSCCNPLLDTWPIITSRRLD GS        60
Mouse   ..V.M....FA.G.............................R...HH.. ..                60

Human   ..VDA..SA.H..IF............P.A.A.G..H..............R..F. RSGNNS     120
  Rat   CQIRDHCPDGYSCLLTVSGTSSCCPFSEGVSCDDGQHCCPRGFHCSADGKSCSQ -ISDSL        119
Mouse   ..THG...A.................K....G..Y....Q...........F. -M..NP        119

Human   V.. I...D.......FS...V.V.............................F.........T   180
  Rat   LGA VQCPGSQFECPDSATCCIMIDGSWGCCPMPQASCCEDRVHCCPHGASCDLVHTRCIS       179
Mouse   ... ............................V................................V. 179

Human   ........A..L..........LSS. .M....RSR...G........S.... ........T..   240
  Rat   PTGTHPLLKKFPAQRTNRAVAFPFS VVCPDAKTQCPDDSTCCELPTGKYGCCPMPNAICC       239
Mouse   .....T........K......SL... .........................................239

Human   ......................L. .ENA....L.....AHT.GD ....M..............Q   300
  Rat   SDHLHCCPQDTVCDLIQSKCIS KDY-TTDLMTKLPGYPVNE VKCDLEVSCPDGYTCCRLN      298
Mouse   ......................L. .N.-.....L........K. ....M.....E.........  298

Human   S..........Q..............T.D.QK.....Q .PH.....E.AP.H........A.     360
  Rat   TGAWGCCPFTKAVCCEDHIHCCPAGFQCHTETGTCEL GVLQVPWMKKVTASLSLPDPQIL       358
Mouse   ...........A....................K....M .I...........I.PRR.......   358

Human   .R. .....NV.....SD...Q.T..E.............S↓.........YT.VA..Q..R .S   420
  Rat   KND VPCDDFSSCPSNNTCCRLSSGDWGCCPIPEAVCCLDHQHCCPQGFKCMDEGYCQK GD       418
Mouse   .S. T.......TR..T......K.N................S.N...........T.LAQ..... ..418

Human   EI.........A.RAS.SHPR. ................G...............↓....        480
  Rat   RMVAGLEKMPVRQTTLLQHGD IGCDQHTSCPVGQTCCPSLKGSWACCQLPHAVCCEDRQH       478
Mouse   T........I.A....P..I.. .............................................478

Human   ..............S.... EVV.A..ATF.ARSPH..VKD ....E........T..R.NRQ.   540
  Rat   CCPAGYTCNVKARTCEK DAGSVQPSMDLTFGSKVG--N VECGAGHFCHDNQSCCKDSQGG      536
Mouse   ................... .VDFI..PVL..L.P...--. ....E........T.....A.V   536

Human   ......RQ....A.R.....A..R.A.R...... REA....AP.....L.Q..              593
  Rat   WACCPYVKGVCCRDGRHCCPIGFHCSAKGTKCLR KKTPRWDILLRDPAPRPLL              589
Mouse   ......L..............G......R...... ..I.....MF....V.....            589
```

Figure 20B

```
Rat 1    GSC-QIRDHCPDGYSCLLTVSGTSSCCPFSEGVSCDDGQHCCPRGFHCSADGKSCSQ
Rat 2    VQCPGSQFECPDSATCCIMIDGSWGCCPMPQASCCEDRVHCCPHGASCDLVHTRCIS
Rat 3    VVCPDAKTQCPDDSTCCELPTGKYGCCPMPNAICCSDHLHCCPQDTVCDLIQSKCIS
Rat 4    VKC-DLEVSCPDGYTCCRLNTGAWGCCPFTKAVCCEDHIHCCPAGFQCHTETGTCEL
Rat 5    VPC-DDFSSCPSNNTCCRLSSGDWGCCPIPEAVCCLDHQHCCPQGFKCMDEG-YCQK
Rat 6    IGC-DQHTSCPVGQTCCPSLKGSWACCQLPHAVCCEDRQHCCPAGYTCNVKARTCEK
Rat 7    VEC-GAGHFCHDNQSCCKDSQGGWACCPYVKGVCCRDGRHCCPIGFHCSAKGTKCLR

Mouse 1  GSC-QTHGHCPAGYSCLLTVSGTSSCCPFSKGVSCGDGYHCCPQGFHCSADGKSCFQ
Mouse 2  VQCPGSQFECPDSATCCIMVDGSWGCCPMPQASCCEDRVHCCPHGASCDLVHTRCVS
Mouse 3  VVCPDAKTQCPDDSTCCELPTGKYGCCPMPNAICCSDHLHCCPQDTVCDLIQSKCLS
Mouse 4  VKC-DMEVSCPEGYTCCRLNTGAWGCCPFAKAVCCEDHIHCCPAGFQCHTEKGTCEM
Mouse 5  TPC-DDFTRCPTNNTCCKLNSGDWGCCPIPEAVCCSDNQHCCPQGFTCLAQG-YCQK
Mouse 6  IGC-DQHTSCPVGQTCCPSLKGSWACCQLPHAVCCEDRQHCCPAGYTCNVKARTCEK
Mouse 7  VEC-GEGHFCHDNQTCCKDSAGVWACCPYLKGVCCRDGRHCCPGGFHCSARGTKCLR Human 1  GPC-QVDAHCSAGHSCIFTVSGTSSCCPFPEAVACGDGHHCCPRGFHCSADGRSCFQ
Human 2  IQCPDSQFECPDFSTCCVMVDGSWGCCPMPQASCCEDRVHCCPHGAFCDLVHTRCIT
Human 3  VMCPDARSRCPDGSTCCELPSGKYGCCPMPNATCCSDHLHCCPQDTVCDLIQSKCLS
Human 4  VKC-DMEVSCPDGYTCCRLQSGAWGCCPFTQAVCCEDHIHCCPAGFTCDTQKGTCEQ
Human 5  VPC-DNVSSCPSSDTCCQLTSGEWGCCPIPEAVCCSDHQHCCPQGYTCVAEG-QCQR
Human 6  IGC-DQHTSCPVGQTCCPSLGGSWACCQLPHAVCCEDRQHCCPAGYTCNVKARSCEK
Human 7  VEC-GEGHFCHDNQTCCRDNRQGWACCPYRQGVCCADRRHCCPAGFRCAARGTKCLR
```

Figure 20C $$vxCx_{5-6}Cx_5CCx_8CCx_6CCxDx_2HCCPx_4Cx_{5-6}Cx_2$$

Figure 20D

| | |
|---|---|
| Tomato Protease | T E C - D E Y S Q C A V G T T C C C I L Q F R R S C F S W G C C P |
| Epithelin 1 | V K C - D L E V S C P D G Y T C C - - - - R L N T G A W G C C P |
| Epithelin 2 | V V C P D A K T Q C P D D S T C C - - - - E L P T G K Y G C C P |

| | |
|---|---|
| Tomato Protease | L E G A T C C E D H Y S C C P H D Y P I C N V R Q G T C S M |
| Epithelin 1 | F T K A V C C E D H I H C C P A G F - Q C H T E T G T C E L |
| Epithelin 2 | M P N A I C C S D H L H C C P Q D T - V C D L I Q S K C I S |

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 1767 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 1..1767

( x i ) SEQUENCE DESCRIPTION: SEQ ID NO:1:

```
ATG  TGG  ATC  CTG  GTG  AGC  TGG  CTG  GCC  TTA  GTG  GCA  AGG  CTG  GTG  GCT      48
Met  Trp  Ile  Leu  Val  Ser  Trp  Leu  Ala  Leu  Val  Ala  Arg  Leu  Val  Ala
 1              5                        10                       15

GGA  ACA  CAG  TGC  CCA  GAT  GGT  CAA  TTC  TGC  CCT  GTT  GCC  TGC  TGC  CTT      96
Gly  Thr  Gln  Cys  Pro  Asp  Gly  Gln  Phe  Cys  Pro  Val  Ala  Cys  Cys  Leu
              20                        25                       30

GAC  CAG  GGA  GGA  GCC  AAC  TAC  AGC  TGC  TGT  AAC  CCT  CTT  CTG  GAC  ACA     144
Asp  Gln  Gly  Gly  Ala  Asn  Tyr  Ser  Cys  Cys  Asn  Pro  Leu  Leu  Asp  Thr
         35                        40                       45

TGG  CCT  ATA  ATA  ACG  AGC  CGT  CGT  CTA  GAT  GGC  TCC  TGC  CAG  ATC  CGT     192
Trp  Pro  Ile  Ile  Thr  Ser  Arg  Arg  Leu  Asp  Gly  Ser  Cys  Gln  Ile  Arg
     50                        55                       60

GAC  CAC  TGT  CCT  GAT  GGC  TAC  TCT  TGT  CTT  CTC  ACT  GTG  TCT  GGG  ACT     240
Asp  His  Cys  Pro  Asp  Gly  Tyr  Ser  Cys  Leu  Leu  Thr  Val  Ser  Gly  Thr
 65                       70                       75                       80

TCC  AGC  TGC  TGC  CCG  TTC  TCT  GAG  GGT  GTA  TCT  TGT  GAT  GAT  GGC  CAG     288
Ser  Ser  Cys  Cys  Pro  Phe  Ser  Glu  Gly  Val  Ser  Cys  Asp  Asp  Gly  Gln
                          85                       90                       95

CAC  TGC  TGC  CCC  CGG  GGC  TTC  CAC  TGT  AGT  GCG  GAT  GGG  AAA  TCC  TGC     336
His  Cys  Cys  Pro  Arg  Gly  Phe  His  Cys  Ser  Ala  Asp  Gly  Lys  Ser  Cys
                  100                      105                     110

TCT  CAG  ATA  TCA  GAT  AGC  CTC  TTG  GGT  GCT  GTC  CAG  TGT  CCT  GGT  AGC     384
Ser  Gln  Ile  Ser  Asp  Ser  Leu  Leu  Gly  Ala  Val  Gln  Cys  Pro  Gly  Ser
             115                      120                     125
```

```
CAG TTC GAA TGT CCT GAC TCC GCC ACC TGC TGT ATT ATG ATT GAT GGT      432
Gln Phe Glu Cys Pro Asp Ser Ala Thr Cys Cys Ile Met Ile Asp Gly
    130             135                 140

TCC TGG GGG TGC TGC CCC ATG CCC CAG GCC TCT TGC TGT GAA GAC AGA      480
Ser Trp Gly Cys Cys Pro Met Pro Gln Ala Ser Cys Cys Glu Asp Arg
145             150                 155                 160

GTG CAT TGC TGT CCC CAC GGG GCC TCC TGT GAC CTG GTT CAC ACG CGA      528
Val His Cys Cys Pro His Gly Ala Ser Cys Asp Leu Val His Thr Arg
                165                 170                 175

TGC ATT TCA CCC ACG GGC ACC CAC CCC TTA CTA AAG AAA TTC CCC GCA      576
Cys Ile Ser Pro Thr Gly Thr His Pro Leu Leu Lys Lys Phe Pro Ala
            180                 185                 190

CAA AGG ACC AAC AGG GCA GTG GCT TTC CCT TTT TCC GTG GTG TGC CCT      624
Gln Arg Thr Asn Arg Ala Val Ala Phe Pro Phe Ser Val Val Cys Pro
        195                 200                 205

GAT GCT AAG ACC CAG TGC CCT GAT GAC TCT ACC TGC TGT GAG CTA CCC      672
Asp Ala Lys Thr Gln Cys Pro Asp Asp Ser Thr Cys Cys Glu Leu Pro
    210                 215                 220

ACT GGG AAG TAT GGC TGT TGT CCA ATG CCC AAC GCC ATC TGC TGT TCC      720
Thr Gly Lys Tyr Gly Cys Cys Pro Met Pro Asn Ala Ile Cys Cys Ser
225             230                 235                 240

GAC CAC CTG CAC TGC TGC CCC CAG GAC ACT GTA TGT GAC CTG ATC CAG      768
Asp His Leu His Cys Cys Pro Gln Asp Thr Val Cys Asp Leu Ile Gln
                245                 250                 255

AGC AAG TGC ATA TCC AAG GAC TAC ACC ACA GAT CTC ATG ACC AAG CTG      816
Ser Lys Cys Ile Ser Lys Asp Tyr Thr Thr Asp Leu Met Thr Lys Leu
            260                 265                 270

CCT GGA TAC CCA GTG AAT GAG GTG AAG TGC GAC TTG GAG GTG AGC TGT      864
Pro Gly Tyr Pro Val Asn Glu Val Lys Cys Asp Leu Glu Val Ser Cys
        275                 280                 285

CCT GAT GGC TAC ACC TGC TGC CGC CTC AAC ACT GGG GCC TGG GGC TGC      912
Pro Asp Gly Tyr Thr Cys Cys Arg Leu Asn Thr Gly Ala Trp Gly Cys
    290                 295                 300

TGT CCA TTC ACC AAG GCT GTG TGT TGT GAA GAC CAC ATT CAC TGC TGC      960
Cys Pro Phe Thr Lys Ala Val Cys Cys Glu Asp His Ile His Cys Cys
305             310                 315                 320

CCA GCC GGG TTT CAG TGT CAC ACA GAG ACA GGA ACC TGT GAA CTG GGA     1008
Pro Ala Gly Phe Gln Cys His Thr Glu Thr Gly Thr Cys Glu Leu Gly
                325                 330                 335

GTC CTT CAG GTA CCC TGG ATG AAA AAG GTC ACG GCC TCC CTC AGC CTG     1056
Val Leu Gln Val Pro Trp Met Lys Lys Val Thr Ala Ser Leu Ser Leu
            340                 345                 350

CCA GAC CCA CAG ATC TTG AAG AAT GAT GTC CCC TGT GAT GAC TTC AGT     1104
Pro Asp Pro Gln Ile Leu Lys Asn Asp Val Pro Cys Asp Asp Phe Ser
        355                 360                 365

AGC TGT CCT TCT AAC AAT ACC TGC TGC AGA CTC AGT TCT GGG GAC TGG     1152
Ser Cys Pro Ser Asn Asn Thr Cys Cys Arg Leu Ser Ser Gly Asp Trp
    370                 375                 380

GGC TGC TGT CCC ATC CCA GAG GCT GTC TGC TGC TTA GAC CAC CAG CAT     1200
Gly Cys Cys Pro Ile Pro Glu Ala Val Cys Cys Leu Asp His Gln His
385             390                 395                 400

TGC TGC CCT CAG GGT TTC AAA TGT ATG GAT GAG GGG TAC TGT CAG AAG     1248
Cys Cys Pro Gln Gly Phe Lys Cys Met Asp Glu Gly Tyr Cys Gln Lys
                405                 410                 415

GGA GAC AGA ATG GTG GCT GGC CTG GAG AAG ATG CCT GTC CGC CAG ACA     1296
Gly Asp Arg Met Val Ala Gly Leu Glu Lys Met Pro Val Arg Gln Thr
            420                 425                 430

ACT CTG CTC CAA CAT GGA GAT ATT GGT TGT GAC CAG CAT ACC AGC TGC     1344
Thr Leu Leu Gln His Gly Asp Ile Gly Cys Asp Gln His Thr Ser Cys
        435                 440                 445

CCA GTA GGG CAA ACA TGC TGC CCA AGC CTG AAG GGA AGT TGG GCC TGC     1392
Pro Val Gly Gln Thr Cys Cys Pro Ser Leu Lys Gly Ser Trp Ala Cys
```

|  |  |  |  |  |  |  |  |  |  |  |  |  |  |  |  |  |
|---|---|---|---|---|---|---|---|---|---|---|---|---|---|---|---|---|
| | 450 | | | | | 455 | | | | | | 460 | | | | |
| TGC | CAG | TTG | CCC | CAT | GCT | GTG | TGC | TGT | GAG | GAC | CGG | CAG | CAC | TGT | TGC | 1440 |
| Cys | Gln | Leu | Pro | His | Ala | Val | Cys | Cys | Glu | Asp | Arg | Gln | His | Cys | Cys | |
| 465 | | | | 470 | | | | | 475 | | | | | | 480 | |
| CCG | GCT | GGG | TAC | ACC | TGC | AAC | GTG | AAG | GCG | AGA | ACC | TGT | GAG | AAG | GAT | 1488 |
| Pro | Ala | Gly | Tyr | Thr | Cys | Asn | Val | Lys | Ala | Arg | Thr | Cys | Glu | Lys | Asp | |
| | | | | 485 | | | | | 490 | | | | | 495 | | |
| GCA | GGC | TCT | GTC | CAG | CCT | TCC | ATG | GAC | CTG | ACC | TTT | GGC | TCT | AAG | GTT | 1536 |
| Ala | Gly | Ser | Val | Gln | Pro | Ser | Met | Asp | Leu | Thr | Phe | Gly | Ser | Lys | Val | |
| | | | 500 | | | | | 505 | | | | | 510 | | | |
| GGG | AAT | GTG | GAA | TGT | GGT | GCC | GGA | CAT | TTC | TGC | CAT | GAT | AAC | CAG | TCC | 1584 |
| Gly | Asn | Val | Glu | Cys | Gly | Ala | Gly | His | Phe | Cys | His | Asp | Asn | Gln | Ser | |
| | | 515 | | | | | 520 | | | | | 525 | | | | |
| TGT | TGT | AAA | GAC | AGC | CAA | GGA | GGC | TGG | GCC | TGC | TGT | CCC | TAT | GTA | AAG | 1632 |
| Cys | Cys | Lys | Asp | Ser | Gln | Gly | Gly | Trp | Ala | Cys | Cys | Pro | Tyr | Val | Lys | |
| | | 530 | | | | | 535 | | | | | 540 | | | | |
| GGT | GTC | TGC | TGT | AGA | GAT | GGA | CGT | CAC | TGT | TGT | CCC | ATT | GGC | TTC | CAC | 1680 |
| Gly | Val | Cys | Cys | Arg | Asp | Gly | Arg | His | Cys | Cys | Pro | Ile | Gly | Phe | His | |
| 545 | | | | 550 | | | | | 555 | | | | | | 560 | |
| TGT | TCA | GCC | AAG | GGA | ACC | AAG | TGT | TTG | CGG | AAG | AAG | ACC | CCT | CGC | TGG | 1728 |
| Cys | Ser | Ala | Lys | Gly | Thr | Lys | Cys | Leu | Arg | Lys | Lys | Thr | Pro | Arg | Trp | |
| | | | | 565 | | | | | 570 | | | | | 575 | | |
| GAC | ATA | CTT | TTG | AGG | GAT | CCA | GCC | CCA | AGA | CCG | CTA | CTG | | | | 1767 |
| Asp | Ile | Leu | Leu | Arg | Asp | Pro | Ala | Pro | Arg | Pro | Leu | Leu | | | | |
| | | | 580 | | | | | 585 | | | | | | | | |

( 2 ) INFORMATION FOR SEQ ID NO:2:

( i ) SEQUENCE CHARACTERISTICS:
        ( A ) LENGTH: 589 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Trp | Ile | Leu | Val | Ser | Trp | Leu | Ala | Leu | Val | Ala | Arg | Leu | Val | Ala |
|---|---|---|---|---|---|---|---|---|---|---|---|---|---|---|---|
| 1 | | | | 5 | | | | | 10 | | | | | 15 | |
| Gly | Thr | Gln | Cys | Pro | Asp | Gly | Gln | Phe | Cys | Pro | Val | Ala | Cys | Cys | Leu |
| | | | 20 | | | | | 25 | | | | | 30 | | |
| Asp | Gln | Gly | Gly | Ala | Asn | Tyr | Ser | Cys | Cys | Asn | Pro | Leu | Leu | Asp | Thr |
| | | 35 | | | | | 40 | | | | | 45 | | | |
| Trp | Pro | Ile | Ile | Thr | Ser | Arg | Arg | Leu | Asp | Gly | Ser | Cys | Gln | Ile | Arg |
| | 50 | | | | | 55 | | | | | 60 | | | | |
| Asp | His | Cys | Pro | Asp | Gly | Tyr | Ser | Cys | Leu | Leu | Thr | Val | Ser | Gly | Thr |
| 65 | | | | 70 | | | | | 75 | | | | | | 80 |
| Ser | Ser | Cys | Cys | Pro | Phe | Ser | Glu | Gly | Val | Ser | Cys | Asp | Asp | Gly | Gln |
| | | | | 85 | | | | | 90 | | | | | 95 | |
| His | Cys | Cys | Pro | Arg | Gly | Phe | His | Cys | Ser | Ala | Asp | Gly | Lys | Ser | Cys |
| | | | 100 | | | | | 105 | | | | | 110 | | |
| Ser | Gln | Ile | Ser | Asp | Ser | Leu | Leu | Gly | Ala | Val | Gln | Cys | Pro | Gly | Ser |
| | | | 115 | | | | 120 | | | | | 125 | | | |
| Gln | Phe | Glu | Cys | Pro | Asp | Ser | Ala | Thr | Cys | Cys | Ile | Met | Ile | Asp | Gly |
| | 130 | | | | | 135 | | | | | 140 | | | | |
| Ser | Trp | Gly | Cys | Cys | Pro | Met | Pro | Gln | Ala | Ser | Cys | Cys | Glu | Asp | Arg |
| 145 | | | | | 150 | | | | | 155 | | | | | 160 |
| Val | His | Cys | Cys | Pro | His | Gly | Ala | Ser | Cys | Asp | Leu | Val | His | Thr | Arg |
| | | | | 165 | | | | | 170 | | | | | 175 | |
| Cys | Ile | Ser | Pro | Thr | Gly | Thr | His | Pro | Leu | Leu | Lys | Lys | Phe | Pro | Ala |
| | | | 180 | | | | | 185 | | | | | 190 | | |

| | | | | | | | | | | | | | | |
|---|---|---|---|---|---|---|---|---|---|---|---|---|---|---|
| Gln | Arg | Thr | Asn | Arg | Ala | Val | Ala | Phe | Pro | Phe | Ser | Val | Val | Cys | Pro |
| | | 195 | | | | 200 | | | | | 205 | | | | |
| Asp | Ala | Lys | Thr | Gln | Cys | Pro | Asp | Asp | Ser | Thr | Cys | Cys | Glu | Leu | Pro |
| | 210 | | | | 215 | | | | 220 | | | | | | |
| Thr | Gly | Lys | Tyr | Gly | Cys | Cys | Pro | Met | Pro | Asn | Ala | Ile | Cys | Cys | Ser |
| 225 | | | | | 230 | | | | 235 | | | | | | 240 |
| Asp | His | Leu | His | Cys | Cys | Pro | Gln | Asp | Thr | Val | Cys | Asp | Leu | Ile | Gln |
| | | | | 245 | | | | | 250 | | | | | 255 | |
| Ser | Lys | Cys | Ile | Ser | Lys | Asp | Tyr | Thr | Thr | Asp | Leu | Met | Thr | Lys | Leu |
| | | | 260 | | | | | 265 | | | | | 270 | | |
| Pro | Gly | Tyr | Pro | Val | Asn | Glu | Val | Lys | Cys | Asp | Leu | Glu | Val | Ser | Cys |
| | | 275 | | | | 280 | | | | | 285 | | | | |
| Pro | Asp | Gly | Tyr | Thr | Cys | Cys | Arg | Leu | Asn | Thr | Gly | Ala | Trp | Gly | Cys |
| | 290 | | | | | 295 | | | | | 300 | | | | |
| Cys | Pro | Phe | Thr | Lys | Ala | Val | Cys | Cys | Glu | Asp | His | Ile | His | Cys | Cys |
| 305 | | | | 310 | | | | | 315 | | | | | | 320 |
| Pro | Ala | Gly | Phe | Gln | Cys | His | Thr | Glu | Thr | Gly | Thr | Cys | Glu | Leu | Gly |
| | | | | 325 | | | | | 330 | | | | | 335 | |
| Val | Leu | Gln | Val | Pro | Trp | Met | Lys | Lys | Val | Thr | Ala | Ser | Leu | Ser | Leu |
| | | | 340 | | | | | 345 | | | | | 350 | | |
| Pro | Asp | Pro | Gln | Ile | Leu | Lys | Asn | Asp | Val | Pro | Cys | Asp | Asp | Phe | Ser |
| | | 355 | | | | | 360 | | | | | 365 | | | |
| Ser | Cys | Pro | Ser | Asn | Asn | Thr | Cys | Cys | Arg | Leu | Ser | Ser | Gly | Asp | Trp |
| | 370 | | | | | 375 | | | | | 380 | | | | |
| Gly | Cys | Cys | Pro | Ile | Pro | Glu | Ala | Val | Cys | Cys | Leu | Asp | His | Gln | His |
| 385 | | | | | 390 | | | | | 395 | | | | | 400 |
| Cys | Cys | Pro | Gln | Gly | Phe | Lys | Cys | Met | Asp | Glu | Gly | Tyr | Cys | Gln | Lys |
| | | | | 405 | | | | | 410 | | | | | 415 | |
| Gly | Asp | Arg | Met | Val | Ala | Gly | Leu | Glu | Lys | Met | Pro | Val | Arg | Gln | Thr |
| | | | 420 | | | | | 425 | | | | | 430 | | |
| Thr | Leu | Leu | Gln | His | Gly | Asp | Ile | Gly | Cys | Asp | Gln | His | Thr | Ser | Cys |
| | | | 435 | | | | | 440 | | | | 445 | | | |
| Pro | Val | Gly | Gln | Thr | Cys | Cys | Pro | Ser | Leu | Lys | Gly | Ser | Trp | Ala | Cys |
| | | 450 | | | | 455 | | | | | 460 | | | | |
| Cys | Gln | Leu | Pro | His | Ala | Val | Cys | Cys | Glu | Asp | Arg | Gln | His | Cys | Cys |
| 465 | | | | | 470 | | | | | 475 | | | | | 480 |
| Pro | Ala | Gly | Tyr | Thr | Cys | Asn | Val | Lys | Ala | Arg | Thr | Cys | Glu | Lys | Asp |
| | | | | 485 | | | | | 490 | | | | | 495 | |
| Ala | Gly | Ser | Val | Gln | Pro | Ser | Met | Asp | Leu | Thr | Phe | Gly | Ser | Lys | Val |
| | | | 500 | | | | | 505 | | | | | 510 | | |
| Gly | Asn | Val | Glu | Cys | Gly | Ala | Gly | His | Phe | Cys | His | Asp | Asn | Gln | Ser |
| | | | 515 | | | | 520 | | | | | 525 | | | |
| Cys | Cys | Lys | Asp | Ser | Gln | Gly | Gly | Trp | Ala | Cys | Cys | Pro | Tyr | Val | Lys |
| | 530 | | | | | 535 | | | | | 540 | | | | |
| Gly | Val | Cys | Cys | Arg | Asp | Gly | Arg | His | Cys | Cys | Pro | Ile | Gly | Phe | His |
| 545 | | | | | 550 | | | | | 555 | | | | | 560 |
| Cys | Ser | Ala | Lys | Gly | Thr | Lys | Cys | Leu | Arg | Lys | Lys | Thr | Pro | Arg | Trp |
| | | | | 565 | | | | | 570 | | | | | 575 | |
| Asp | Ile | Leu | Leu | Arg | Asp | Pro | Ala | Pro | Arg | Pro | Leu | Leu | | | |
| | | | 580 | | | | | 585 | | | | | | | |

( 2 ) INFORMATION FOR SEQ ID NO:3:

( i ) SEQUENCE CHARACTERISTICS:
        ( A ) LENGTH: 1779 base pairs
        ( B ) TYPE: nucleic acid
        ( C ) STRANDEDNESS: single (D) TOPOLOGY: linear (ii) MOLECULE TYPE: cDNA (vi) ORIGINAL SOURCE:
 (A) ORGANISM: Homo sapiens
 (F) TISSUE TYPE: Kidney (ix) FEATURE:
 (A) NAME/KEY: CDS
 (B) LOCATION: 1..1779

(xi) SEQUENCE DESCRIPTION: SEQ ID NO:3:

| | | | | | | | | | | | | | | | | |
|---|---|---|---|---|---|---|---|---|---|---|---|---|---|---|---|---|
| ATG | TGG | ACC | CTG | GTG | AGC | TGG | GTG | GCC | TTA | ACA | GCA | GGG | CTG | GTG | GCT | 48 |
| Met | Trp | Thr | Leu | Val | Ser | Trp | Val | Ala | Leu | Thr | Ala | Gly | Leu | Val | Ala | |
| 1 | | | | 5 | | | | | 10 | | | | | 15 | | |
| GGA | ACG | CGG | TGC | CCA | GAT | GGT | CAG | TTC | TGC | CCT | GTG | GCC | TGC | TGC | CTG | 96 |
| Gly | Thr | Arg | Cys | Pro | Asp | Gly | Gln | Phe | Cys | Pro | Val | Ala | Cys | Cys | Leu | |
| | | 20 | | | | | 25 | | | | | 30 | | | | |
| GAC | CCC | GGA | GGA | GCC | AGC | TAC | AGC | TGC | TGC | CGT | CCC | CTT | CTG | GAC | AAA | 144 |
| Asp | Pro | Gly | Gly | Ala | Ser | Tyr | Ser | Cys | Cys | Arg | Pro | Leu | Leu | Asp | Lys | |
| | | 35 | | | | | 40 | | | | | 45 | | | | |
| TGG | CCC | ACA | ACA | CTG | AGC | AGG | CAT | CTG | GGT | GGC | CCC | TGC | CAG | GTT | GAT | 192 |
| Trp | Pro | Thr | Thr | Leu | Ser | Arg | His | Leu | Gly | Gly | Pro | Cys | Gln | Val | Asp | |
| | 50 | | | | | 55 | | | | | 60 | | | | | |
| GCC | CAC | TGC | TCT | GCC | GGC | CAC | TCC | TGC | ATC | TTT | ACC | GTC | TCA | GGG | ACT | 240 |
| Ala | His | Cys | Ser | Ala | Gly | His | Ser | Cys | Ile | Phe | Thr | Val | Ser | Gly | Thr | |
| 65 | | | | | 70 | | | | | 75 | | | | | 80 | |
| TCC | AGT | TGC | TGC | CCC | TTC | CCA | GAG | GCC | GTG | GCA | TGC | GGG | GAT | GGC | CAT | 288 |
| Ser | Ser | Cys | Cys | Pro | Phe | Pro | Glu | Ala | Val | Ala | Cys | Gly | Asp | Gly | His | |
| | | | | 85 | | | | | 90 | | | | | 95 | | |
| CAC | TGC | TGC | CCA | CGG | GGC | TTC | CAC | TGC | AGT | GCA | GAC | GGG | CGA | TCC | TGC | 336 |
| His | Cys | Cys | Pro | Arg | Gly | Phe | His | Cys | Ser | Ala | Asp | Gly | Arg | Ser | Cys | |
| | | | 100 | | | | | 105 | | | | | 110 | | | |
| TTC | CAA | AGA | TCA | GGT | AAC | AAC | TCC | GTG | GGT | GCC | ATC | CAG | TGC | CCT | GAT | 384 |
| Phe | Gln | Arg | Ser | Gly | Asn | Asn | Ser | Val | Gly | Ala | Ile | Gln | Cys | Pro | Asp | |
| | | | 115 | | | | | 120 | | | | | 125 | | | |
| AGT | CAG | TTC | GAA | TGC | CCG | GAC | TTC | TCC | ACG | TGC | TGT | GTT | ATG | GTC | GAT | 432 |
| Ser | Gln | Phe | Glu | Cys | Pro | Asp | Phe | Ser | Thr | Cys | Cys | Val | Met | Val | Asp | |
| | | 130 | | | | | 135 | | | | | 140 | | | | |
| GGC | TCC | TGG | GGG | TGC | TGC | CCC | ATG | CCC | CAG | GCT | TCC | TGC | TGT | GAA | GAC | 480 |
| Gly | Ser | Trp | Gly | Cys | Cys | Pro | Met | Pro | Gln | Ala | Ser | Cys | Cys | Glu | Asp | |
| 145 | | | | | 150 | | | | | 155 | | | | | 160 | |
| AGG | GTG | CAC | TGC | TGT | CCG | CAC | GGT | GCC | TTC | TGC | GAC | CTG | GTT | CAC | ACC | 528 |
| Arg | Val | His | Cys | Cys | Pro | His | Gly | Ala | Phe | Cys | Asp | Leu | Val | His | Thr | |
| | | | | 165 | | | | | 170 | | | | | 175 | | |
| CGC | TGC | ATC | ACA | CCC | ACG | GGC | ACC | CAC | CCC | CTG | GCA | AAG | AAG | CTC | CCT | 576 |
| Arg | Cys | Ile | Thr | Pro | Thr | Gly | Thr | His | Pro | Leu | Ala | Lys | Lys | Leu | Pro | |
| | | | 180 | | | | | 185 | | | | | 190 | | | |
| GCC | CAG | AGG | ACT | AAC | AGG | GCA | GTG | GCC | TTG | TCC | AGC | TCG | GTC | ATG | TGT | 624 |
| Ala | Gln | Arg | Thr | Asn | Arg | Ala | Val | Ala | Leu | Ser | Ser | Ser | Val | Met | Cys | |
| | | 195 | | | | | 200 | | | | | 205 | | | | |
| CCG | GAC | GCA | CGG | TCC | CGG | TGC | CCT | GAT | GGT | TCT | ACC | TGC | TGT | GAG | CTG | 672 |
| Pro | Asp | Ala | Arg | Ser | Arg | Cys | Pro | Asp | Gly | Ser | Thr | Cys | Cys | Glu | Leu | |
| | 210 | | | | | 215 | | | | | 220 | | | | | |
| CCC | AGT | GGG | AAG | TAT | GGC | TGC | TGC | CCA | ATG | CCC | AAC | GCC | ACC | TGC | TGC | 720 |
| Pro | Ser | Gly | Lys | Tyr | Gly | Cys | Cys | Pro | Met | Pro | Asn | Ala | Thr | Cys | Cys | |
| 225 | | | | | 230 | | | | | 235 | | | | | 240 | |
| TCC | GAT | CAC | CTG | CAC | TGC | TGC | CCC | CAA | GAC | ACT | GTG | TGT | GAC | CTG | ATC | 768 |
| Ser | Asp | His | Leu | His | Cys | Cys | Pro | Gln | Asp | Thr | Val | Cys | Asp | Leu | Ile | |
| | | | | 245 | | | | | 250 | | | | | 255 | | |
| CAG | AGT | AAG | TGC | CTC | TCC | AAG | GAG | AAC | GCT | ACC | ACG | GAC | CTC | CTC | ACT | 816 |
| Gln | Ser | Lys | Cys | Leu | Ser | Lys | Glu | Asn | Ala | Thr | Thr | Asp | Leu | Leu | Thr | |
| | | | 260 | | | | | 265 | | | | | 270 | | | |

| | | | | | | | | | | | | | | | | |
|---|---|---|---|---|---|---|---|---|---|---|---|---|---|---|---|---|
| AAG | CTG | CCT | GCG | CAC | ACA | GTG | GGG | GAT | GTG | AAA | TGT | GAC | ATG | GAG | GTG | 864 |
| Lys | Leu | Pro | Ala | His | Thr | Val | Gly | Asp | Val | Lys | Cys | Asp | Met | Glu | Val | |
| | | 275 | | | | | 280 | | | | | 285 | | | | |
| AGC | TGC | CCA | GAT | GGC | TAT | ACC | TGC | TGC | CGT | CTA | CAG | TCG | GGG | GCC | TGG | 912 |
| Ser | Cys | Pro | Asp | Gly | Tyr | Thr | Cys | Cys | Arg | Leu | Gln | Ser | Gly | Ala | Trp | |
| | | 290 | | | | 295 | | | | | 300 | | | | | |
| GGC | TGC | TGC | CCT | TTT | ACC | CAG | GCT | GTG | TGC | TGT | GAG | GAC | CAC | ATA | CAC | 960 |
| Gly | Cys | Cys | Pro | Phe | Thr | Gln | Ala | Val | Cys | Cys | Glu | Asp | His | Ile | His | |
| 305 | | | | | 310 | | | | | 315 | | | | | 320 | |
| TGC | TGT | CCC | GCG | GGG | TTT | ACG | TGT | GAC | ACG | CAG | AAG | GGT | ACC | TGT | GAA | 1008 |
| Cys | Cys | Pro | Ala | Gly | Phe | Thr | Cys | Asp | Thr | Gln | Lys | Gly | Thr | Cys | Glu | |
| | | | | 325 | | | | | 330 | | | | | 335 | | |
| CAG | GGG | CCC | CAC | CAG | GTG | CCC | TGG | ATG | GAG | AAG | GCC | CCA | GCT | CAC | CTC | 1056 |
| Gln | Gly | Pro | His | Gln | Val | Pro | Trp | Met | Glu | Lys | Ala | Pro | Ala | His | Leu | |
| | | | | 340 | | | | | 345 | | | | | 350 | | |
| AGC | CTG | CCA | GAC | CCA | CAA | GCC | TTG | AAG | AGA | GAT | GTC | CCC | TGT | GAT | AAT | 1104 |
| Ser | Leu | Pro | Asp | Pro | Gln | Ala | Leu | Lys | Arg | Asp | Val | Pro | Cys | Asp | Asn | |
| | | 355 | | | | | 360 | | | | | 365 | | | | |
| GTC | AGC | AGC | TGT | CCC | TCC | TCC | GAT | ACC | TGC | TGC | CAA | CTC | ACG | TCT | GGG | 1152 |
| Val | Ser | Ser | Cys | Pro | Ser | Ser | Asp | Thr | Cys | Cys | Gln | Leu | Thr | Ser | Gly | |
| | 370 | | | | | 375 | | | | | 380 | | | | | |
| GAG | TGG | GGC | TGC | TGT | CCA | ATC | CCA | GAG | GCT | GTC | TGC | TGC | TCG | GAC | CAC | 1200 |
| Glu | Trp | Gly | Cys | Cys | Pro | Ile | Pro | Glu | Ala | Val | Cys | Cys | Ser | Asp | His | |
| 385 | | | | | 390 | | | | | 395 | | | | | 400 | |
| CAG | CAC | TGC | TGC | CCC | CAG | GGC | TAC | ACG | TGT | GTA | GCT | GAG | GGG | CAG | TGT | 1248 |
| Gln | His | Cys | Cys | Pro | Gln | Gly | Tyr | Thr | Cys | Val | Ala | Glu | Gly | Gln | Cys | |
| | | | | 405 | | | | | 410 | | | | | 415 | | |
| CAG | CGA | GGA | AGC | GAG | ATC | GTG | GCT | GGA | CTG | GAG | AAG | ATG | CCT | GCC | CGC | 1296 |
| Gln | Arg | Gly | Ser | Glu | Ile | Val | Ala | Gly | Leu | Glu | Lys | Met | Pro | Ala | Arg | |
| | | | 420 | | | | | 425 | | | | | 430 | | | |
| CGG | GCT | TCC | TTA | TCC | CAC | CCC | AGA | GAC | ATC | GGC | TGT | GAC | CAG | CAC | ACC | 1344 |
| Arg | Ala | Ser | Leu | Ser | His | Pro | Arg | Asp | Ile | Gly | Cys | Asp | Gln | His | Thr | |
| | | 435 | | | | | 440 | | | | | 445 | | | | |
| AGC | TGC | CCG | GTG | GGG | CAG | ACC | TGC | TGC | CCG | AGC | CTG | GGT | GGG | AGC | TGG | 1392 |
| Ser | Cys | Pro | Val | Gly | Gln | Thr | Cys | Cys | Pro | Ser | Leu | Gly | Gly | Ser | Trp | |
| | 450 | | | | | 455 | | | | | 460 | | | | | |
| GCC | TGC | TGC | CAG | TTG | CCC | CAT | GCT | GTG | TGC | TGC | GAG | GAT | CGC | CAG | CAC | 1440 |
| Ala | Cys | Cys | Gln | Leu | Pro | His | Ala | Val | Cys | Cys | Glu | Asp | Arg | Gln | His | |
| 465 | | | | | 470 | | | | | 475 | | | | | 480 | |
| TGC | TGC | CCG | GCT | GGC | TAC | ACC | TGC | AAC | GTG | AAG | GCT | CGA | TCC | TGC | GAG | 1488 |
| Cys | Cys | Pro | Ala | Gly | Tyr | Thr | Cys | Asn | Val | Lys | Ala | Arg | Ser | Cys | Glu | |
| | | | | 485 | | | | | 490 | | | | | 495 | | |
| AAG | GAA | GTG | GTC | TCT | GCC | CAG | CCT | GCC | ACC | TTC | CTG | GCC | CGT | AGC | CCT | 1536 |
| Lys | Glu | Val | Val | Ser | Ala | Gln | Pro | Ala | Thr | Phe | Leu | Ala | Arg | Ser | Pro | |
| | | | 500 | | | | | 505 | | | | | 510 | | | |
| CAC | GTG | GGT | GTG | AAG | GAC | GTG | GAG | TGT | GGG | GAA | GGA | CAC | TTC | TGC | CAT | 1584 |
| His | Val | Gly | Val | Lys | Asp | Val | Glu | Cys | Gly | Glu | Gly | His | Phe | Cys | His | |
| | | 515 | | | | | 520 | | | | | 525 | | | | |
| GAT | AAC | CAG | ACC | TGC | TGC | CGA | GAC | AAC | CGA | CAG | GGC | TGG | GCC | TGC | TGT | 1632 |
| Asp | Asn | Gln | Thr | Cys | Cys | Arg | Asp | Asn | Arg | Gln | Gly | Trp | Ala | Cys | Cys | |
| | 530 | | | | | 535 | | | | | 540 | | | | | |
| CCC | TAC | CGC | CAG | GGC | GTC | TGT | TGT | GCT | GAT | CGG | CGC | CAC | TGC | TGT | CCT | 1680 |
| Pro | Tyr | Arg | Gln | Gly | Val | Cys | Cys | Ala | Asp | Arg | Arg | His | Cys | Cys | Pro | |
| 545 | | | | | 550 | | | | | 555 | | | | | 560 | |
| GCT | GGC | TTC | CGC | TGC | GCA | GCC | AGG | GGT | ACC | AAG | TGT | TTG | CGC | AGG | GAG | 1728 |
| Ala | Gly | Phe | Arg | Cys | Ala | Ala | Arg | Gly | Thr | Lys | Cys | Leu | Arg | Arg | Glu | |
| | | | | 565 | | | | | 570 | | | | | 575 | | |
| GCC | CCG | CGC | TGG | GAC | GCC | CCT | TTG | AGG | GAC | CCA | GCC | TTG | AGA | CAG | CTG | 1776 |
| Ala | Pro | Arg | Trp | Asp | Ala | Pro | Leu | Arg | Asp | Pro | Ala | Leu | Arg | Gln | Leu | |
| | | | 580 | | | | | 585 | | | | | 590 | | | |
| CTG | | | | | | | | | | | | | | | | 1779 |
| Leu | | | | | | | | | | | | | | | | |

( 2 ) INFORMATION FOR SEQ ID NO:4:

( i ) SEQUENCE CHARACTERISTICS:
        ( A ) LENGTH: 593 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Trp Thr Leu Val Ser Trp Val Ala Leu Thr Ala Gly Leu Val Ala
 1               5                  10                  15

Gly Thr Arg Cys Pro Asp Gly Gln Phe Cys Pro Val Ala Cys Cys Leu
                20                  25                  30

Asp Pro Gly Gly Ala Ser Tyr Ser Cys Cys Arg Pro Leu Leu Asp Lys
            35                  40                  45

Trp Pro Thr Thr Leu Ser Arg His Leu Gly Gly Pro Cys Gln Val Asp
        50                  55                  60

Ala His Cys Ser Ala Gly His Ser Cys Ile Phe Thr Val Ser Gly Thr
 65                  70                  75                  80

Ser Ser Cys Cys Pro Phe Pro Glu Ala Val Ala Cys Gly Asp Gly His
                85                  90                  95

His Cys Cys Pro Arg Gly Phe His Cys Ser Ala Asp Gly Arg Ser Cys
                100                 105                 110

Phe Gln Arg Ser Gly Asn Asn Ser Val Gly Ala Ile Gln Cys Pro Asp
            115                 120                 125

Ser Gln Phe Glu Cys Pro Asp Phe Ser Thr Cys Cys Val Met Val Asp
    130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
                180                 185                 190

Ala Gln Arg Thr Asn Arg Ala Val Ala Leu Ser Ser Ser Val Met Cys
            195                 200                 205

Pro Asp Ala Arg Ser Arg Cys Pro Asp Gly Ser Thr Cys Cys Glu Leu
    210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
                245                 250                 255

Gln Ser Lys Cys Leu Ser Lys Glu Asn Ala Thr Thr Asp Leu Leu Thr
            260                 265                 270

Lys Leu Pro Ala His Thr Val Gly Asp Val Lys Cys Asp Met Glu Val
        275                 280                 285

Ser Cys Pro Asp Gly Tyr Thr Cys Cys Arg Leu Gln Ser Gly Ala Trp
    290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
                325                 330                 335

Gln Gly Pro His Gln Val Pro Trp Met Glu Lys Ala Pro Ala His Leu
            340                 345                 350

Ser Leu Pro Asp Pro Gln Ala Leu Lys Arg Asp Val Pro Cys Asp Asn
        355                 360                 365
```

| | | | | | | | | | | | | | | |
|---|---|---|---|---|---|---|---|---|---|---|---|---|---|---|
| Val | Ser | Ser | Cys | Pro | Ser | Ser | Asp | Thr | Cys | Cys | Gln | Leu | Thr | Ser | Gly |
| | 370 | | | | 375 | | | | | 380 | | | | | |
| Glu | Trp | Gly | Cys | Cys | Pro | Ile | Pro | Glu | Ala | Val | Cys | Cys | Ser | Asp | His |
| 385 | | | | | 390 | | | | 395 | | | | | 400 | |
| Gln | His | Cys | Cys | Pro | Gln | Gly | Tyr | Thr | Cys | Val | Ala | Glu | Gly | Gln | Cys |
| | | | | 405 | | | | | 410 | | | | 415 | | |
| Gln | Arg | Gly | Ser | Glu | Ile | Val | Ala | Gly | Leu | Glu | Lys | Met | Pro | Ala | Arg |
| | | | 420 | | | | | 425 | | | | | 430 | | |
| Arg | Ala | Ser | Leu | Ser | His | Pro | Arg | Asp | Ile | Gly | Cys | Asp | Gln | His | Thr |
| | | | 435 | | | | 440 | | | | | 445 | | | |
| Ser | Cys | Pro | Val | Gly | Gln | Thr | Cys | Cys | Pro | Ser | Leu | Gly | Gly | Ser | Trp |
| | 450 | | | | | 455 | | | | | 460 | | | | |
| Ala | Cys | Cys | Gln | Leu | Pro | His | Ala | Val | Cys | Cys | Glu | Asp | Arg | Gln | His |
| 465 | | | | | 470 | | | | 475 | | | | | 480 | |
| Cys | Cys | Pro | Ala | Gly | Tyr | Thr | Cys | Asn | Val | Lys | Ala | Arg | Ser | Cys | Glu |
| | | | | 485 | | | | | 490 | | | | | 495 | |
| Lys | Glu | Val | Val | Ser | Ala | Gln | Pro | Ala | Thr | Phe | Leu | Ala | Arg | Ser | Pro |
| | | | 500 | | | | | 505 | | | | | 510 | | |
| His | Val | Gly | Val | Lys | Asp | Val | Glu | Cys | Gly | Glu | Gly | His | Phe | Cys | His |
| | | | 515 | | | | | 520 | | | | | 525 | | |
| Asp | Asn | Gln | Thr | Cys | Cys | Arg | Asp | Asn | Arg | Gln | Gly | Trp | Ala | Cys | Cys |
| | 530 | | | | | 535 | | | | | 540 | | | | |
| Pro | Tyr | Arg | Gln | Gly | Val | Cys | Cys | Ala | Asp | Arg | Arg | His | Cys | Cys | Pro |
| 545 | | | | | 550 | | | | | 555 | | | | | 560 |
| Ala | Gly | Phe | Arg | Cys | Ala | Ala | Arg | Gly | Thr | Lys | Cys | Leu | Arg | Arg | Glu |
| | | | | 565 | | | | | 570 | | | | | 575 | |
| Ala | Pro | Arg | Trp | Asp | Ala | Pro | Leu | Arg | Asp | Pro | Ala | Leu | Arg | Gln | Leu |
| | | | 580 | | | | | 585 | | | | | 590 | | |
| Leu | | | | | | | | | | | | | | | |

( 2 ) INFORMATION FOR SEQ ID NO:5:

( i ) SEQUENCE CHARACTERISTICS:
        ( A ) LENGTH: 1767 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Mus musculus
        ( F ) TISSUE TYPE: Kidney ( i x ) FEATURE:
        ( A ) NAME/KEY: CDS
        ( B ) LOCATION: 1..1767

( x i ) SEQUENCE DESCRIPTION: SEQ ID NO:5:

| | | | | | | | | | | | | | | | |
|---|---|---|---|---|---|---|---|---|---|---|---|---|---|---|---|
| ATG | TGG | GTC | CTG | ATG | AGC | TGG | CTG | GCC | TTC | GCG | GCA | GGG | CTG | GTA | GCC | 48 |
| Met | Trp | Val | Leu | Met | Ser | Trp | Leu | Ala | Phe | Ala | Ala | Gly | Leu | Val | Ala |
| 1 | | | | 5 | | | | | 10 | | | | | 15 | |
| GGA | ACA | CAG | TGT | CCA | GAT | GGG | CAG | TTC | TGC | CCT | GTT | GCC | TGC | TGC | CTT | 96 |
| Gly | Thr | Gln | Cys | Pro | Asp | Gly | Gln | Phe | Cys | Pro | Val | Ala | Cys | Cys | Leu |
| | | | 20 | | | | | 25 | | | | | 30 | | |
| GAC | CAG | GGA | GGA | GCC | AAC | TAC | AGC | TGC | TGT | AAC | CCT | CTT | CTG | GAC | ACA | 144 |
| Asp | Gln | Gly | Gly | Ala | Asn | Tyr | Ser | Cys | Cys | Asn | Pro | Leu | Leu | Asp | Thr |
| | | | 35 | | | | | 40 | | | | | 45 | | |
| TGG | CCT | AGA | ATA | ACG | AGC | CAT | CAT | CTA | GAT | GGC | TCC | TGC | CAG | ACC | CAT | 192 |
| Trp | Pro | Arg | Ile | Thr | Ser | His | His | Leu | Asp | Gly | Ser | Cys | Gln | Thr | His |
| | | 50 | | | | | 55 | | | | | 60 | | | |
| GGC | CAC | TGT | CCT | GCT | GGC | TAT | TCT | TGT | CTT | CTC | ACT | GTG | TCT | GGG | ACT | 240 |

| | | | | | | | | | | | | | | | | |
|---|---|---|---|---|---|---|---|---|---|---|---|---|---|---|---|---|
| Gly | His | Cys | Pro | Ala | Gly | Tyr | Ser | Cys | Leu | Leu | Thr | Val | Ser | Gly | Thr | |
| 65 | | | | 70 | | | | | 75 | | | | | | 80 | |

| | | | | | | | | | | | | | | | | |
|---|---|---|---|---|---|---|---|---|---|---|---|---|---|---|---|---|
| TCC | AGC | TGC | TGC | CCG | TTC | TCT | AAG | GGT | GTG | TCT | TGT | GGT | GAT | GGC | TAC | 288 |
| Ser | Ser | Cys | Cys | Pro | Phe | Ser | Lys | Gly | Val | Ser | Cys | Gly | Asp | Gly | Tyr | |
| | | | | 85 | | | | | 90 | | | | | 95 | | |
| CAC | TGC | TGC | CCC | CAG | GGC | TTC | CAC | TGT | AGT | GCA | GAT | GGG | AAA | TCC | TGC | 336 |
| His | Cys | Cys | Pro | Gln | Gly | Phe | His | Cys | Ser | Ala | Asp | Gly | Lys | Ser | Cys | |
| | | | 100 | | | | | 105 | | | | | 110 | | | |
| TTC | CAG | ATG | TCA | GAT | AAC | CCC | TTG | GGT | GCT | GTC | CAG | TGT | CCT | GGG | AGC | 384 |
| Phe | Gln | Met | Ser | Asp | Asn | Pro | Leu | Gly | Ala | Val | Gln | Cys | Pro | Gly | Ser | |
| | | | 115 | | | | | 120 | | | | | 125 | | | |
| CAG | TTT | GAA | TGT | CCT | GAC | TCT | GCC | ACC | TGC | TGC | ATT | ATG | GTT | GAT | GGT | 432 |
| Gln | Phe | Glu | Cys | Pro | Asp | Ser | Ala | Thr | Cys | Cys | Ile | Met | Val | Asp | Gly | |
| | | 130 | | | | | 135 | | | | | 140 | | | | |
| TCG | TGG | GGA | TGT | TGT | CCC | ATG | CCC | CAG | GCC | TCT | TGC | TGT | GAA | GAC | AGA | 480 |
| Ser | Trp | Gly | Cys | Cys | Pro | Met | Pro | Gln | Ala | Ser | Cys | Cys | Glu | Asp | Arg | |
| 145 | | | | | 150 | | | | | 155 | | | | | 160 | |
| GTG | CAT | TGC | TGT | CCC | CAT | GGG | GCC | TCC | TGT | GAC | CTG | GTT | CAC | ACA | CGA | 528 |
| Val | His | Cys | Cys | Pro | His | Gly | Ala | Ser | Cys | Asp | Leu | Val | His | Thr | Arg | |
| | | | | 165 | | | | | 170 | | | | | 175 | | |
| TGC | GTT | TCA | CCC | ACG | GGC | ACC | CAC | ACC | CTA | CTA | AAG | AAG | TTC | CCT | GCA | 576 |
| Cys | Val | Ser | Pro | Thr | Gly | Thr | His | Thr | Leu | Leu | Lys | Lys | Phe | Pro | Ala | |
| | | | 180 | | | | | 185 | | | | | 190 | | | |
| CAA | AAG | ACC | AAC | AGG | GCA | GTG | TCT | TTG | CCT | TTT | TCT | GTC | GTG | TGC | CCT | 624 |
| Gln | Lys | Thr | Asn | Arg | Ala | Val | Ser | Leu | Pro | Phe | Ser | Val | Val | Cys | Pro | |
| | | 195 | | | | | 200 | | | | | 205 | | | | |
| GAT | GCT | AAG | ACC | CAG | TGT | CCC | GAT | GAT | TCT | ACC | TGC | TGT | GAG | CTA | CCC | 672 |
| Asp | Ala | Lys | Thr | Gln | Cys | Pro | Asp | Asp | Ser | Thr | Cys | Cys | Glu | Leu | Pro | |
| | 210 | | | | | 215 | | | | | 220 | | | | | |
| ACT | GGG | AAG | TAT | GGC | TGC | TGT | CCA | ATG | CCC | AAT | GCC | ATC | TGC | TGT | TCC | 720 |
| Thr | Gly | Lys | Tyr | Gly | Cys | Cys | Pro | Met | Pro | Asn | Ala | Ile | Cys | Cys | Ser | |
| 225 | | | | | 230 | | | | | 235 | | | | | 240 | |
| GAC | CAC | CTG | CAC | TGC | TGC | CCC | CAG | GAC | ACT | GTA | TGT | GAC | CTG | ATC | CAG | 768 |
| Asp | His | Leu | His | Cys | Cys | Pro | Gln | Asp | Thr | Val | Cys | Asp | Leu | Ile | Gln | |
| | | | | 245 | | | | | 250 | | | | | 255 | | |
| AGT | AAG | TGC | CTA | TCC | AAG | AAC | TAC | ACC | ACG | GAT | CTC | CTG | ACC | AAG | CTG | 816 |
| Ser | Lys | Cys | Leu | Ser | Lys | Asn | Tyr | Thr | Thr | Asp | Leu | Leu | Thr | Lys | Leu | |
| | | | 260 | | | | | 265 | | | | | 270 | | | |
| CCT | GGA | TAC | CCA | GTG | AAG | GAG | GTG | AAG | TGC | GAC | ATG | GAG | GTG | AGC | TGC | 864 |
| Pro | Gly | Tyr | Pro | Val | Lys | Glu | Val | Lys | Cys | Asp | Met | Glu | Val | Ser | Cys | |
| | | 275 | | | | | 280 | | | | | 285 | | | | |
| CCT | GAA | GGA | TAT | ACC | TGC | TGC | CGC | CTC | AAC | ACT | GGG | GCC | TGG | GGC | TGC | 912 |
| Pro | Glu | Gly | Tyr | Thr | Cys | Cys | Arg | Leu | Asn | Thr | Gly | Ala | Trp | Gly | Cys | |
| | 290 | | | | | 295 | | | | | 300 | | | | | |
| TGT | CCA | TTT | GCC | AAG | GCC | GTG | TGT | TGT | GAG | GAT | CAC | ATT | CAT | TGC | TGC | 960 |
| Cys | Pro | Phe | Ala | Lys | Ala | Val | Cys | Cys | Glu | Asp | His | Ile | His | Cys | Cys | |
| 305 | | | | | 310 | | | | | 315 | | | | | 320 | |
| CCG | GCA | GGG | TTT | CAG | TGT | CAC | ACA | GAG | AAA | GGA | ACC | TGC | GAA | ATG | GGT | 1008 |
| Pro | Ala | Gly | Phe | Gln | Cys | His | Thr | Glu | Lys | Gly | Thr | Cys | Glu | Met | Gly | |
| | | | | 325 | | | | | 330 | | | | | 335 | | |
| ATC | CTC | CAA | GTA | CCC | TGG | ATG | AAG | AAG | GTC | ATA | GCC | CCC | CGC | CGC | CTG | 1056 |
| Ile | Leu | Gln | Val | Pro | Trp | Met | Lys | Lys | Val | Ile | Ala | Pro | Arg | Arg | Leu | |
| | | | 340 | | | | | 345 | | | | | 350 | | | |
| CCA | GAC | CCA | CAG | ATC | TTG | AAG | AGT | GAT | ACA | CCT | TGT | GAT | GAC | TTC | ACT | 1104 |
| Pro | Asp | Pro | Gln | Ile | Leu | Lys | Ser | Asp | Thr | Pro | Cys | Asp | Asp | Phe | Thr | |
| | | 355 | | | | | 360 | | | | | 365 | | | | |
| AGG | TGT | CCT | ACA | AAC | AAT | ACC | TGC | TGC | AAA | CTC | AAT | TCT | GGG | GAC | TGG | 1152 |
| Arg | Cys | Pro | Thr | Asn | Asn | Thr | Cys | Cys | Lys | Leu | Asn | Ser | Gly | Asp | Trp | |
| | 370 | | | | | 375 | | | | | 380 | | | | | |
| GGC | TGC | TGT | CCC | ATC | CCA | GAG | GCT | GTC | TGC | TGC | TCA | GAC | AAC | CAG | CAT | 1200 |
| Gly | Cys | Cys | Pro | Ile | Pro | Glu | Ala | Val | Cys | Cys | Ser | Asp | Asn | Gln | His | |
| 385 | | | | | 390 | | | | | 395 | | | | | 400 | |

| | | | | | | | | | | | | | | | | |
|---|---|---|---|---|---|---|---|---|---|---|---|---|---|---|---|---|
| TGC | TGC | CCT | CAG | GGC | TTC | ACA | TGT | CTG | GCT | CAG | GGG | TAC | TGT | CAG | AAG | 1248 |
| Cys | Cys | Pro | Gln 405 | Gly | Phe | Thr | Cys | Leu 410 | Ala | Gln | Gly | Tyr | Cys 415 | Gln | Lys | |
| GGA | GAC | ACA | ATG | GTG | GCT | GGC | CTG | GAG | AAG | ATA | CCT | GCC | CGC | CAG | ACA | 1296 |
| Gly | Asp | Thr | Met 420 | Val | Ala | Gly | Leu | Glu 425 | Lys | Ile | Pro | Ala | Arg 430 | Gln | Thr | |
| ACC | CCG | CTC | CAA | ATT | GGA | GAT | ATC | GGT | TGT | GAC | CAG | CAT | ACC | AGC | TGC | 1344 |
| Thr | Pro | Leu 435 | Gln | Ile | Gly | Asp | Ile 440 | Gly | Cys | Asp | Gln | His 445 | Thr | Ser | Cys | |
| CCA | GTA | GGG | CAA | ACC | TGC | TGC | CCA | AGC | CTC | AAG | GGA | AGT | TGG | GCC | TGC | 1392 |
| Pro | Val 450 | Gly | Gln | Thr | Cys | Cys 455 | Pro | Ser | Leu | Lys | Gly 460 | Ser | Trp | Ala | Cys | |
| TGC | CAG | CTG | CCC | CAT | GCT | GTG | TGC | TGT | GAG | GAC | CGG | CAG | CAC | TGT | TGC | 1440 |
| Cys 465 | Gln | Leu | Pro | His 470 | Ala | Val | Cys | Cys | Glu 475 | Asp | Arg | Gln | His | Cys 480 | Cys | |
| CCG | GCC | GGG | TAC | ACC | TGC | AAT | GTG | AAG | GCG | AGG | ACC | TGT | GAG | AAG | GAT | 1488 |
| Pro | Ala | Gly | Tyr | Thr 485 | Cys | Asn | Val | Lys | Ala 490 | Arg | Thr | Cys | Glu | Lys 495 | Asp | |
| GTC | GAT | TTT | ATC | CAG | CCT | CCC | GTG | CTC | CTG | ACC | CTC | GGC | CCT | AAG | GTT | 1536 |
| Val | Asp | Phe | Ile 500 | Gln | Pro | Pro | Val | Leu 505 | Leu | Thr | Leu | Gly | Pro 510 | Lys | Val | |
| GGG | AAT | GTG | GAG | TGT | GGA | GAA | GGG | CAT | TTC | TGC | CAT | GAT | AAC | CAG | ACC | 1584 |
| Gly | Asn | Val 515 | Glu | Cys | Gly | Glu | Gly 520 | His | Phe | Cys | His | Asp 525 | Asn | Gln | Thr | |
| TGT | TGT | AAA | GAC | AGT | GCA | GGA | GTC | TGG | GCC | TGC | TGT | CCC | TAC | CTA | AAG | 1632 |
| Cys | Cys 530 | Lys | Asp | Ser | Ala | Gly 535 | Val | Trp | Ala | Cys | Cys 540 | Pro | Tyr | Leu | Lys | |
| GGT | GTC | TGC | TGT | AGA | GAT | GGA | CGT | CAC | TGT | TGC | CCC | GGT | GGC | TTC | CAC | 1680 |
| Gly 545 | Val | Cys | Cys | Arg | Asp 550 | Gly | Arg | His | Cys | Cys 555 | Pro | Gly | Gly | Phe | His 560 | |
| TGT | TCA | GCC | AGG | GGA | ACC | AAG | TGT | TTG | CGA | AAG | AAG | ATT | CCT | CGC | TGG | 1728 |
| Cys | Ser | Ala | Arg | Gly 565 | Thr | Lys | Cys | Leu | Arg 570 | Lys | Lys | Ile | Pro | Arg 575 | Trp | |
| GAC | ATG | TTT | TTG | AGG | GAT | CCG | GTC | CCA | AGA | CCG | CTA | CTG | | | | 1767 |
| Asp | Met | Phe | Leu 580 | Arg | Asp | Pro | Val | Pro 585 | Arg | Pro | Leu | Leu | | | | |

( 2 ) INFORMATION FOR SEQ ID NO:6:

( i ) SEQUENCE CHARACTERISTICS:
        ( A ) LENGTH: 589 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Met 1 | Trp | Val | Leu | Met 5 | Ser | Trp | Leu | Ala | Phe 10 | Ala | Ala | Gly | Leu | Val 15 | Ala |
| Gly | Thr | Gln | Cys 20 | Pro | Asp | Gly | Gln | Phe 25 | Cys | Pro | Val | Ala | Cys 30 | Cys | Leu |
| Asp | Gln | Gly 35 | Gly | Ala | Asn | Tyr | Ser 40 | Cys | Cys | Asn | Pro | Leu 45 | Leu | Asp | Thr |
| Trp | Pro 50 | Arg | Ile | Thr | Ser | His 55 | His | Leu | Asp | Gly | Ser 60 | Cys | Gln | Thr | His |
| Gly 65 | His | Cys | Pro | Ala | Gly 70 | Tyr | Ser | Cys | Leu | Leu 75 | Thr | Val | Ser | Gly | Thr 80 |
| Ser | Ser | Cys | Cys | Pro 85 | Phe | Ser | Lys | Gly | Val 90 | Ser | Cys | Gly | Asp | Gly 95 | Tyr |
| His | Cys | Cys | Pro 100 | Gln | Gly | Phe | His | Cys 105 | Ser | Ala | Asp | Gly | Lys 110 | Ser | Cys |

| | | | | | | | | | | | | | |
|---|---|---|---|---|---|---|---|---|---|---|---|---|---|
| Phe | Gln | Met 115 | Ser | Asp | Asn | Pro | Leu 120 | Gly | Ala | Val | Gln | Cys 125 | Pro | Gly | Ser |

Phe Gln Met Ser Asp Asn Pro Leu Gly Ala Val Gln Cys Pro Gly Ser
    115                 120                 125

Gln Phe Glu Cys Pro Asp Ser Ala Thr Cys Cys Ile Met Val Asp Gly
    130                 135                 140

Ser Trp Gly Cys Cys Pro Met Pro Gln Ala Ser Cys Cys Glu Asp Arg
145                 150                 155                 160

Val His Cys Cys Pro His Gly Ala Ser Cys Asp Leu Val His Thr Arg
                    165                 170                 175

Cys Val Ser Pro Thr Gly Thr His Thr Leu Leu Lys Lys Phe Pro Ala
            180                 185                 190

Gln Lys Thr Asn Arg Ala Val Ser Leu Pro Phe Ser Val Val Cys Pro
        195                 200                 205

Asp Ala Lys Thr Gln Cys Pro Asp Asp Ser Thr Cys Cys Glu Leu Pro
    210                 215                 220

Thr Gly Lys Tyr Gly Cys Cys Pro Met Pro Asn Ala Ile Cys Cys Ser
225                 230                 235                 240

Asp His Leu His Cys Cys Pro Gln Asp Thr Val Cys Asp Leu Ile Gln
                245                 250                 255

Ser Lys Cys Leu Ser Lys Asn Tyr Thr Thr Asp Leu Leu Thr Lys Leu
            260                 265                 270

Pro Gly Tyr Pro Val Lys Glu Val Lys Cys Asp Met Glu Val Ser Cys
        275                 280                 285

Pro Glu Gly Tyr Thr Cys Cys Arg Leu Asn Thr Gly Ala Trp Gly Cys
    290                 295                 300

Cys Pro Phe Ala Lys Ala Val Cys Cys Glu Asp His Ile His Cys Cys
305                 310                 315                 320

Pro Ala Gly Phe Gln Cys His Thr Glu Lys Gly Thr Cys Glu Met Gly
                325                 330                 335

Ile Leu Gln Val Pro Trp Met Lys Lys Val Ile Ala Pro Arg Arg Leu
            340                 345                 350

Pro Asp Pro Gln Ile Leu Lys Ser Asp Thr Pro Cys Asp Asp Phe Thr
        355                 360                 365

Arg Cys Pro Thr Asn Asn Thr Cys Cys Lys Leu Asn Ser Gly Asp Trp
    370                 375                 380

Gly Cys Cys Pro Ile Pro Glu Ala Val Cys Cys Ser Asp Asn Gln His
385                 390                 395                 400

Cys Cys Pro Gln Gly Phe Thr Cys Leu Ala Gln Gly Tyr Cys Gln Lys
                405                 410                 415

Gly Asp Thr Met Val Ala Gly Leu Glu Lys Ile Pro Ala Arg Gln Thr
            420                 425                 430

Thr Pro Leu Gln Ile Gly Asp Ile Gly Cys Asp Gln His Thr Ser Cys
        435                 440                 445

Pro Val Gly Gln Thr Cys Cys Pro Ser Leu Lys Gly Ser Trp Ala Cys
    450                 455                 460

Cys Gln Leu Pro His Ala Val Cys Cys Glu Asp Arg Gln His Cys Cys
465                 470                 475                 480

Pro Ala Gly Tyr Thr Cys Asn Val Lys Ala Arg Thr Cys Glu Lys Asp
                485                 490                 495

Val Asp Phe Ile Gln Pro Pro Val Leu Leu Thr Leu Gly Pro Lys Val
            500                 505                 510

Gly Asn Val Glu Cys Gly Glu Gly His Phe Cys His Asp Asn Gln Thr
        515                 520                 525

Cys Cys Lys Asp Ser Ala Gly Val Trp Ala Cys Cys Pro Tyr Leu Lys
    530                 535                 540

Gly Val Cys Cys Arg Asp Gly Arg His Cys Cys Pro Gly Gly Phe His

| | | | | | 545 | | | | 550 | | | | | 555 | | | | 560 |
|---|---|---|---|---|---|---|---|---|---|---|---|---|---|---|---|---|---|---|
| Cys | Ser | Ala | Arg | Gly | Thr | Lys | Cys | Leu | Arg | Lys | Lys | Ile | Pro | Arg | Trp |
| | | | | 565 | | | | | 570 | | | | | 575 |
| Asp | Met | Phe | Leu | Arg | Asp | Pro | Val | Pro | Arg | Pro | Leu | Leu |
| | | | | 580 | | | | | 585 |

(2) INFORMATION FOR SEQ ID NO:7:

(i) SEQUENCE CHARACTERISTICS:
        (A) LENGTH: 539 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Bos taurus
        (F) TISSUE TYPE: Kidney (ix) FEATURE:
        (A) NAME/KEY: CDS
        (B) LOCATION: 1..537

(xi) SEQUENCE DESCRIPTION: SEQ ID NO:7:

| AAG | TGG | GGG | TGT | TGC | CCG | ATG | CCC | AAT | GCC | ATT | TGC | TGC | TCC | GAC | CAC | 48 |
|---|---|---|---|---|---|---|---|---|---|---|---|---|---|---|---|---|
| Lys | Trp | Gly | Cys | Cys | Pro | Met | Pro | Asn | Ala | Ile | Cys | Cys | Ser | Asp | His | |
| 1 | | | | 5 | | | | | 10 | | | | | 15 | | |

| CTG | CAC | TGC | TGC | CCC | CAG | AAC | ACT | GTG | TGT | GAC | CTG | ACC | CAG | AGT | AAG | 96 |
|---|---|---|---|---|---|---|---|---|---|---|---|---|---|---|---|---|
| Leu | His | Cys | Cys | Pro | Gln | Asn | Thr | Val | Cys | Asp | Leu | Thr | Gln | Ser | Lys | |
| | | | 20 | | | | | 25 | | | | | 30 | | | |

| TGC | CTC | TCC | AAG | GAG | AAC | GCT | ACG | GAC | CTC | CTC | ACC | AAG | CTG | CCC | GCA | 144 |
|---|---|---|---|---|---|---|---|---|---|---|---|---|---|---|---|---|
| Cys | Leu | Ser | Lys | Glu | Asn | Ala | Thr | Asp | Leu | Leu | Thr | Lys | Leu | Pro | Ala | |
| | | 35 | | | | | 40 | | | | | 45 | | | | |

| CAC | ACA | GTG | CAG | GAT | GTC | AAG | TGC | GAC | ATG | GAG | GTG | AGC | TGC | CCA | GAC | 192 |
|---|---|---|---|---|---|---|---|---|---|---|---|---|---|---|---|---|
| His | Thr | Val | Gln | Asp | Val | Lys | Cys | Asp | Met | Glu | Val | Ser | Cys | Pro | Asp | |
| 50 | | | | | 55 | | | | | 60 | | | | | | |

| GAC | TAC | ACC | TGC | TGC | CGC | CTA | CAG | TCC | GGG | GCC | TGG | GGC | TGC | TGC | CCT | 240 |
|---|---|---|---|---|---|---|---|---|---|---|---|---|---|---|---|---|
| Asp | Tyr | Thr | Cys | Cys | Arg | Leu | Gln | Ser | Gly | Ala | Trp | Gly | Cys | Cys | Pro | |
| 65 | | | | 70 | | | | | 75 | | | | | 80 | | |

| TTT | GTG | CAG | GCC | GTG | TGC | TGT | GAG | GAC | CAT | GTG | CAC | TGC | TGC | CCG | TCC | 288 |
|---|---|---|---|---|---|---|---|---|---|---|---|---|---|---|---|---|
| Phe | Val | Gln | Ala | Val | Cys | Cys | Glu | Asp | His | Val | His | Cys | Cys | Pro | Ser | |
| | | | | 85 | | | | | 90 | | | | | 95 | | |

| GGG | TTT | AGG | TGT | GAC | ACA | GAG | AAG | GGT | GTG | TGT | GAG | CAG | GGG | ACC | CGC | 336 |
|---|---|---|---|---|---|---|---|---|---|---|---|---|---|---|---|---|
| Gly | Phe | Arg | Cys | Asp | Thr | Glu | Lys | Gly | Val | Cys | Glu | Gln | Gly | Thr | Arg | |
| | | | 100 | | | | | 105 | | | | | 110 | | | |

| CAG | GTG | CCG | TGG | ATG | AAG | AAA | GCC | CCA | GCC | CAC | CTC | AGC | CTG | CTG | GAC | 384 |
|---|---|---|---|---|---|---|---|---|---|---|---|---|---|---|---|---|
| Gln | Val | Pro | Trp | Met | Lys | Lys | Ala | Pro | Ala | His | Leu | Ser | Leu | Leu | Asp | |
| | | 115 | | | | | 120 | | | | | 125 | | | | |

| CTC | GGA | GCA | GTG | GAG | GGG | GAC | GTC | CCC | TGT | GAT | AAC | GTC | ACC | AGC | TGT | 432 |
|---|---|---|---|---|---|---|---|---|---|---|---|---|---|---|---|---|
| Leu | Gly | Ala | Val | Glu | Gly | Asp | Val | Pro | Cys | Asp | Asn | Val | Thr | Ser | Cys | |
| | 130 | | | | | 135 | | | | | 140 | | | | | |

| CCT | TCT | TCC | ACT | ACC | TGC | TGT | CGA | CTC | AAG | TCT | GGG | GAG | TGG | GCC | TGC | 480 |
|---|---|---|---|---|---|---|---|---|---|---|---|---|---|---|---|---|
| Pro | Ser | Ser | Thr | Thr | Cys | Cys | Arg | Leu | Lys | Ser | Gly | Glu | Trp | Ala | Cys | |
| 145 | | | | | 150 | | | | | 155 | | | | | 160 | |

| TGT | CCT | GCT | CCA | GAG | GCT | GTC | TGC | TGC | TCG | GAC | CAC | CAG | CAC | TGC | TGT | 528 |
|---|---|---|---|---|---|---|---|---|---|---|---|---|---|---|---|---|
| Cys | Pro | Ala | Pro | Glu | Ala | Val | Cys | Cys | Ser | Asp | His | Gln | His | Cys | Cys | |
| | | | | 165 | | | | | 170 | | | | | 175 | | |

| CCC | CAA | GAT | AC | 539 |
|---|---|---|---|---|
| Pro | Gln | Asp | | |

(2) INFORMATION FOR SEQ ID NO:8:

(i) SEQUENCE CHARACTERISTICS:
        (A) LENGTH: 179 amino acids
        (B) TYPE: amino acid

-continued ( D ) TOPOLOGY: linear ( i i ) MOLECULE TYPE: protein ( x i ) SEQUENCE DESCRIPTION: SEQ ID NO:8:

```
Lys Trp Gly Cys Cys Pro Met Pro Asn Ala Ile Cys Cys Ser Asp His
 1               5                  10                  15

Leu His Cys Cys Pro Gln Asn Thr Val Cys Asp Leu Thr Gln Ser Lys
             20                  25                  30

Cys Leu Ser Lys Glu Asn Ala Thr Asp Leu Leu Thr Lys Leu Pro Ala
         35                  40                  45

His Thr Val Gln Asp Val Lys Cys Asp Met Glu Val Ser Cys Pro Asp
     50                  55                  60

Asp Tyr Thr Cys Cys Arg Leu Gln Ser Gly Ala Trp Gly Cys Cys Pro
 65                  70                  75                  80

Phe Val Gln Ala Val Cys Cys Glu Asp His Val His Cys Cys Pro Ser
                 85                  90                  95

Gly Phe Arg Cys Asp Thr Glu Lys Gly Val Cys Glu Gln Gly Thr Arg
            100                 105                 110

Gln Val Pro Trp Met Lys Lys Ala Pro Ala His Leu Ser Leu Leu Asp
        115                 120                 125

Leu Gly Ala Val Glu Gly Asp Val Pro Cys Asp Asn Val Thr Ser Cys
    130                 135                 140

Pro Ser Ser Thr Thr Cys Cys Arg Leu Lys Ser Gly Glu Trp Ala Cys
145                 150                 155                 160

Cys Pro Ala Pro Glu Ala Val Cys Cys Ser Asp His Gln His Cys Cys
                165                 170                 175

Pro Gln Asp
```

( 2 ) INFORMATION FOR SEQ ID NO:9:

( i ) SEQUENCE CHARACTERISTICS:
( A ) LENGTH: 341 base pairs
( B ) TYPE: nucleic acid
( C ) STRANDEDNESS: single
( D ) TOPOLOGY: linear ( i i ) MOLECULE TYPE: cDNA ( v i ) ORIGINAL SOURCE:
( A ) ORGANISM: Gallus domesticus
( F ) TISSUE TYPE: Kidney ( i x ) FEATURE:
( A ) NAME/KEY: CDS
( B ) LOCATION: 1..339

( x i ) SEQUENCE DESCRIPTION: SEQ ID NO:9:

```
AAG TGG GGT TGT TGC CCC ATG CCG AGA GGC GTG TGC TGC CGG GAT GAG     48
Lys Trp Gly Cys Cys Pro Met Pro Arg Gly Val Cys Cys Arg Asp Glu
 1               5                  10                  15

GAG CAC TGC TGT CCC CAC TCC ACC AGC TGT GAT TTG GAG CGC GGG CGC     96
Glu His Cys Cys Pro His Ser Thr Ser Cys Asp Leu Glu Arg Gly Arg
             20                  25                  30

TGT GTG TCC CCT ACG GGG GAC GTC CCC ATG GCC ACC AAA TTC CCG GCC    144
Cys Val Ser Pro Thr Gly Asp Val Pro Met Ala Thr Lys Phe Pro Ala
         35                  40                  45

TGG AAG AGA CCG CGC GGT GCT GCG GCA CAG CCC CGG CTC CGC GTC CCA    192
Trp Lys Arg Pro Arg Gly Ala Ala Ala Gln Pro Arg Leu Arg Val Pro
     50                  55                  60

GCA GTG GTT GGT GAC GTG AAG TGT GAC GAT GAG ATG AGC TGT CCC GAC    240
Ala Val Val Gly Asp Val Lys Cys Asp Asp Glu Met Ser Cys Pro Asp
 65                  70                  75                  80
```

```
GGG AAC ACG TGC TGC AGG CTG AGC TCC GGG CAG TGG GGG TGC TGC CCG        288
Gly Asn Thr Cys Cys Arg Leu Ser Ser Gly Gln Trp Gly Cys Cys Pro
             85                  90                      95

CTG GAG CAG GCC GTG TGC TGC CCC GAC CAC ATC CAC TGC TGC CCC CAA        336
Leu Glu Gln Ala Val Cys Cys Pro Asp His Ile His Cys Cys Pro Gln
            100                 105                 110

GAT AC                                                                  341
Asp
```

(2) INFORMATION FOR SEQ ID NO:10:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO:10:

```
Lys Trp Gly Cys Cys Pro Met Pro Arg Gly Val Cys Cys Arg Asp Glu
 1               5                  10                      15

Glu His Cys Cys Pro His Ser Thr Ser Cys Asp Leu Glu Arg Gly Arg
             20                  25                  30

Cys Val Ser Pro Thr Gly Asp Val Pro Met Ala Thr Lys Phe Pro Ala
             35                  40                  45

Trp Lys Arg Pro Arg Gly Ala Ala Gln Pro Arg Leu Arg Val Pro
     50                  55                  60

Ala Val Val Gly Asp Val Lys Cys Asp Asp Glu Met Ser Cys Pro Asp
 65                  70                  75                  80

Gly Asn Thr Cys Cys Arg Leu Ser Ser Gly Gln Trp Gly Cys Cys Pro
             85                  90                  95

Leu Glu Gln Ala Val Cys Cys Pro Asp His Ile His Cys Cys Pro Gln
            100                 105                 110

Asp
```

(2) INFORMATION FOR SEQ ID NO:11:

(i) SEQUENCE CHARACTERISTICS:
        (A) LENGTH: 110 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: Cercopithecus aethiops
        (H) CELL LINE: BSC-1

(ix) FEATURE:
        (A) NAME/KEY: CDS
        (B) LOCATION: 28..108

(xi) SEQUENCE DESCRIPTION: SEQ ID NO:11:

```
AGCTTCTGCA GGGGCGGGGC CTCCCCC ATG CCG CCC TCC GGG CTG CGG CTG          51
                              Met Pro Pro Ser Gly Leu Arg Leu
                               1               5

CTG CCG CTG CTG CTA CCG CTG CTG TGG CTA CTG GTG CTG ACG CCT AGC        99
Leu Pro Leu Leu Leu Pro Leu Leu Trp Leu Leu Val Leu Thr Pro Ser
         10                  15                  20

CGG CCG GCC GC                                                         110
Arg Pro Ala
 25
```

(2) INFORMATION FOR SEQ ID NO:12:

( i ) SEQUENCE CHARACTERISTICS:
   ( A ) LENGTH: 27 amino acids
   ( B ) TYPE: amino acid
   ( D ) TOPOLOGY: linear ( i i ) MOLECULE TYPE: protein ( x i ) SEQUENCE DESCRIPTION: SEQ ID NO:12:

Met Pro Pro Ser Gly Leu Arg Leu Leu Pro Leu Leu Leu Pro Leu Leu
 1               5                   10                  15
Trp Leu Leu Val Leu Thr Pro Ser Arg Pro Ala
            20                  25

EPITHELINS: NOVEL CYSTEINE-RICH GROWTH MODULATING PROTEINS

This application is a continuation-in-part of application U.S. Ser. No. 07/504,508, filed Apr. 3, 1990, now abandoned.

1. Introduction
2. Background of the Invention
3. Summary of the Invention
4. Brief Description of the Figures
5. Detailed Description of the Invention
   5.1. Production of Epithelins
      5.1.1. Isolation and Purification of Epithelins From Natural Cell Sources
      5.1.2. Chemical Synthesis of Epithelins
      5.1.3. Synthesis of Epithelins Using Recombinant DNA Technology
         5.1.3.1. Isolation or Generation of Epithelin Genes
         5.1.3.2. Construction of Epithelin Expression Vectors
         5.1.3.3. Identification of Transfectants or Transformants Expressing Epithelin Gene Products
      5.1.4. Epithelin Derivatives, Analogs and Peptides
   5.2. Anti-Epithelin Antibodies
   5.3. Biological Profile of the Epithelins
   5.4. Uses of the Epithelins, Epithelin-Encoding Nucleic Acid Molecules, Anti-Epithelin Antibodies and Epithelin Receptors
      5.4.1. Epithelin Proteins
      5.4.2. Epithelin-Encoding Nucleic Acid Molecules
6. Example: Preparation of Purified Epithelin 1 and Epithelin 2 From Rat Kidney
   6.1. Purification Procedures
      6.1.1. Acid Ethanol Extraction
      6.1.2. Preparative Gel Permeation Chromatography
      6.1.3. Reversed-Phase HPLC of Preparative TSK-250 Fractions
      6.1.4. Further Purification of Epithelin 1 by Reversed-Phase and Gel Permeation HPLC
      6.1.5. Further Purification of Epithelin 2 by Reversed-Phase and Gel Permeation HPLC
   6.2. Bioassays
      6.2.1. Cell Growth Inhibitory Assay Using $^{125}$I-deoxyuridine Incorporation Into DNA
      6.2.2. Cell Growth Inhibitory and Stimulatory Assay Using Murine Keratinocytes
      6.2.3. Soft Agar Colony Assay
   6.3. Primary Structure Determinations
      6.3.1. Reduction and S-Pyridylethylation
      6.3.2. Enzymatic Cleavage of SPE-Epithelin 1 and SPE-Epithelin 2
      6.3.3. Peptide Isolation
      6.3.4. Amino Acid Analysis
      6.3.5. Amino Acid Sequence Determination
      6.3.6. Tricine-Sodium Dodecyl Sulfate-Polyacrylamide Gel Electrophoresis
   6.4. Characteristics of the Epithelins I and II
      6.4.1. Physical and Chemical Properties
      6.4.2. Purification of Epithelin 1 and Epithelin 2 and Certain Physical Properties
      6.4.3. Chemical Structure of Epithelin 1 and Epithelin 2
      6.4.4. Biological Properties of Epithelin 1 and Epithelin 2
7. Example: cDNA Cloning of the Epithelin Precursor and Transient Expression of Precursor and Mature Forms
   7.1 PCR cDNA Cloning
   7.2 Expression in COS Cells

1. INTRODUCTION

The present invention relates to a novel family of growth regulatory proteins which applicants have termed "epithelins", to methods for the production of epithelins, and to their diagnostic and therapeutic uses. Applicants have purified two members of the epithelin family, epithelin 1 and epithelin 2, from natural cell sources and have isolated cDNAs encoding several different epithelins. Epithelin 1 and epithelin 2 share substantial structural similarity yet are functionally distinct proteins. Epithelin 1 is a bifunctional growth regulator, capable of stimulating the growth of some cell types while inhibiting the growth of others. Epithelin 2 is functionally similar to epithelin 1 with respect to growth inhibitory bioactivity. In contrast, however, epithelin 2 is apparently not capable of eliciting the growth stimulatory activity characteristic of epithelin 1 and, in fact, antagonizes this epithelin 1 activity.

2. BACKGROUND OF THE INVENTION

Cellular growth and differentiation appear to be initiated, promoted, maintained, and regulated by a multiplicity of stimulatory, inhibitory, and synergistic factors and hormones. The alteration and/or breakdown of the cellular homeostasis mechanism seems to be a fundamental cause of growth-related diseases, including neoplasia. Growth modulatory factors are implicated in a wide variety of pathological and physiological processes including signal transduction, cell communication, growth and development, embryogenesis, immune response, hematopoiesis, cell survival and differentiation, inflammation, tissue repair and remodeling, atherosclerosis and cancer.

Epidermal growth factor (EGF), transforming growth factor-α (TGFα), platelet-derived growth factor (PDGF), fibroblast growth factor (FGF), nerve growth factor (NGF), transforming growth factor-β (TFGβ), insulin growth factor I and II (IGF I, IGF II), hematopoietic growth factors such as erythropoietin, colony-stimulating factors (CSF 1 and 2), interleukins (IL-1 to 8), interferons (IFN α, β, γ), tumor necrosis factor α and β (TNF α and β), leukoregulin, oncostatin M, amphiregulin (AR) and other less defined factors are growth and differentiation modulatory proteins produced by a variety of cell types either under normal physiological conditions or in response to exogenous stimuli. Most of these factors appear to act in autocrine and paracrine fashions. (For reviews see: Goustin et al., 1986, Cancer Res. 46:1015–1029; Rozengurt, 1986, Science 234:161–166; Pardee, 1987, Cancer Res. 47:1488–1491; Sachs, 1986, Sci. Amer. 254:40–47; Marshall, 1987, Cell 50:5–6; Melcher and Anderson, 1987, Cell 30:715–720; Namen et al., 1988, J. Exp. Med. 167:988–1002; Baggiolini et al., 1989, J. Clin. Invest. 84:1045–1049; Clemens and McNurlan, 1985, Biochem, J. 226:345–360; Nathan, 1987, J. Clin. Invest. 79:319–326; Sporn and Roberts, 1986, J. Clin. Invest. 78:329–332; Old, 1987, Nature 326:330–331; Beutler and Cerami, 1987, New Engl. J. Med. 316:379–385; Weinstein, 1987, J. Cell. Biochem. 33:213–224; Zarling et al., 1987, Proc. Natl. Acad. Sci. U.S.A. 83:9739–9744; Shoyab et al., 1988, Proc. Natl. Acad. Sci. U.S.A., 85:6528–6532; Shoyab et al., 1989, Science 243:1074–1076; Sporn and Todaro, 1985, N. Engl. J. Med. 303:878–880; Sporn and Roberts, 1985, Nature 313:745–747).

There is a great deal of interest in isolating, characterizing, and defining the functional mechanisms of growth modulatory factors because of their potential use in the diagnosis, prognosis, and treatment of cancer. Moreover, acquiring knowledge of these factors will aid in the understanding of the basic mechanisms behind normal growth control and the loss thereof in cancer cells.

3. SUMMARY OF THE INVENTION

The present invention is directed to epithelins, a novel family of low molecular weight, cysteine-rich proteins exhibiting bifunctional growth regulatory activities, to the use of epithelins in the diagnosis and treatment of human diseases, and to methods for the production of biologically active epithelins. Two members of the epithelin family, epithelin 1 and epithelin 2, have been identified and purified to apparent homogeneity, enabling applicants to determine the primary structures, physical properties and functional characteristics of these novel growth modulators. Several other members of the epithelin family have been identified by cDNA cloning. Epithelin 1 is a polypeptide comprising 56 amino acids, while epithelin 2 comprises 57 amino acids. Structurally, epithelin 1 and epithelin 2 share 47% homology at the amino acid level and each contains 12 identically positioned cysteine residues.

Epithelins may be produced by isolation and purification from natural sources, by chemical synthesis, or by recombinant DNA technology. In a particular embodiment of the invention, described more fully by way of example herein (Section 6, infra), epithelin 1 and epithelin 2 are isolated from rat kidney tissue and subsequently purified to apparent homogeneity using a combination of gel permeation and reversed phase high performance liquid chromatography (HPLC). As further described in Section 6, infra, applicants have thoroughly characterized the purified epithelins I and II with respect to their structural, physical, chemical, and functional characteristics.

4. BRIEF DESCRIPTION OF THE FIGURES

FIG. 1. Preparative gel permeation HPLC of crude extract.

Figure 2:
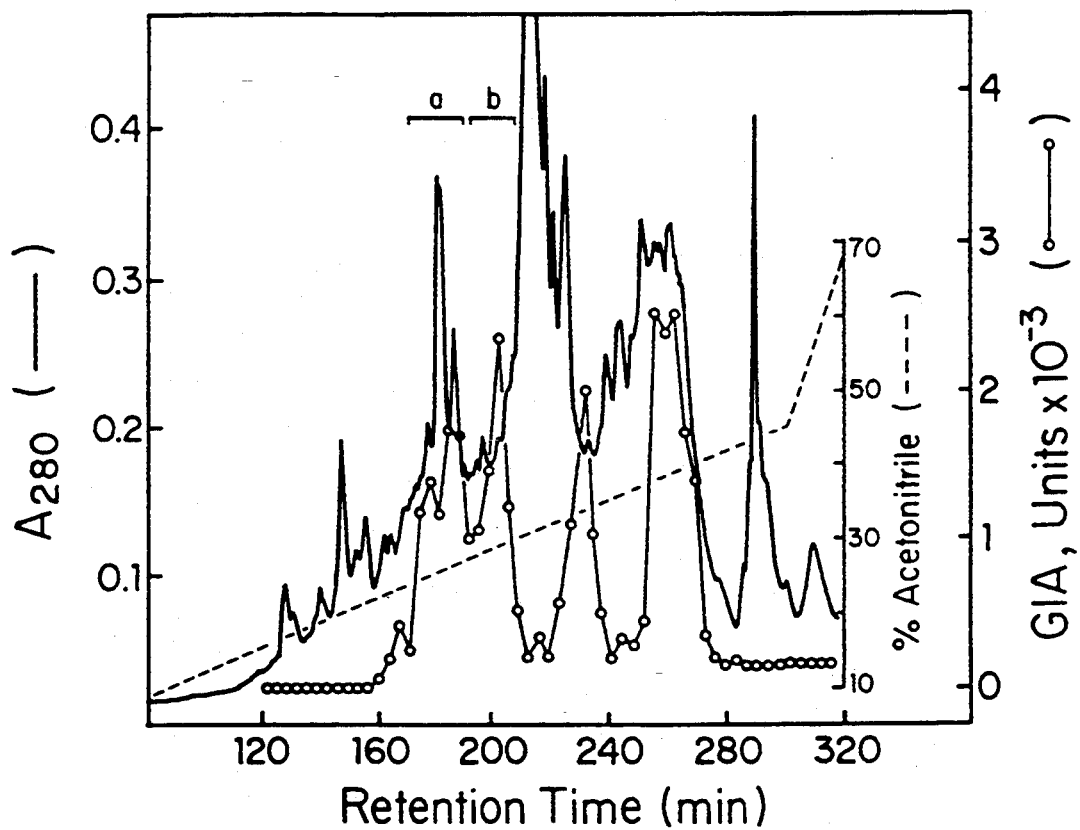

FIG. 2. Preparative reversed phase HPLC of pooled fractions 25–28 from 28 runs of FIG. 1.

Figure 3:
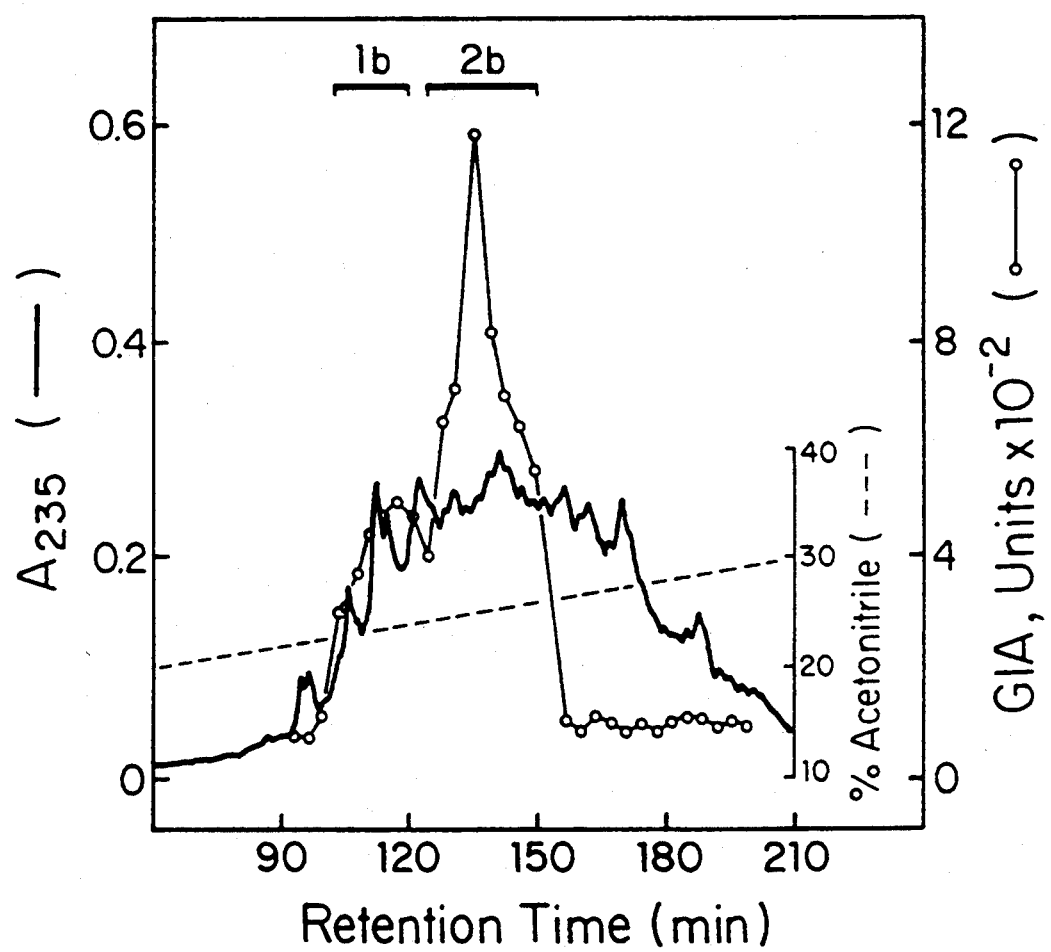

FIG. 3. Semi-preparative reversed phase HPLC of pooled fractions 55–59 from FIG. 2.

Figure 4:
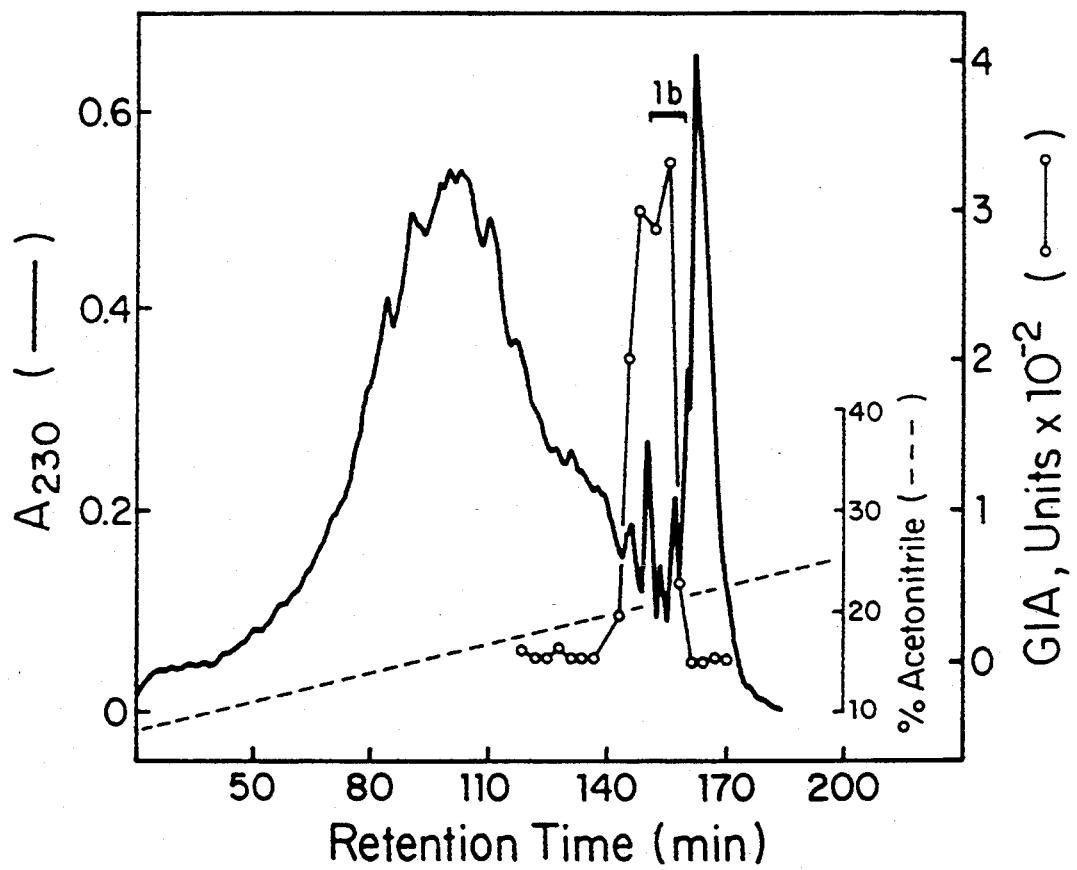

FIG. 4. Analytical reversed phase HPLC of pool 1b from previous run.

Figure 5:
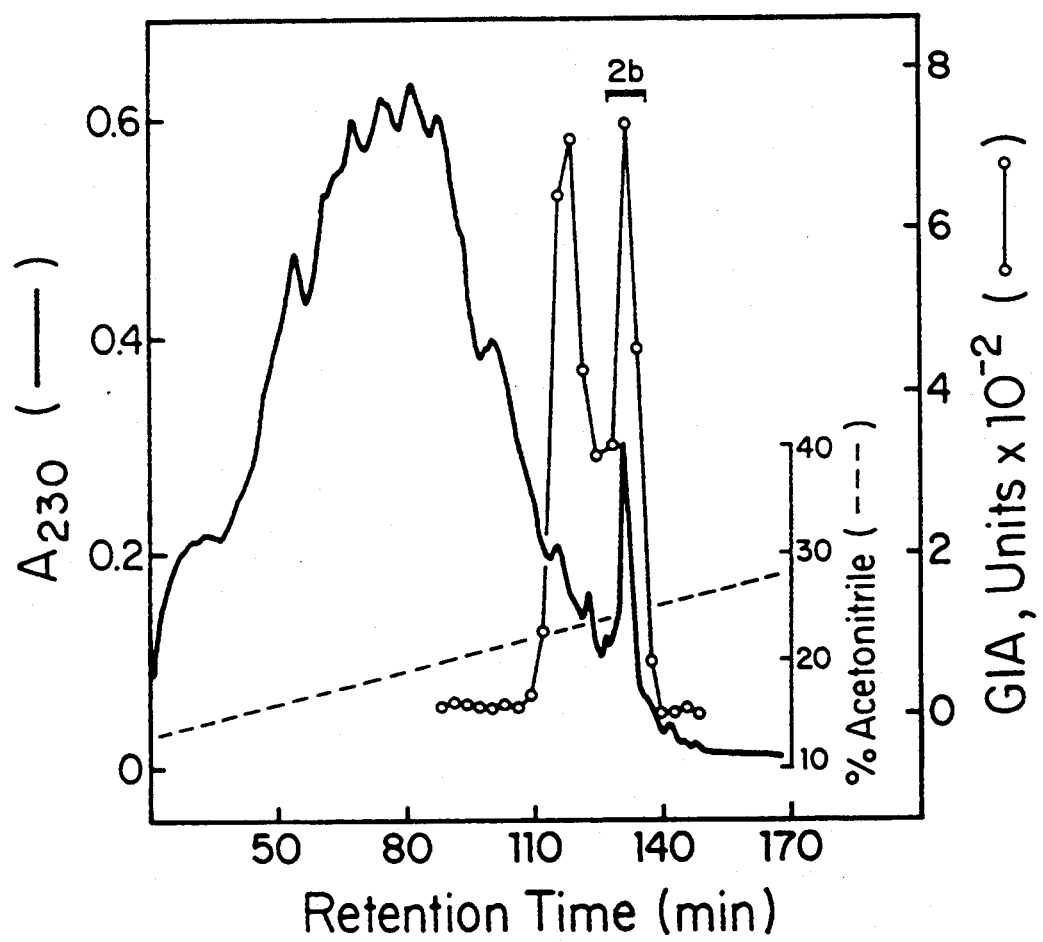

FIG. 5. Analytical reversed phase HPLC of pool 2b from FIG. 3.

FIG. 6. Analytical gel permeation chromatography of the concentrated fractions 51(A) and 52(B) from FIG. 4.

FIG. 7. Analytical gel permeation chromatography of the concentrated fractions 44(A) and 45(B) from FIG. 5.

Figure 8:
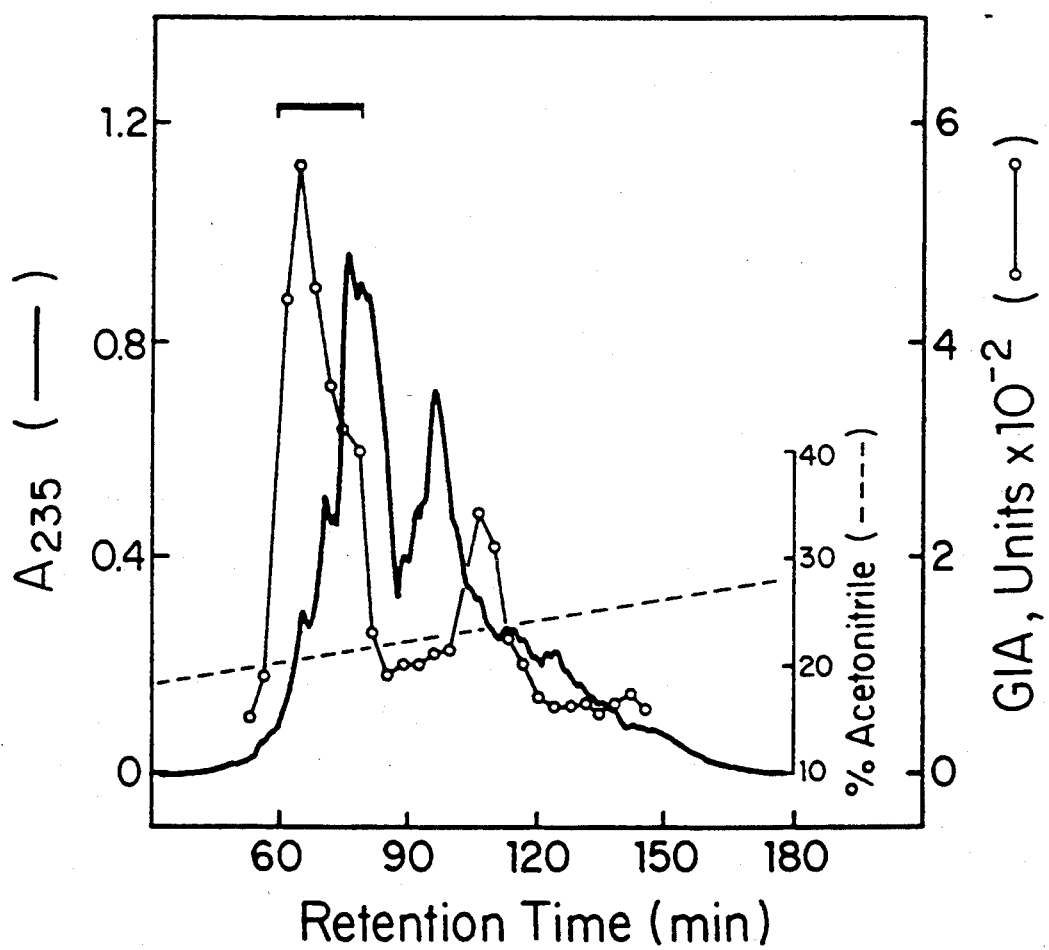

FIG. 8. Semi-preparative reversed phase HPLC of fractions 50–54 from FIG. 2.

Figure 9:
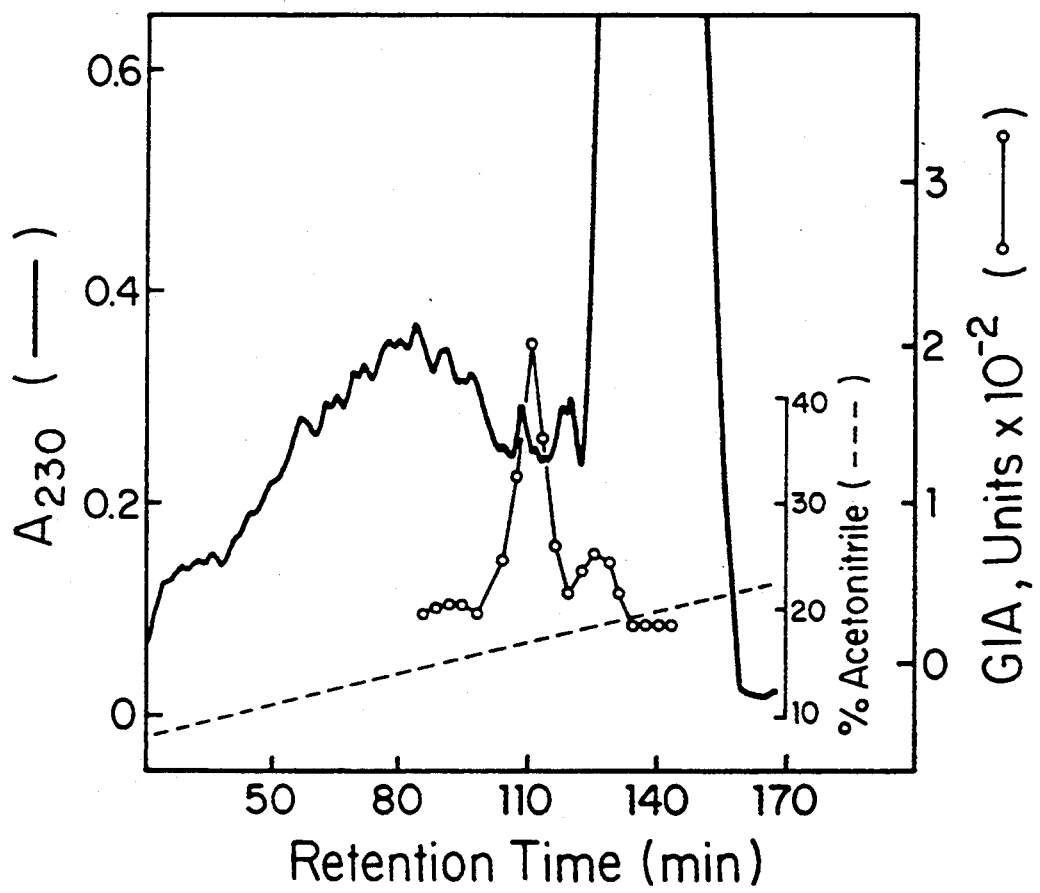

FIG. 9. Analytical reversed phase HPLC of fractions 18–23 from previous run.

FIG. 10. Analytical gel permeation chromatography of fractions from FIG. 9. Chromatography was performed as described in Section 6.1., infra. (A) HPLC of concentrated fraction 36; (B) HPLC of concentrated fraction 37; (C) HPLC of concentrated fraction 38; (D) rechromatography of pooled fractions 48 and 49 from A–C, then concentrated.

Figure 11:
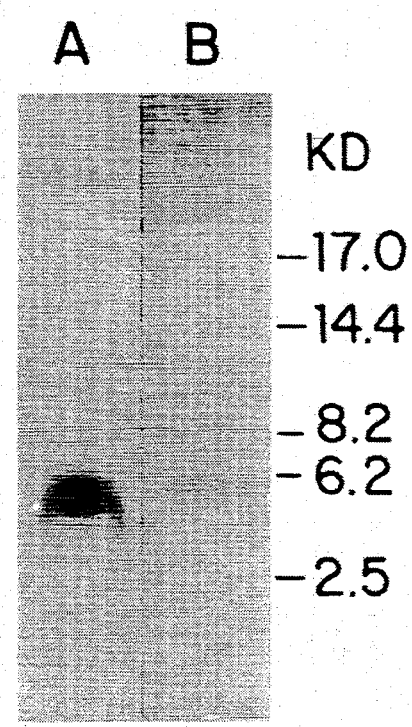

FIG. 11. Tricene-SDS-PAGE analysis of epithelin 1 and epithelin 2. An 18% minigel (0.75 mm×10 cm×7 cm) was run at room temperature at a constant voltage of 90 volts for 4.5 hr in a Bio-Rad mini-protein II electrophoresis apparatus. Dried samples were suspended in 10 μl sample buffer (50 nM Tris pH 6.8, 12% glycerol (w/v), 4% SDS, 4% mercaptoethanol (v/v) and 0.01% serva blue G.) incubated at 95° C. for five minutes and then applied on the gel. The molecular weight markers were five polypeptides from the cleavage of the horse heart myoglobin by cyanogen bromide (Sigma Chem. Co.). (A) epithelin 1; (B) epithelin 2.

Figure 12:

FIG. 12. Amino acid sequences and alignment of epithelin 1 and epithelin 2 purified from rat kidney. The standard single letter code for amino acids is used: Alanine (A); Arginine (R); Asparagine (N); Aspartic acid (D); Cysteine (C); Glutamine (Q); Glutamic acid (E); Glycine (G); Histidine (H); Isoleucine (I); Leucine (L); Lysine (K); Methionine (M); Phenylalanine (F); Proline (P); Serine (S); Threonine (T); Tryptophan (W); Tyrosine (Y); and Valine (V). The peptide sequences used to design oligonucleotide primers and probes are underlined.

Figure 13:
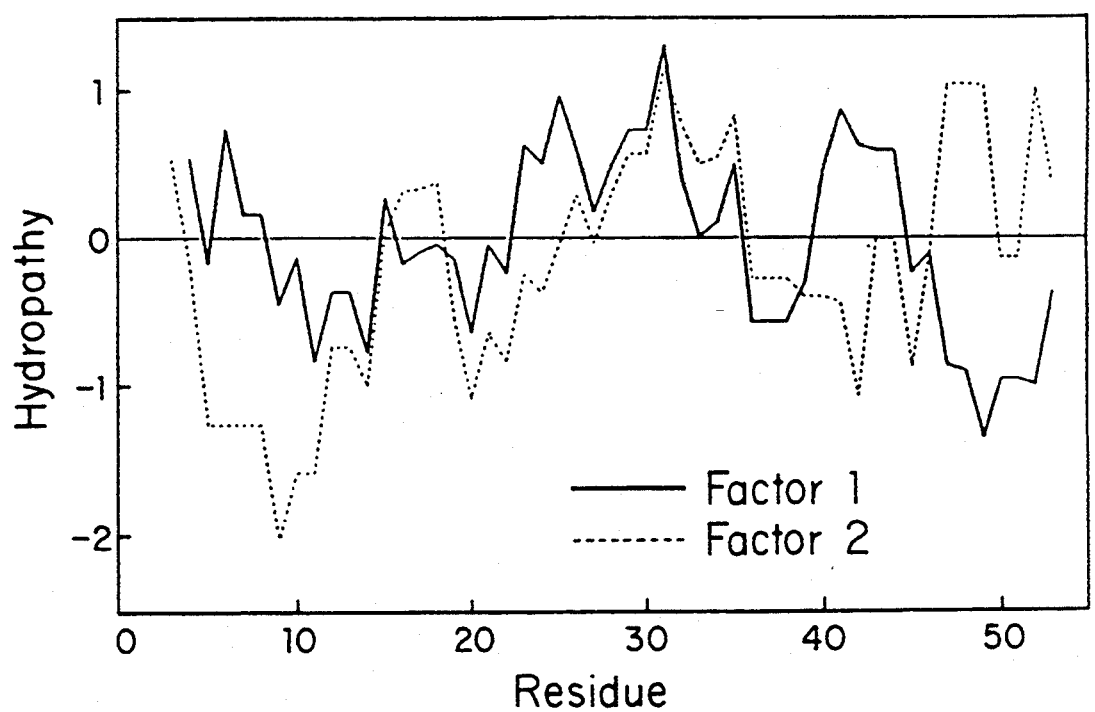

FIG. 13. Hydropathy analysis of epithelin 1 and 2 (Kyte and Doolittle). —, epithelin 1; . . . , epithelin 2.

Figure 14:
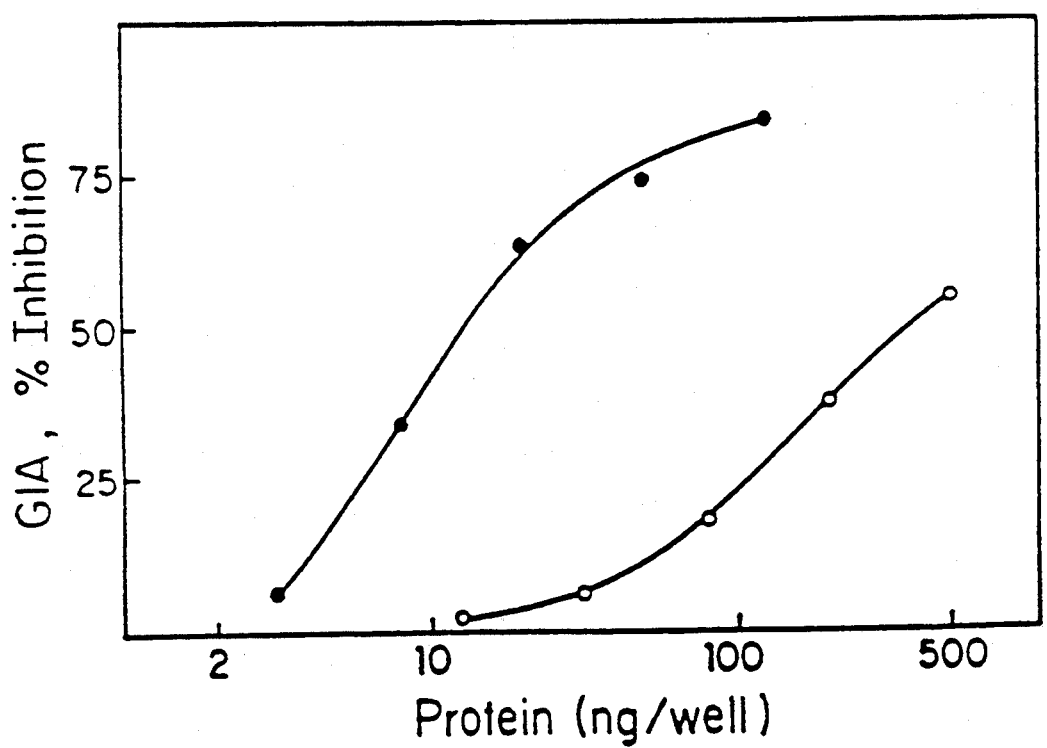

FIG. 14. Dose response curve of epithelin 1 and epithelin 2 on the inhibition of $^{125}$I-deoxyuridine incorporation into DNA of A431 cells. ●, epithelin 1; ○, epithelin 2.

Figure 15A:
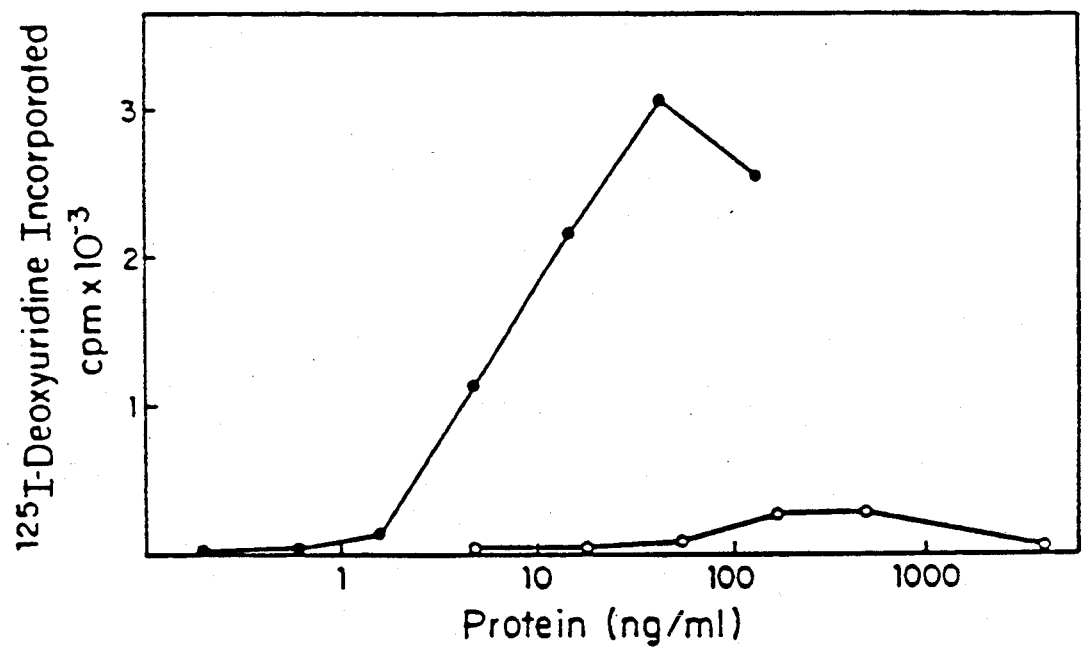

FIG. 15. (A) Effect of epithelin 1 and epithelin 2 on the stimulation of $^{125}$I-deoxyuridine incorporation into DNA of the murine keratinocyte cell line Balb/MK. 2,000–4,000 cells were plated per well in 96 well plates in low-calcium medium containing 5% dialyzed FBS. Then GSA assays were performed as described in Section 6.2., infra. ●, epithelin 1; ○, epithelin 2. (B) Effect of various concentrations of epithelin 2 on epithelin 1 (20 ng/ml) elicited incorporation of $^{125}$I-deoxyuridine into DNA of Balb/MK cells.

Figure 16A:
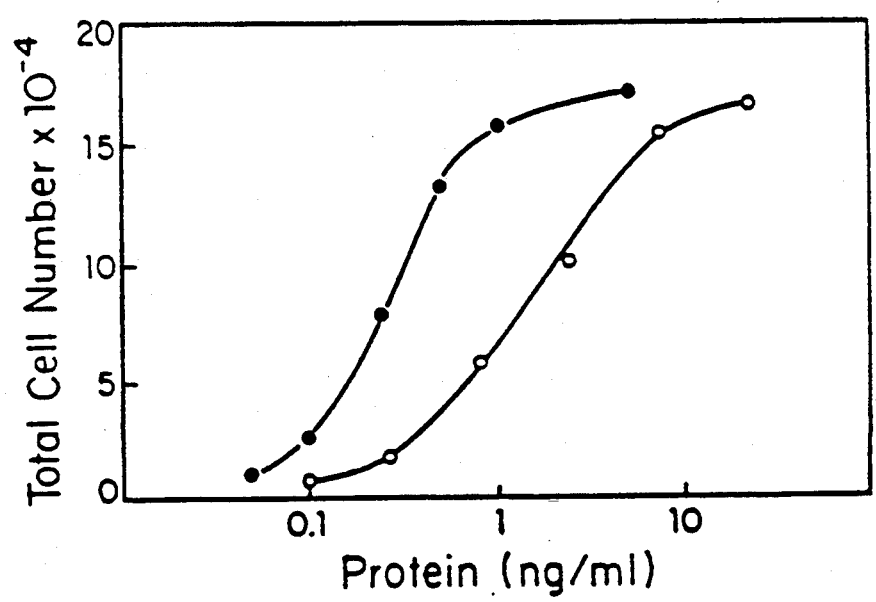
Figure 16B:
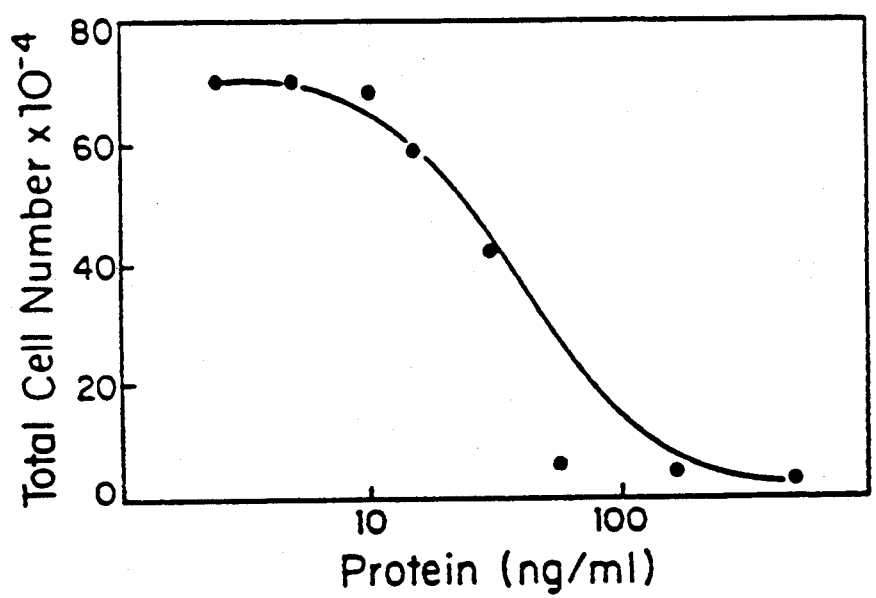

FIG. 16. (A) Effect of epithelin 1 and epidermal growth factor (EGF) on the growth of Balb/MK cells. Assays were performed as described in Section 6.2., infra. ●, epithelin 1; ○, EGF (B) Effect of various concentrations of epithelin 2 on the epithelin 1 (20 ng/ml) induced growth of murine keratinocytes.

Figure 17:
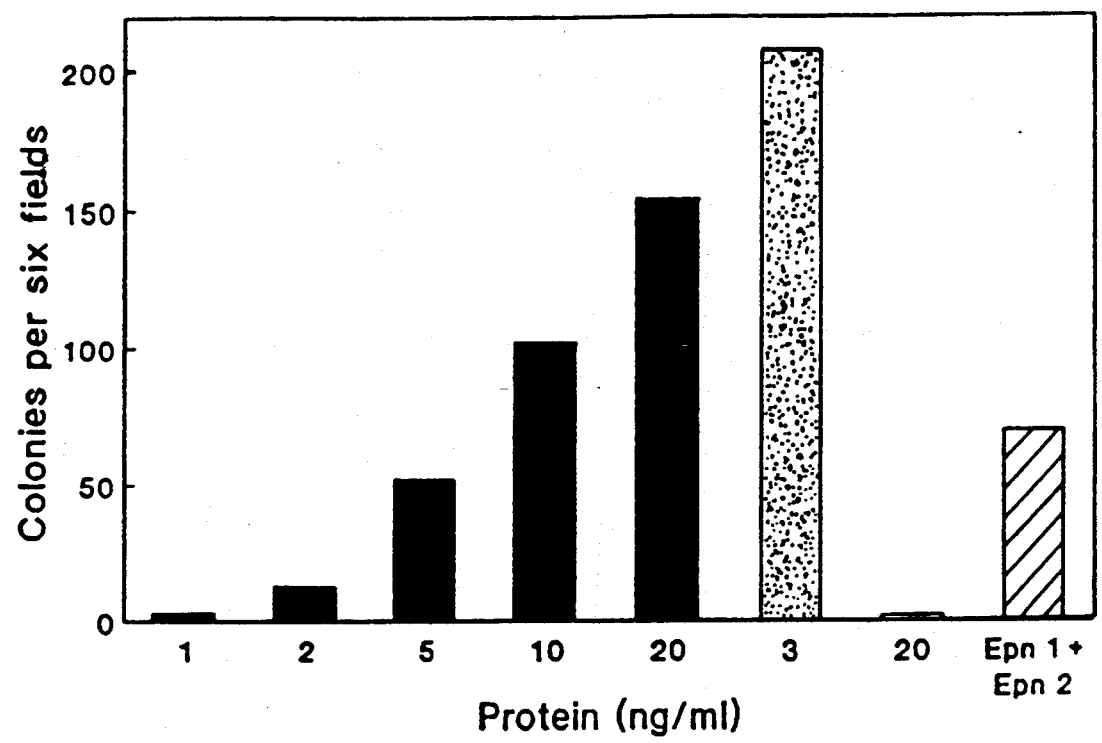

FIG. 17. Effect of epithelin 1 and 2 on NRK-SA6 cell colony formation in soft agar in the presence of TFGβ (1 ng/ml). The colony formation assay used is described in Section 6.2.3, infra. Solid bars, epithelin 1; stippled bar, epidermal growth factor; open bar, epithelin 2; hatched bar, 20 ng/ml epithelin 1 plus 500 ng/ml epithelin 2.

Figure 18:
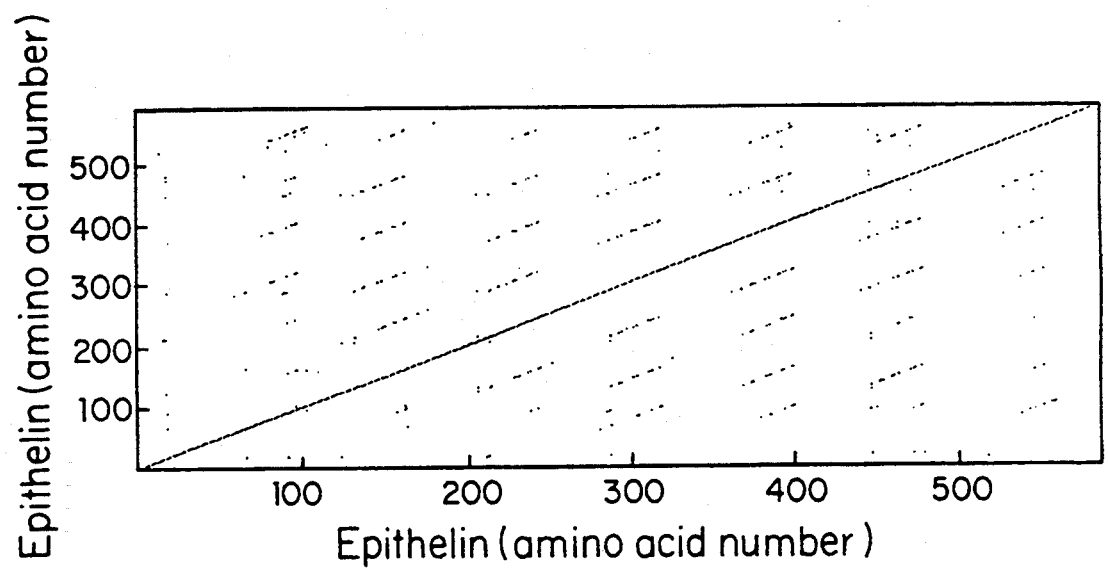

FIG. 18. Dot matrix alignment of the 589 amino acid rat epithelin precursor (SEQ ID NO: 2) compared against itself. Each point represents a stretch of five out of ten identical residues.

FIG. 19. (A) Composite secondary structure analysis of rat epithelin precursor (SEQ ID NO: 2). (B) Hydropathy of rat epithelin precursor (SEQ ID NO: 2).

FIG. 20. (A) Protein sequence comparison between the human, rat, and mouse epithelin precursor deduced from cDNA clones (SEQ ID NOS: 3, 1, and 5, respectively). Sequences are displayed using the single-letter code with identical residues denoted with dots. Gaps were introduced for optimal alignment and are shown by a dash. The predicted rat epithelin signal sequence is underlined and the seven cysteine-rich motifs are boxed. Each sequence represents a consensus based on cDNA and PCR clones isolated from human, rat, or mouse kidney RNA. Arrows mark the boundaries of a 234 bp exon, a region absent in one rat cDNA clones. (B) Amino acid sequences of rat, mouse, and human epithelins (SEQ ID NOS: 2, 6, and 4, respectively). (C) Consensus cysteine motif conserved among the epithelins. (D) Alignment of the C-terminal domain (amino acids 254–315) of a tomato (*Lycopersicon esculentum*) thiol protease with epithelin 1 and 2.

Figure 21:
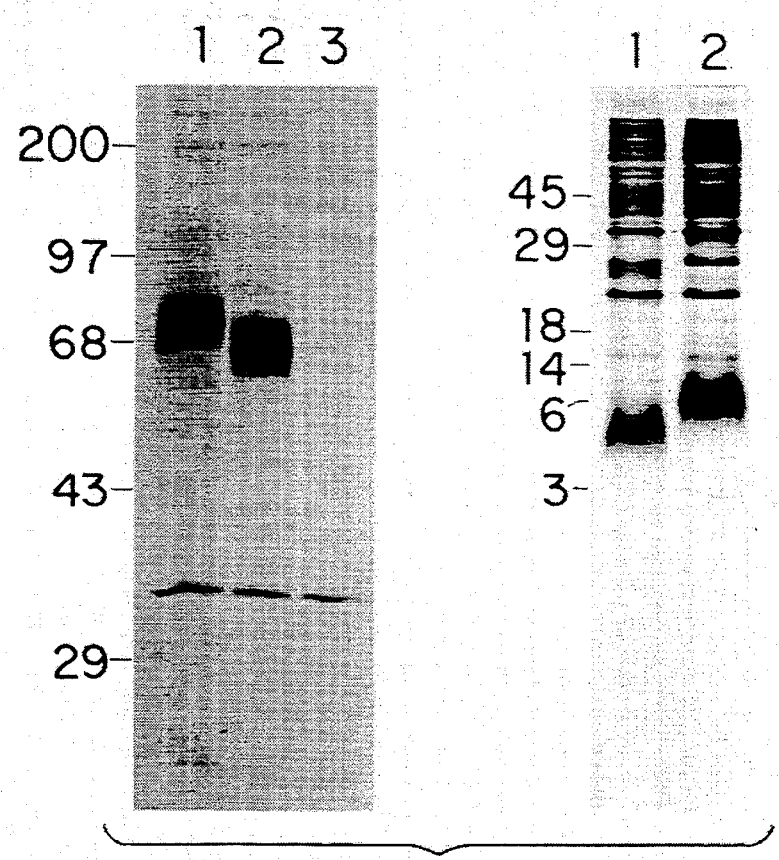

FIG. 21. Expression of recombinant epithelin in COS cells. (A) $^{35}$S-cysteine labeled supernatants from COS cells transfected with the following cDM8-based expression constructs: lane 1, crEPN1.6 containing the complete rat epithelin coding region; lane 2, crEPN1.4, containing a rat epithelin cDNA isoform lacking a 234 bp exon; lane 3, mock-transfected control. (B) $^{35}$S-cysteine labeled supernatants from COS cells transfected with the following cDM8 expression constructs: lane 1, c$\beta$rEPN1, containing a simian TGF-$\beta$1 signal sequence preceding the coding region of mature rat epithelin 1; lane 2, c$\beta$rEPN2, a similar plasmid based on rat epithelin 2.

Figure 22:
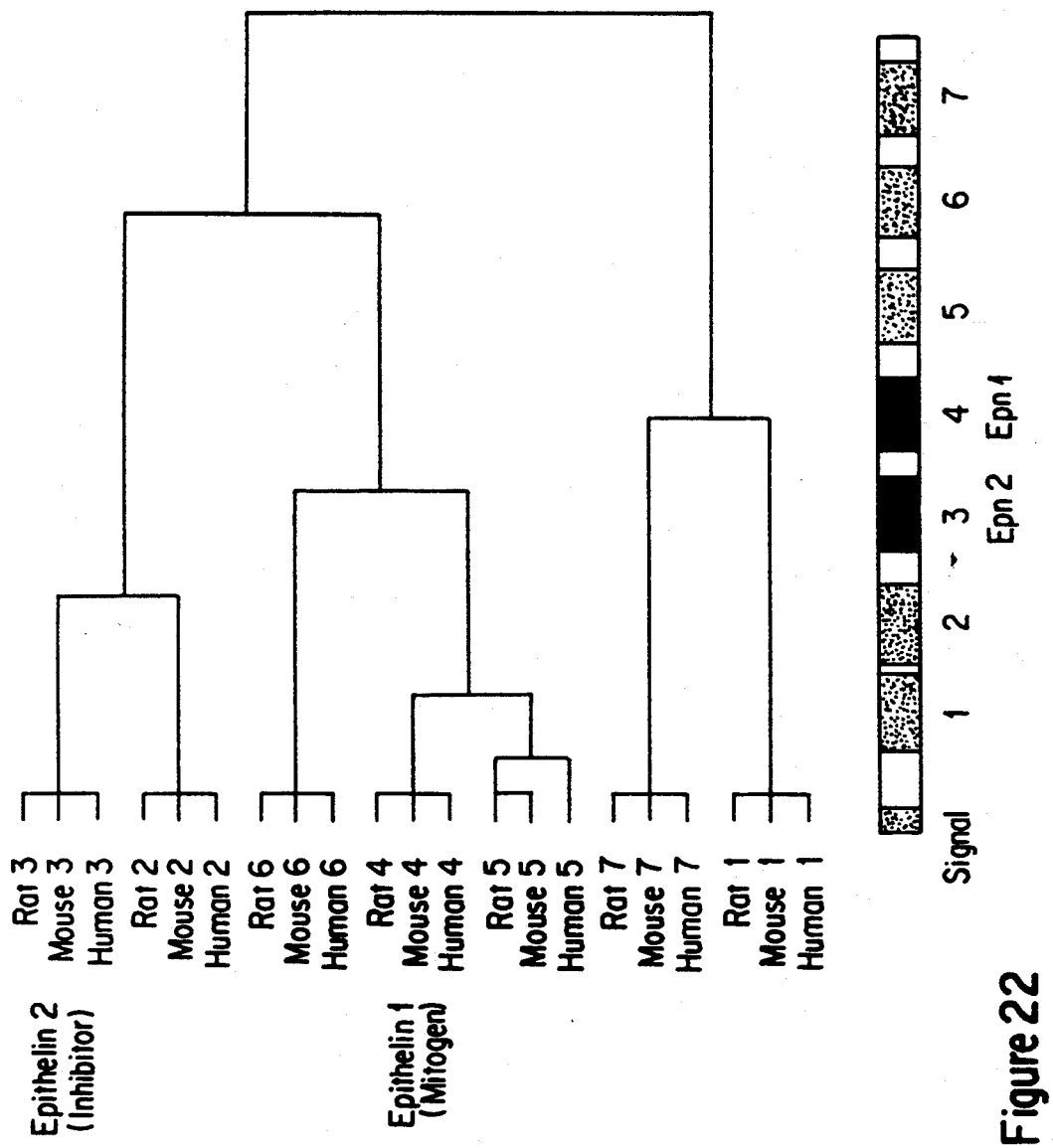

FIG. 22. Dendrogram representation of a cluster analysis between the epithelin cysteine-rich motifs from rat, mouse, and human sources. Below is a diagram of the epithelin precursor showing the position of the 7 motifs within the precursor. The 28 cysteine-rich motifs were aligned on PCGENE (Intelligenetics, Inc. Mountain View, Calif.) using the CLUSTAL multiple alignment program. The pairwise similarity scores were transformed into a difference matrix which was analyzed using the Ward's method of cluster analysis (SPSS/PC+, Chicago, Ill.). This method uses squared Euclidean distances to place branch points.

5. DETAILED DESCRIPTION OF THE INVENTION

The present invention is directed to a novel family of growth regulatory proteins termed "epithelins". The epithelins appear to comprise several distinct members sharing significant structural homology. Two members of the epithelin family, epithelin 1 and epithelin 2, have been purified from natural sources, and cDNAs encoding these and several other members of the epithelin family have been isolated from rat, human, bovine, murine and chicken, among other cell sources.

More particularly, the invention is directed to each and every member of the epithelin family, epithelin derivatives and analogues, epithelin-encoding nucleic acid molecules (e.g., cDNAs, genomic DNAs, RNAs, anti-sense RNAs, etc.), traditional and recombinant DNA based methods for the production of epithelins, recombinant epithelin expression vectors, and diagnostic and/or therapeutic uses of mature and precursor epithelins, epithelin-encoding nucleic acid molecules, anti-epithelin antibodies and epithelin receptor(s).

5.1. Production of Epithelins

The individual epithelins may be produced by several general approaches, including isolation from natural sources, solid phase peptide synthesis, and recombinant DNA technology.

5.1.1. Isolation and Purification of Epithelins from Natural Cell Sources

Applicants' DNA cloning efforts have revealed that messenger RNAs encoding the various epithelins are expressed in a number of different cell types representing a broad species range. Therefore, applicants anticipate that the individual members of the epithelin family may be isolated from a wide variety of organs, tissues, and/or other cell sources. The epithelins may be separated from each other and purified from such cell sources by using various separation and purification techniques known in the art, including but not limited to chromatographic techniques (e.g., reversed phase liquid, gel permeation, liquid exchange, ion exchange, size exclusion, and affinity chromatography), centrifugation, electrophoretic procedures, differential solubility, etc.

In a specific embodiment of the invention, described more fully by way of example in Section 6., infra, two members of the epithelin family (epithelins 1 and 2) are isolated from rat kidney tissue and subsequently purified to apparent homogeneity using, inter alia, a combination of gel permeation and reversed phase high performance liquid chromatographies (HPLC). Epithelins 1 and 2 purified in this manner are single chain polypeptides comprising 56 and 57 amino acid residues, respectively, and share significant structural characteristics. Functionally, epithelin 1 appears to be a true bifunctional growth modulator, capable of stimulating and inhibiting cell growth. Epithelin 2 appears functionally distinct inasmuch as it specifically antagonizes the cell growth stimulatory activity induced by epithelin 1. Like epithelin 1, though generally to a lesser degree, epithelin 2 is also capable of inhibiting cell growth. The functional, structural, physical and other properties of epithelin 1 and epithelin 2 have been determined and are described in Section 6.4., infra. The six-step method of preparing purified epithelin 1 and epithelin 2 described in Section 6., infra, and/or modifications thereof, may also be used to isolate other members of the epithelin family.

5.1.2. Chemical Synthesis of Epithelins

The individual members of the epithelin family may be produced using chemical methods to synthesize the corresponding amino acid sequences in whole or in part. For example, epithelins may be synthesized by solid phase techniques (Stewart and Young, *Solid Phase Peptide Synthesis*, 2nd edition, 1984). Purification and/or refolding into biologically active conformations of epithelins synthesized in this manner may be accomplished by various techniques known in the art. The amino acid compositions of the synthesized epithelins may be confirmed by amino acid analysis.

5.1.3. Synthesis of Epithelins Using Recombinant DNA Technology

Biologically active mature and precursor epithelins may be produced by the expression of epithelin-encoding DNAs in a recombinant host cell system. General techniques for the isolation of gene sequences, the construction of vectors capable of directing the synthesis of encoded proteins, and the expression and/or secretion of biologically active recombinant proteins are well known in the art.

Production of an epithelin using recombinant DNA technology may be divided into a four-step process for the purposes of description: (1) isolation or generation of the coding sequence (gene) for a precursor or mature form of the epithelin; (2) construction of an expression vector capable of directing the synthesis of the desired epithelin; (3) transfection or transformation of appropriate host cells capable of replicating and expressing the epithelin gene and/or processing the gene product to produce the desired epithelin; and (4) identification and purification of the desired epithelin product.

The cloning of a rat epithelin precursor, its expression, and the expression of mature rat epithelin 1 and 2 are described by the examples presented in Section 7., et seq, infra.

5.1.3.1. Isolation or Generation of Epithelin Genes

The nucleotide coding sequences of the various individual epithelins, or functional equivalents thereof, may be used to construct recombinant expression vectors which will direct the expression of the desired epithelin product. Epithelin-encoding nucleotide sequences may be obtained from a variety of cell sources which produce epithelin-like activities or which express epithelin-encoding mRNA. Applicants have identified a number of suitable human and murine tissue sources in this regard, including but not limited to placenta, colon, kidney, testes, adrenal, breast, ovary, duodenum, thymus, and lung tissues.

Epithelin coding sequences may be obtained by cDNA cloning from RNA isolated and purified from such cell sources or by genomic cloning. Either cDNA or genomic libraries of clones may be prepared using techniques well known in the art and may be screened for particular epithelin-encoding DNAs with nucleotide probes designed from the known amino acid sequence of epithelin 1 or epithelin 2 and/or which are substantially complementary to any portion of the epithelin gene. Full length clones, i.e., those containing the entire coding region of the precursor or mature epithelin desired may be selected for constructing expression vectors.

Alternatively, epithelin-encoding DNAs may be synthesized in whole or in part by chemical synthesis using techniques standard in the art.

Due to the inherent degeneracy of nucleotide coding sequences, other DNA sequences which encode substantially the same or a functionally equivalent amino acid sequence may be used in the practice of the methods of the invention. Such alterations of epithelin nucleotide sequences include deletions, additions or substitutions of different nucleotides resulting in a sequence that encodes the same or a functionally equivalent gene product. The gene product may contain deletions, additions or substitutions of amino acid residues within the sequence which result in silent changes thus producing a bioactive product. Such amino acid substitutions may be made on the basis of similarity in polarity, charge, solubility, hydrophobicity, hydrophilicity and/or the amphipathic nature of the resides involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine; glycine, alanine; asparagine, glutamine; serine, threonine; phenylalanine, tyrosine.

5.1.3.2. Construction of Epithelin Expression Vectors

In order to express biologically active, mature or precursor forms of the various epithelins, an expression vector/host system should be chosen which provides not only for high levels of transcription and translation but for the correct processing of the gene product. This may be especially important when employing the entire coding sequence of an epithelin precursor in the expression constructs since the mature forms of the epithelins appear to be derived from larger precursors via cellular processing events.

A variety of animal/host expression vector systems (i.e., vectors which contain the necessary elements for directing the replication, transcription and translation of epithelin coding sequences in an appropriate host cell) may be utilized equally well by the skilled artisan. These include, but are not limited to, virus expression vector/mammalian host cell systems (e.g., cytomegalovirus, vaccinia virus, adenovirus, and the like); insect virus expression vector/insect cell systems (e.g., baculovirus); or nonviral promoter expression systems derived from the genomes of mammalian cells (e.g., the mouse metallothionine promoter). Appropriate host cells include but are not limited to mammilian cells. For example, transient expression of mammalian proteins may be achieved using a COS cell host, while stable expression may be achieved using a CHO cell host.

The expression elements of these vectors vary in their strength and specificities. Depending on the host/vector system utilized, any one of a number of suitable transcription and translation elements may be used. For instance, when cloning in mammalian cell systems, promoters isolated from the genome of mammalian cells, (e.g. mouse metallothionine promoter) or from viruses that grow in these cells, (e.g. vaccinia virus 7.5K promoter or Moloney murine sarcoma virus long terminal repeat) may be used. Promoters produced by recombinant DNA or synthetic techniques may also be used to provide for transcription of the inserted sequences.

Specific initiation signals are also required for sufficient translation of inserted protein coding sequences. These signals include the ATG initiation codon and adjacent sequences. In cases where an entire epithelin gene including its own initiation codon and adjacent sequences are inserted into the appropriate expression vectors, no additional translational control signals may be needed. However, in cases where only a portion of the coding sequence is inserted, exogenous translational control signals, including the ATG initiation codon must be provided. Furthermore, the initiation codon must be in phase with the reading frame of the epithelin coding sequences to ensure translation of the entire insert. These exogenous translational control signals and initiation codons can be of a variety of origins, both natural and synthetic. The efficiency of expression may be enhanced by the inclusion of transcription attenuation sequences, enhancer elements, etc.

Any of the methods previously described for the insertion of DNA fragments into a vector may be used to construct expression vectors containing the epithelin gene of interest and appropriate transcriptional/translational control signals. These methods may include in vitro recombinant DNA techniques, synthetic techniques and in vivo recombinations.

For example, in cases where an adenovirus is used as an expression vector, an epithelin coding sequence may be ligated to an adenoviris transcription/translation control complex, e.g., the late promoter and tripartite leader sequence. This chimeric gene may then be inserted in the adenovirus genome by in vitro or in vivo recombination. Insertion in a non-essential region of the viral genome that is viable and capable of expressing the epithelin in infected hosts. Similarly, the vaccinia 7.5K promoter may be used.

An alternative expression system which could be used to express epithelins is an insect system. In one such system, *Autographa californica* nuclear polyhedrosis virus (AcNPV) is used as a vector to express foreign genes. The virus grows in *Spodoptera frugiperda* cells. An epithelin coding sequence may be cloned into nonessential regions (for example the polyhedrin gene) of the virus and placed under control of an AcNPV promoter (for example the polyhedrin promoter). Successful insertion of an epithelin coding sequence will result in inactivation of the polyhedrin gene and production of non-occluded recombinant virus (i.e., virus lacking the proteinaceous coat encoded by the polyhedrin gene). These recombinant viruses are then used to infect *Spodoptera frugiperda* cells in which the inserted gene is expressed.

Retroviral vectors prepared in amphotropic packaging cell lines permit high efficiency expression in numerous cell types. This method allows one to assess cell-type specific processing, regulation or function of the inserted protein coding sequence.

In addition, a host cell strain may be chosen which modulates the expression of the inserted sequences, or modifies and processes the gene product in the fashion desired. Expression from certain promoters can be elevated in the presence of certain inducers, (e.g. zinc and cadmium ions for metallothionein promoters). Therefore, expression of the genetically engineered epithelins may be controlled. This is important if the protein product of the cloned foreign gene is lethal to the host cell. Furthermore, modifications (e.g. glycosylation) and processing (e.g., cleavage) of protein products are important for the function of the protein. Different host cells have characteristic and specific mechanisms for the post-translational processing and modification of proteins. Appropriate cell lines or host systems can be chosen to ensure the correct modification and processing of the expressed foreign protein.

5.1.3.3. Identification of Transfectants or Transformants Expressing Epithelin Gene Products The host cells which contain the recombinant coding sequence and which express the biologically active, mature product may be identified by at least four general approaches (a) DNA-DNA, DNA-RNA or RNA-antisense RNA hybridiation; (b) the presence or absence of "marker" gene functions; (c) assessing the level of transcription as measured by the expression of epithelin mRNA transcripts in the host cell; and (d) detection of the mature gene product as measured by immunoassay and, ultimately, by its biological activities.

In the first approach, the presence of epithelin coding sequences inserted into expression vectors can be detected by DNA-DNA hybridization using probes comprising nucleotide sequences that are homologous to epithelin coding sequences.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if an epithelin coding sequence is inserted within a marker gene sequence of the vector, recombinants containing that coding sequence can be identified by the absence of the marker gene function. Alternatively, a marker gene can be placed in tandem with the epithelin sequence under the control of the same or different promoter used to control the expression of the epithelin coding sequence. Expression of the marker in response to induction or selection indicates expression of the epithelin coding sequence.

In the third approach, transcriptional activity for an epithelin coding region can be assessed by hybridization assays. For example, polyadenylated RNA can be isolated and analyzed by Northern blot using a probe homologous to the appropriate epithelin coding sequence or particular portions thereof. Alternatively, total nucleic acids of the host cell may be extracted and assayed for hybridization to such probes.

In the fourth approach, the expression of the mature protein product can be assessed immunologically, for example by Western blots, immunoassays such as radioimmunoprecipitation, enzyme-linked immunoassays and the like. The ultimate test of the success of the expression system, however, involves the detection of the biologically active epithelin gene product. Where the host cell secretes the gene product, cell free media obtained from cultured transfectant host cells is assayed for epithelin activity. Where the gene product is not secreted, cell lysates may be assayed for such activity. In either case, biological assays such as the growth inhibition and stimulation assays described herein or the like may be used.

5.1.4. Epithelin Derivatives, Analogs and Peptides

The production and use of derivatives, analogues, and peptides related to the epithelins are also envisioned and are within the scope of the invention. Such derivatives, analogues, and peptides which exhibit growth modulatory activity may, like the various epithelins, find applications in the diagnosis, prognosis, and treatment of a wide variety of neoplasias and other growth related diseases. Such derivatives, analogues, or peptides may have enhanced or diminished biological activities in comparison to native epithelins and/or may expand or limit epithelin growth inhibitory activity (GIA)-susceptible cell range and still be within the scope of the invention. Similarly, the production and use of derivatives, analogues, and peptides related to epithelins which exhibit enhanced or diminished growth stimulatory activity (GSA) and/or which expand or limit the range of cells responsive to epithelin GSA may find useful applications including, but not limited to, the treatment of wounds and burns.

Epithelin-related derivatives, analogues, and peptides of the invention may be produced by a variety of means known in the art. Procedures and manipulations at the genetic and protein levels are within the scope of the invention.

At the protein level, numerous chemical modifications could be used to produce epithelin-like derivatives, analogues, or peptides by techniques known in the art, including but not limited to acetylation, formylation, oxidation, specific chemical cleavage by endopeptidases (e.g. cyanogen bromide, trypsin, chymotrypsin, V8 protease, and the like) or exopeptidases, etc.

5.2. Anti-epithelin Antibodies

Also within the scope of the invention is the production of polyclonal and monoclonal antibodies which recognize epithelins or related proteins.

Various procedures known in the art may be used for the production of polyclonal antibodies to epitopes of epithelins. For the production of antibodies, various host animals can be immunized by injection with an epithelin, or a synthetic epithelin peptide, including but not limited to rabbits, mice, rats, etc. Various adjuvants may be used to increase the immunological response, depending on the host species, including but not limited to Freund's (complete and incomplete), mineral gels (such as aluminum hydroxide), surface active substances (such as lysolecithin), pluronic polyols, polyanions, oil emulsions, keyhole limpet hemocyanins, dinitrophenol, and potentially useful human adjuvants such as BCG (bacille Calmette-Guerin) and *Corynebacterium parvum*.

A monoclonal antibody to an epitope of an epithelin can be prepared by using any technique which provides for the production of antibody molecules by continuous cell lines in culture. These include but are not limited to the hybridoma technique originally described by Kohler and Milstein (1975, Nature 256, 495–497), and the more recent human B-cell hybridoma technique (Kosbor et al., 1983, Immunology Today 4:72) and EBV-hybridoma technique (Cole et al., 1985, Monoclonal Antibodies and Cancer Therapy, Alan R. Liss, Inc., pp. 77–96).

Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the two Fab fragments which can be generated by treating the antibody molecule with papain and a reducing agent.

Antibodies to epithelins may find use in the qualitative detection of mature epithelins and their precursor and subcomponent forms, in the affinity purification of epithelin proteins, and in the elucidation of epithelin biosynthesis, metabolism and function. Antibodies to epithelins may also be useful as diagnostic and therapeutic agents.

5.3. Biological Profile of the Epithelins

Applicants' initial cDNA cloning efforts indicate that the epithelin family of growth modulatory proteins is comprised of several structurally similar members. Moreover, it appears that epithelin-encoding mRNA is expressed in several tissue types over a broad range of chordates. Applicants' initial data regarding the structure of epithelin genes from these various chordate sources suggests that the epithelin gene has been in place and has remained remarkably constant for at least 250 million years. The various epithelins appear to be single chain low molecular weight proteins. None of the sequences obtained for the epithelins are significantly homologous to any previously known protein. Interestingly, several of the epithelins contain a region homologous with the active site of phospholipase A2.

Epithelin 1 and epithelin 2 purified from rat kidney tissue are proteins of 56 and 57 amino acids, respectively, sharing 47% amino acid sequence homology and 12 identically positioned cysteine residues. Thus, about one-fifth of the amino acids of both epithelins are cysteines. The positioning of these 12 cysteine residues suggests that, through the formation of disulfide linkages between them, the pattern directs the formation of a "cysteine cage" at the tertiary structural level, perhaps not unlike zinc finger structures. Applicants are not aware of any other protein having this particular, or a closely related, cysteine pattern. This unique cysteine pattern is observed not only in the primary structures of purified epithelins 1 and 2, but also in the structures deduced from the sequences of several epithelin-encoding cDNAs and PCR clones. It appears that this unique cysteine pattern is therefore a distinguishing characteristic of the epithelin family members, and likely plays an important functional role. In addition, some 15 other amino acids are conserved between these two purified epithelins.

Figure 19A:
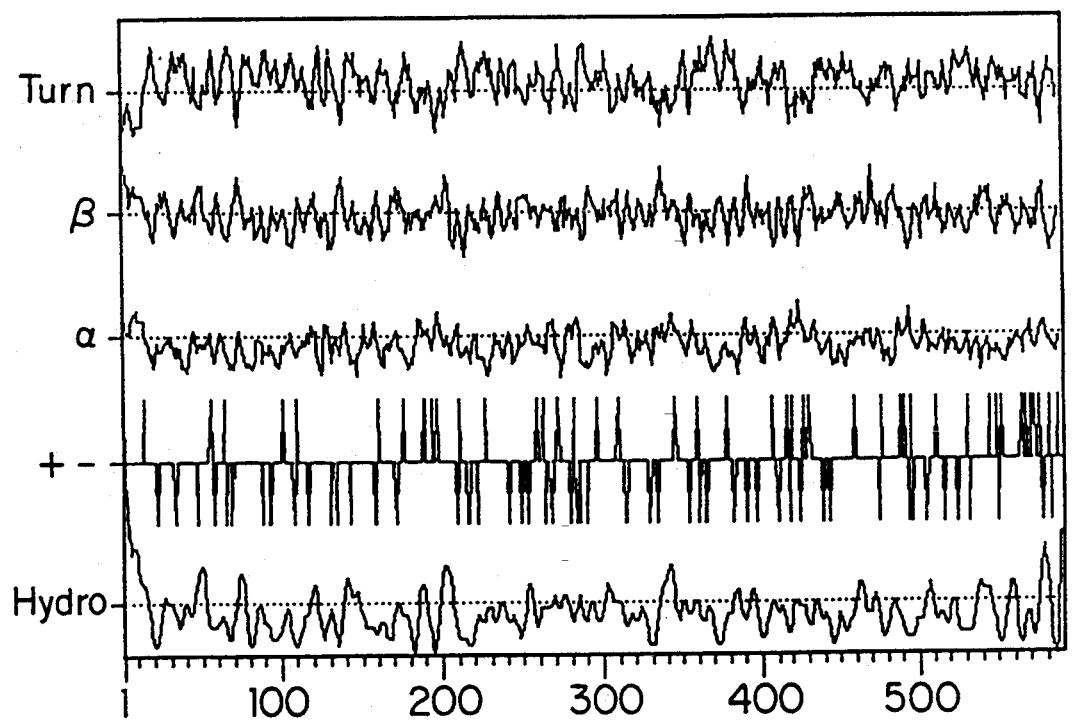
Figure 19B:
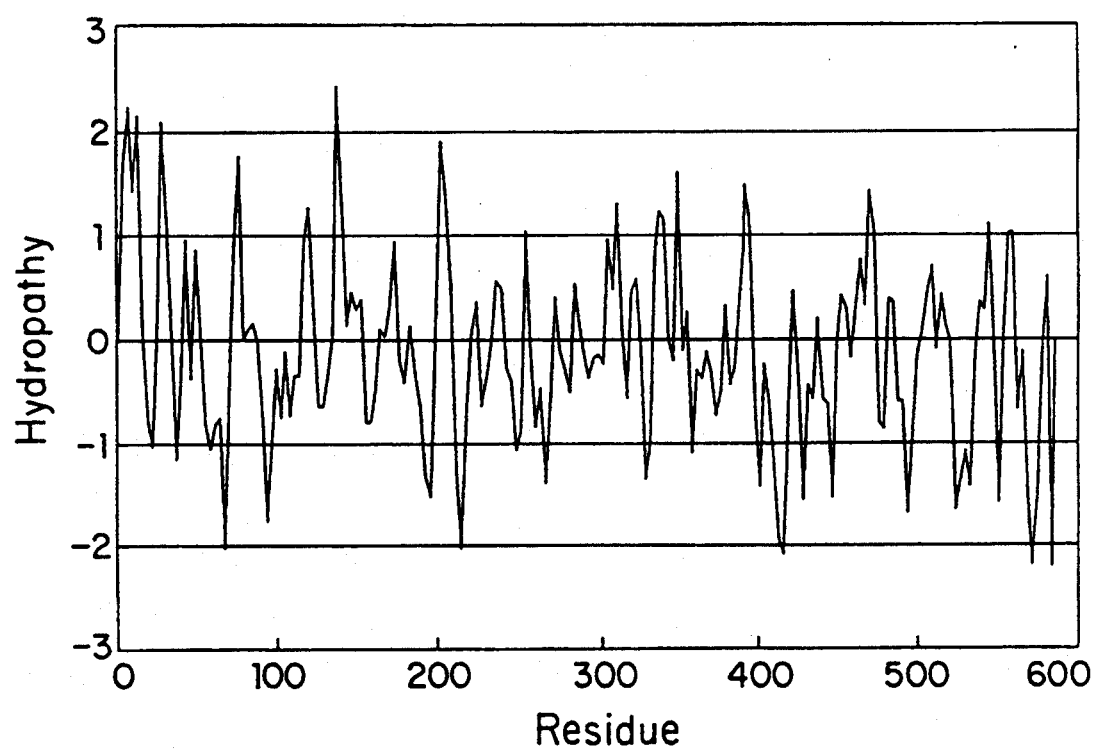

A cDNA encoding the complete rat epithelin precursor has been isolated and its nucleotide and deduced amino acid sequences determined, as shown in (SEQ ID NO: 1). The rat epithelin precursor comprises a polypeptide of 589 amino acid residues, the amino-terminal 17 residues of which comprise its signal peptide. It appears that at least seven complete and distinct epithelin species are encoded within the rat epithelin precursor gene. The high level of sequence homology between the epithelins encoded by the rat epithelin precursor cDNA can be visualized by the 7.5-fold internal homology generated upon comparison of the rat epithelin precursor sequence to itself, as illustrated in FIG. 18. Composite secondary structure and hydropathy analyses of the rat epithelin precursor are shown in FIG. 19A and FIG. 19B, respectively. Amino acid sequence alignments between the rat, mouse and human epithelin precursors (SEQ ID NOS: 2, 6, and 4, respectively) are shown in FIG. 20A.

Applicants have also isolated the complete human, mouse and rat epithelin precursor DNA sequences (SEQ ID NOS: 1, 5, and 3, respectively). A composite alignment of these epithelin sequences is illustrated in FIG. 20A. In addition, a number of PCR clones encoding various epithelins of bovine and avian origin have been obtained, and the bovine and avian epithelin precursor structures partially determined. (SEQ ID NOS: 7 and 8 (bovine) and SEQ ID NOS and 10 (chicken)). Analysis of the various sequences indicates that the epithelins share, to somewhat different degrees, a distinct structural characteristic defined by the highly conserved cysteine motif (consensus) shown in FIG. 20C. While this consensus sequence appears to be generally conserved among the epithelins, a cysteine core motif of "CCx$_8$CCx$_6$CCx$_5$CC" is almost completely conserved in all epithelin species examined to date, regardless of origin. Exceptions include the first full repeat of the rat epithelin precursor (SEQ ID NO: 2) where Cysteine to serine substitutions are present and the motif is "SCx$_9$CCx$_6$SCx$_5$CC". Furthermore, a histidine residue at the 25th position of the core motif also appears to be conserved among the epithelin species. Applicants believe that the core motif is a unique characteristic of all epithelins and, accordingly, intend that the present invention encompass all proteins having this structural feature. FIG. 20B shows the amino acid sequence of human, rat and mouse mature epithelins 1–7 aligned. The sequence represented by FIG. 20C is completely conserved between epithelins 2–7 in these three species. The epithelin 1 sequences diverge from this sequence only slightly.

Applicants have examined RNA from a large number of human and murine tissues and cell lines for the presence of epithelin transcripts, the results of which are sumarized in TABLE I, below.

TABLE I

DISTRIBUTION OF EPITHELIN TRANSCRIPT EXPRESSION IN VARIOUS HUMAN AND MURINE TISSUES AND CELLS

| HUMAN Strong + | Weak + | Negative (using Rat Probe) |
|---|---|---|
| Placenta | Ovary | Brain |
| Colon | Duodenum | Epidermis |
| Kidney Medulla | Thymus | Liver |
| Kidney Cortex | Lung | Pituitary |
| Testis | Kidney | Amnion |

TABLE I-continued
DISTRIBUTION OF EPITHELIN TRANSCRIPT EXPRESSION IN VARIOUS HUMAN AND MURINE TISSUES AND CELLS

| Adrenal | | Bone Marrow |
| --- | --- | --- |
| Breast | | Cerebellum |
| CRL 7386 | HBL100 | |
| Caki-1 | HEPM | MCF-7 |
| CRL 1550 | CRO 1572 | HTB27 |
| Caki-2 | HTB132 | T47D |
| HUF | 1477 | CEMA-1 |
| CCL 137 | HSB2 | |
| | U937 | Breast Ca |
| | HTB131 | Wilm's Ca |
| | BT474 | |
| | HTB36 | |

| MOUSE | | |
| --- | --- | --- |
| Strong + | Weak + | Negative |
| Fetal Intestine | Heart | NONE |
| Placenta | Ovary | |
| Kidney | Thymus | |
| | Pancreas | |
| Brain (Cortex) | Cerebellum | |
| | Lung | |
| | Embryo d15 | |
| | Embryo D6 | |
| | Liver | |
| | Colon | |
| | Duodenum | |
| | Skeletal Muscle | |
| | CCL51 | |
| | CCL51 (TPA) | |

The biological characteristics of purified epithelin 1 and epithelin 2 are described in some detail in Section 6.4, infra. Both proteins are stable after treatment with 1M acetic acid, 1M ammonium hydroxide, 6M urea, 10 mM sodium metaperiodate, and heating at 56° C. for 30 minutes. The bioactivities of both proteins are sensitive to, inter alia, proteolytic enzymes and reducing agents. It is clear that at least some disulfide linkages in the epithelin structure are essential for bioactivity. It does not appear that oligosaccharides and/or lipid moieties are essential for the activity of either epithelin 1 or 2.

Epithelin 1 and epithelin 2 exhibit growth inhibitory activity on, inter alia, human epidermoid carcinoma cells. Applicants' data suggests, however, that epithelin 1 is a more potent inhibitor of cell growth. For example, the calculated specific activity of purified epithelin 1 is nearly ten times that of epithelin 2, and epithelin 1 appears to be some 36 times more potent than epithelin 2 in inhibiting the growth of A431 cells. Moreover, in at least one cell line tested, a human colon carcinoma cell line, epithelin 2 was incapable of triggering the inhibitory effect observed with epithelin 1.

Of additional interest is the functional divergence between epithelin 1 and epithelin 2 with respect to cell growth stimulatory bioactivity. Applicants have demonstrated that epithelin 1, in addition to its growth inhibitory bioactivity, is a potent stimulator of cell growth on several cell lines, leading applicants to conclude that epithelin 1 is a true bifunctional growth modulator. In contrast, applicants' data suggests that epithelin 2 is incapable of triggering a growth stimulatory effect, at least on the cell lines tested.

Perhaps most interesting of all is applicants' further discovery that epithelin 2 specifically antagonizes the stimulatory activities exerted by epithelin 1. Although the functional interrelationship among these and/or other epithelins is not understood at the present time, it is possible that epithelin 2 may function as a control on the stimulatory activity induced by epithelin 1. Applicants speculate that an agonist/antagonist functional relationship among epithelin 1 and epithelin 2, and/or among other members of the epithelin family, may control or otherwise influence the balance between normal and unrestrained cell growth and development. In this regard, cellular homeostatis may be altered or destroyed by the loss of a critical function provided by an epithelin or epithelins involved in such an interrelationship resulting, for example, in unrestrained cell proliferation. Through the therapeutic use of epithelins, anti-epithelin antibodies, and/or epithelin receptors, cellular homeostasis may be modulated and/or restored.

The ability to express individual motifs from the epithelin precursor will assist in determining whether differential processing releases other active molecules. In order to select candidate effectors or blockers, the sequences of the cysteine-rich motifs shown in FIG. 20A were aligned and cluster analyzed. The results are represented by the dendrogram in FIG. 22. In all cases, the least dissimilar motif is found at the same position within the precursor of the other 2 species. Based on these findings, it is proposed that the primordial epithelin gene underwent a seven-fold replication prior to the divergence of rodents and humans. This analysis also shows that the fifth repeat of the epithelin precursor is most similar to epithelin 1, and is a candidate for having growth stimulatory activity. In addition, the second repeat is most similar to epithelin 2, and is a candidate antagonist of the mitogenic effects of epithelin 1.

The epithelin gene has several intriguing features. The gene's ubiquitous expression suggests it plays a role in the maintenance of normal epithelial cell growth, in contrast to previously described molecules that have a more restricted distribution. The highly repetitive and cysteine-rich structure of the epithelin precursor defines a novel and evolutionarily conserved motif. Furthermore, at least two of these motifs can be proteolytically processed into active growth regulators. This configuration is similar to that of proopiomelanocortin (POMC), a prohormone that is processed in a tissue-specific manner to release a variety of bioactive peptides. (Smith and Funder, 1988, Endocr. Rev. 9:159–79).

The opposing activities of epithelin 1 and 2 on the growth of epithelial cells is reminiscent of other systems where naturally occurring, structurally related molecules act as antagonists or suppressors of the parent molecule. Examples of this include; IL-1ra, an interleukin-1 receptor antagnoist (Hannum et al., 1990, Nature 343:336–40; Eisenberg et al., 1990, Nature 343:341–46); Krev-1 (Kitayama et al., 1989, Cell 56:77–84), a protein that suppresses ras induced transformation; and inhibin (Ling et al., 1985, Proc. Natl. Acad. Sci. U.S.A. 82:7217–21), a gonadal protein that opposes the biological effects of activin (Ling et al., 1986, Nature 321:779–82). Further studies to identify cellular receptors for epithelin 1 and 2 are needed to define how these molecules mediate their opposing signals. The finding that both activities are products of the same transcript is provocative. Conceivably, tissue-, spatial-, or temporally-specific processing might provide a unique means of regulating epithelial homeostasis.

5.4. Uses of the Epithelins, Epithelin-encoding Nucleic Acid Molecules, Anti-epithelin Antibodies and Epithelin Receptors Applicants envision a wide variety of uses for the compositions of the present invention, including diagnostic and/or therapeutic uses of the epithelin proteins, epithelin analogues and derivatives, epithelein-encoding nucleic acid molecules, anti-epithelin antibodies and epithelin receptors.

5.4.1. Epithelin Proteins

Epithelin proteins, analogues and derivatives, as well as compositions containing them, may be used alone or in combination with each other and/or with other biologically active growth factors, inhibitors, or immunomodulatory agents to regulate the growth and/or development of chordate cells in vivo and in vitro.

Different epithelins and epithelin compositions may be used to achieve different therapeutic objectives. In particular, given the observed functional diversity between epithelin 1 and epithelin 2, applicants envision that these two epithelins may be used for different purposes. However, notwithstanding their functional differences, both epithelin 1 and epithelin 2 may be useful as anti-tumor agents since they both demonstrate the ability to inhibit the growth of neoplastic cells, although applicants' initial data suggests that epithelin 1 may be a more powerful and/or effective tumor inhibitor. The particular combination of epithelins and/or other factors used will depend on the type of target cells involved as well as the particular objective(s) desired.

For in vivo use, the subject compositions may be administered in a variety of ways, including but not limited to, injection, infusion, topically, parenterally, etc. Administration may be in any physiologically acceptable carrier, including phosphate buffered saline, saline, sterilized water, etc. Epithelins and related molecules may also be encapsulated in liposomes and may be conjugated to antibodies which recognize and bind to tumor or cell specific antigens, thereby providing a means for "targeting" the compositions of the invention.

The epithelins may be useful in vivo for inducing terminal differentiation in tumor cells. Such cells have diverted from the ordinary course of cell differentiation characteristic of normal cells and are capable of continued proliferation. Normal cells, in contrast, differentiate into cells which are incapable, under most circumstances, of further cell division. Thus, the ability of the epithelins to reactivate normal cellular differentiation in tumors and, ultimately, to arrest continued tumor growth may find valuable use in tumor therapy regimens.

Epithelins and related derivatives, analogues, and peptides thereof may be used alone or with at least one other anti-proliferative compound, including, for example, an interferon, TFG-$\beta$, tumor necrosis factors, etc., in the treatment of neoplastic and other growth related diseases. Carcinomas may also be treated by inducing production of epithelins in the carcinoma cells.

The compounds of the invention may be used in vitro to inhibit the growth of cells or cell lines sensitive to epithelins as distinguished from cells which are not sensitive. In this way, heterogeneous mixtures or cell lines can be freed of undesirable cells, where the undesirable cells are sensitive to epithelin growth inhibitory activity. For example, the compounds of the invention may be used in vitro to eliminate malignant cells from marrow for autologous marrow transplants, and to eliminate or inhibit the proliferation of malignant cells in blood prior to reinfusion.

The most effective concentration of epithelins for inhibiting proliferation of a given cell may be determined by adding various concentrations of epithelins to the tumor cell of interest and monitoring the amount of inhibition of cell proliferation. The most effective concentration of individual inducers and/or combinations of inducers may be determined by monitoring the production of epithelins in the carcinoma cells.

Stimulation of cell growth can be induced by epithelin 1, epithelin 1-like molecules, and, perhaps, by other members of the epithelin family. A wide range of therapeutic applications based on this epithelin bioactivity are envisioned, including but not limited to wound healing and tissue remodeling. Moreover, antibodies capable of neutralizing the epithelin 1-inhibiting activity of epithelin 2 may also be useful in promoting wound healing and tissue remodeling, with or without the coadministration of epithelin 1 or epithelin 1-like molecules.

The compositions of the present invention may also find use in the treatment of human skin diseases involving the proliferation of normal cells, such as psoriasis. Although the pathogenesis of psoriasis is not known, the disease involves rapid epithelial cell proliferation and turnover. The accompanying rapid turnover of keratinocytes alters keratinization, resulting in thickened epidermis and scales characteristic of the disease. Since epithelin 1 stimulates the growth and proliferation of keratinocytes, effective therapy inhibiting this epithelin 1-induced activity may impede the onset and development of the disease. Therefore, compositions capable of inhibiting what may be endogenous or abnormally high levels of epithelin 1 in psoriasis patients may be effective in curing the disease. Applicants have demonstrated that epithelin 2 specifically inhibits the epithelin-I-induced stimulation of keratinocytes. In this regard, epithelin 2-containing compositions may be particularly useful in the treatment of psoriasis. Similarly, antibodies capable of neutralizing epithelin 1 stimulatory activity may be used to inhibit epithelin 1 activity.

Applicants also envision the use of epithelins and epithelin-like molecules for other therapeutic purposes, including but not limited to the modulation of angiogenesis, renal generation, bone resorption, immune responses, synaptic and neuronal effector functions, the arachidonic cascade, and gonadal and reproductive functions.

A number of diagnostic uses of epithelins and related molecules are envisioned. In the practice of the invention, the subject polypeptides may be joined to a label, such as a radioisotope, enzyme, fluorescer, chemiluminescer, enzyme fragment, particle, etc. Such compounds may be used to titrate the number of epithelin receptors on a cell. Identification of epithelin receptors is an indication of potential responsiveness of the cell to the biological effects of epithelins and related molecules. Epithelins, epithelin-related molecules, and/or antibodies thereto may be used in competitive assays for detection of epithelins in media, particularly in physiological media. A wide variety of diagnostic assays known in the art may be used.

The presence and levels of epithelins in body fluids and tissues may directly or inversely relate to the presence and pervasiveness of certain cancers and other growth related diseases. Assays which can detect and/or quantify epithelins may find use in diagnosis and prognosis of growth related diseases.

In addition, malignant cells expressing epithelin receptors may be detected by using labeled epithelins or epithelin-related molecules in a receptor binding assay, or by the use of antibodies to the epithelin receptor itself. Cells may be distinguished in accordance with the presence and density of epithelin receptors, thereby providing a means for predicting the susceptibility of such cells to the biological activities of epithelins.

5.4.2. Epithelin-encoding Nucleic Acid Molecules

Epithelin-encoding nucleic acid molecules or fragments thereof may be used as probes to detect and quantify mRNAs encoding epithelins. Assays which utilize nucleic acid probes to detect sequences comprising all or part of a known gene sequence are well known in the art. Epithelin mRNA levels may indicate emerging and/or existing neoplasia as well as the onset and/or progression of other human diseases including but not limited to psoriasis. Therefore, assays which can detect and quantify epithelin mRNA may provide a valuable diagnostic tool.

Anti-sense epithelin RNA molecules may be useful therapeutically to inhibit the translation of epithelin-encoding mRNAs where the therapeutic objective involves a desire to eliminate the presence of a given epithelin. Epithelin 1 anti-sense RNA, for example, could be useful as an epithelin 1 antagonizing agent in the treatment of diseases for which epithelin 1 is a causative agent. Additionally, epithelin anti-sense RNAs may be useful in elucidating epithelin functional mechanisms.

Epithelin-encoding nucleic acid molecules may be used for the production of recombinant epithelin proteins and related molecules, as separately discussed in Section 5.1.3., supra.

6. Example: Preparation of Purified Epithelin 1 and Epithelin 2 from Rat Kidney

6.1. Purification Procedures

6.1.1. Acid Ethanol Extraction

Rat kidneys were obtained from Pel-Freeze (Rogers, Ark.). Frozen rat kidneys (430 g wet weight) were suspended in 2370 ml of extraction buffer consisting of 2348 ml ethanol (98%), 19 ml of concentrated HCl, 81.5 mg phenylmethyl-sulfonyl fluoride and 2.8 ml of aprotonin (23 TIU/ml from bovine lung; Sigma Chemical Co.). The tissue was allowed to thaw at 4° C. for 4–6 hours and the mixture was homogenized in a Waring blender. The mixture was stirred at 4° C. overnight, centrifuged at 9,000 rpm in a Sorvall GS-3 rotor for 40 minutes and the supernatant carefully removed (2,200 ml). Chloroform (2,200 ml) and 220 ml of acidified water (375 ml water +7.5 ml of concentrated HCl) was added to the supernatant, the mixture stirred vigorously for approximately one hour, and allowed to stand at room temperature to separate into two phases. The upper aqueous phase was carefully removed and dialyzed against 17 liters of 0.1M acetic acid at 4° C. in No. 3 Spectropore dialysis tubing (molecular weight cut off approximately 3,000). The dialysis buffer was changed three times over a two-day period. The retenate was lyophilized and the lyophilized material (4.55 g), termed "crude extract", was stored at −20° C. until further use.

6.1.2. Preparative Gel Permeation Chromatography

A Bio-Sil TSK-250 column (21.5×600 mm) (BioRad) was attached to a high performance liquid chromatography (HPLC) system (Waters). The crude extract (25 mg/ml) was dissolved in 50% acetonitrile/water with 0.1% trifluoroacetic acid (TFA). A 3 ml aliquot of the mixture was injected and elution was performed isocratically with a mobile phase of 50% acetonitrile with 0.1% TFA. The flow rate was 4 ml/min and chart speed was set at 0.25 cm/min. Six ml fractions were collected. The chromatography was performed at room temperature. An aliquot from each fraction was evaporated and assayed in triplicate for growth inhibitory activity (GIA) on A431 human epidermoid carcinoma cells as described in Section 6.2.1., infra. (FIG. 1).

The late eluting minor peak (Fractions 25–28) contained the new activities of interest. Fractions 25–28 from 57 similar runs were pooled, concentrated and lyophilized. The lyophilized material weighed 473 mg and had a total of approximately $1.1 \times 10^5$ GIA units.

6.1.3. Reversed-phase HPLC of Preparative TSK-250 Fractions

The lyophilized fractions (Section 6.1.2., supra) were dissolved in 240 ml of 0.1% TFA in water; the mixture was centrifuged, and the supernatant was carefully removed. The final volume was about 250 ml. 125 ml of this mixture was isocratically injected onto a preparative Partisil 10 ODS-3 column (10 micron, 2.2×25 cm; Whatman) attached to a HPLC system. The flow rate was set at 4 ml/min. Once the sample had passed onto the column, the column was washed with 150 ml of 0.1% TFA in water. The linear gradient was generated between the primary solvent, 0.1% TFA in water, and the secondary solvent, acetonitrile containing 0.1% TFA. The gradient conditions were: 0 to 45% in 270 minutes and 45 to 100% in 45 minutes. 14 ml fractions were collected and aliquots of each fraction were assayed for GIA. Four broad peaks of activity were seen (FIG. 2). A second run was performed as described above. Two early eluting peaks, peak a and peak b, contained epithelin 2 and epithelin 1, respectively, and they were further purified and characterized. The further purifications of epithelin 1 and epithelin 2 are described separately below.

6.1.4. Further Purification of Epithelin 1 by Reversed-phase and Gel Permeation HPLC Fractions 55–59 (FIG. 2) from two runs were pooled and diluted twofold with 0.1% TFA in water. The mixture was isocratically injected onto a semi-preparative μ-Bondapak-C18 column (7.8×300 mm, Waters) at a flow rate of 2 ml/min at room temperature. The linear gradient conditions between primary solvent, water with 0.1% TFA, and the secondary solvent, acetonitrile with 0.1% TFA, were 0 to 18% in 1.8 minutes, 18 to 18% in 20 minutes, 18 to 34% in 240 minutes, and 34 to 100% in 10 minutes. The flow rate was 2 ml/min throughout the gradient; 7 ml fractions were collected. Aliquots were taken and assayed for GIA. Two peaks of activity were observed eluting at acetonitrile concentrations of approximately 24% and 25%, respectively (FIG. 3).

Fractions 30–34 were pooled. 45 ml of 0.1% TFA in water was added to the pooled fraction. The mixture was isocratically applied onto a μ-Bondapak-CN column (3.9×300 mm, Waters) at a flow rate of 1 ml/min at room temperature. The gradient conditions were 0 to 10% in 1 minute, 10 to 10% in 19 minutes, 10 to 30% in 200 minutes, and 30 to 100% in 7 minutes. The flow rate was 0.5 ml/min and 1.5 ml fractions were collected. Most of the activity emerged from the column at about 21.5% acetonitrile concentration (FIG. 4).

Fractions 36–43 were pooled and diluted with 0.1% TFA/$H_2O$ to a final volume of 115 ml and chromatographed exactly as described for fractions 30–34, above. Most of the activity eluted from the column in two peaks, eluting at approximately 22.5% and 23.5% acetonitrile (FIG. 5).

Figure 6A:
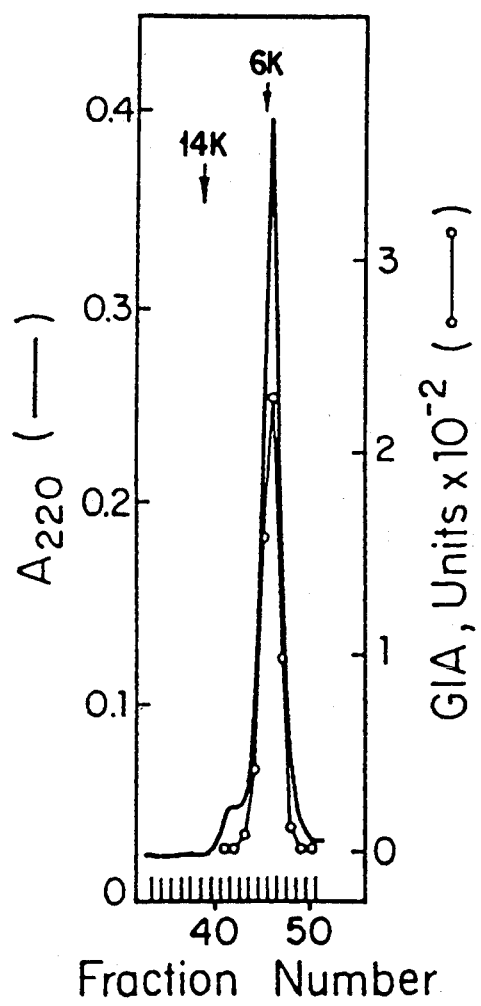
Figure 6B:
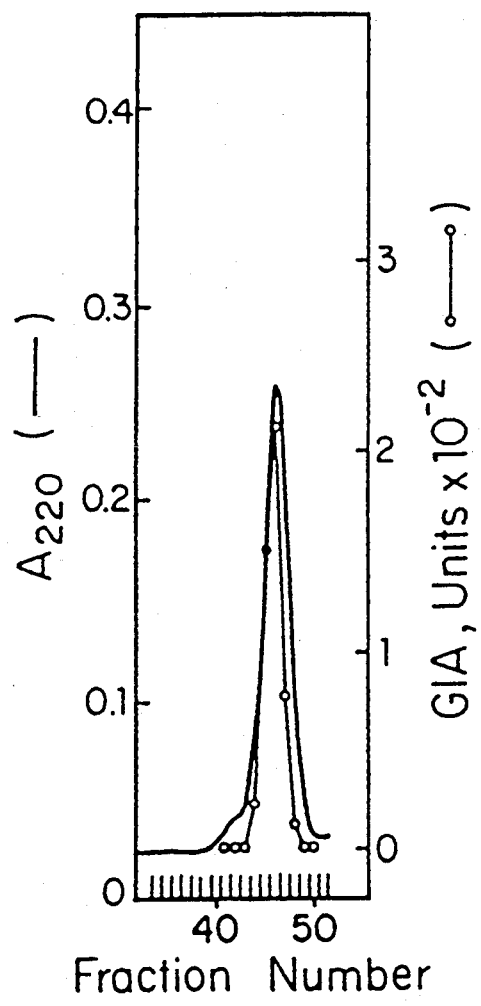

Fractions 51 and 52 (FIG. 4) were individually concentrated, using a speed-vac concentrator (Savant), to a volume of about 70 μl, to which an equal volume of acetonitrile containing 0.1% TFA was added. This 140 µl sample was injected onto two Bio-Sil TSK-250 columns (7.5×300 mm each, Bio-Rad) arranged in tandem. The elution was performed isocratically with a mobile phase of 50% acetonitrile/H₂O with 0.1% TFA at room temperature. The flow rate was 0.4 ml/min and chart speed was 0.25 cm/min; 0.4 ml fractions were collected and aliquots were assayed for GIA. The chromatographic profiles of fractions 51 and 52 are shown in FIG. 6A and FIG. 6B, respectively.

Fractions 44 and 45 (FIG. 5) were individually concentrated to 70 µl and then subjected to gel permeation chromatography as described above. The chromatographic profiles are given in FIG. 7.

6.1.5. Further Purification of Epithelin 2 by Reversed-phase and Gel Permeation HPLC Fractions 50–54 (FIG. 2) from two runs were pooled and diluted twofold with 0.1% TFA/H₂O. The mixture was applied onto a semi-preparative µ-Bondapak-C18 column (7.8×30 mm, Waters) at a flow rate of 2 ml/min. The linear gradient conditions between primary solvent, water with 0.1% TFA, and the secondary solvent, acetonitrile with 0.1% TFA, were 0 to 18% in 1.8 minutes, 18 to 18% in 20 minutes, 18 to 34% in 240 minutes, and 34 to 100% in 10 minutes. The flow rate was 2 ml/min throughout the gradient; 7 ml fractions were collected. Aliquots were taken and assayed for GIA. The chromatographic profile is shown in FIG. 8. The major peak of activity eluted at approximately 20.5% acetonitrile concentration.

Fractions 18–23 were pooled and diluted with 0.1% TFA/H₂O to a final volume of 110 ml. The mixture was applied onto a µ-Bondapak-CN column (3.9×300 mm, Waters) at a flow rate of 1 ml/min at room temperature. The gradient conditions were 0 to 10% in 1 minute, 10 to 10% in 19 minutes, 10 to 30% in 200 minutes, and 30 to 100% in 7 minutes. The flow rate was 0.5 ml/min; 1.5 ml fractions were collected. The activity emerged from the column at an acetonitrile concentration of about 18% (FIG. 9).

Fractions 36–38 (FIG. 8) were individually concentrated to approximately 70 µl, to which an equal volume of acetonitrile containing 0.1% TFA was added. This 140 µl sample was applied onto two Bio-Sil TSK-250 columns (7.5×300 mm each, Bio-Rad) attached in tandem. The elution was performed isocratically with a mobile phase of 50% acetonitrile/H₂O with 0.1% TFA. The flow rate was 0.4 ml/min; 0.4 ml fractions were collected and aliquots were assayed for GIA. The chromatographic profiles of fractions 36, 37 and 38 are shown in FIG. 10A, 10B and 10C, respectively.

Figure 10A:
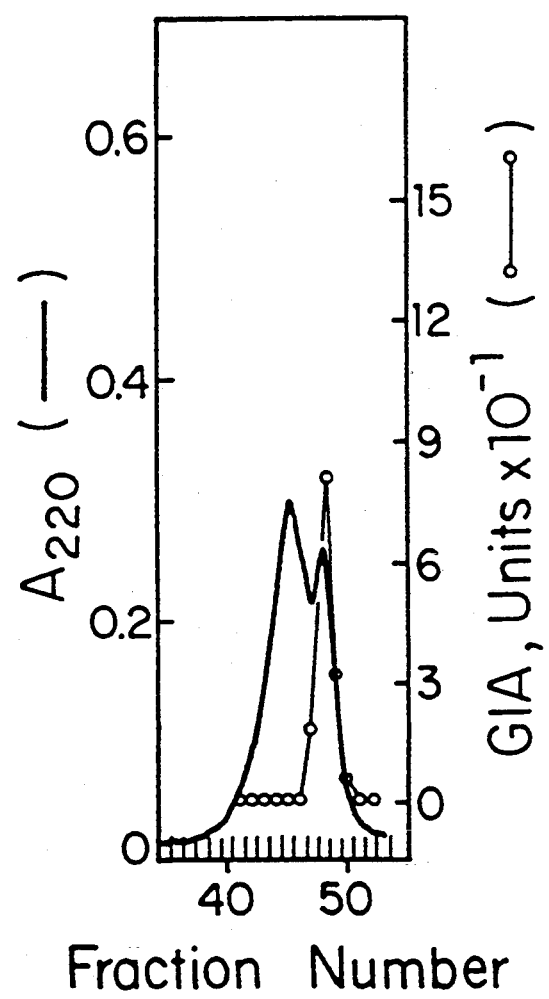
Figure 10B:
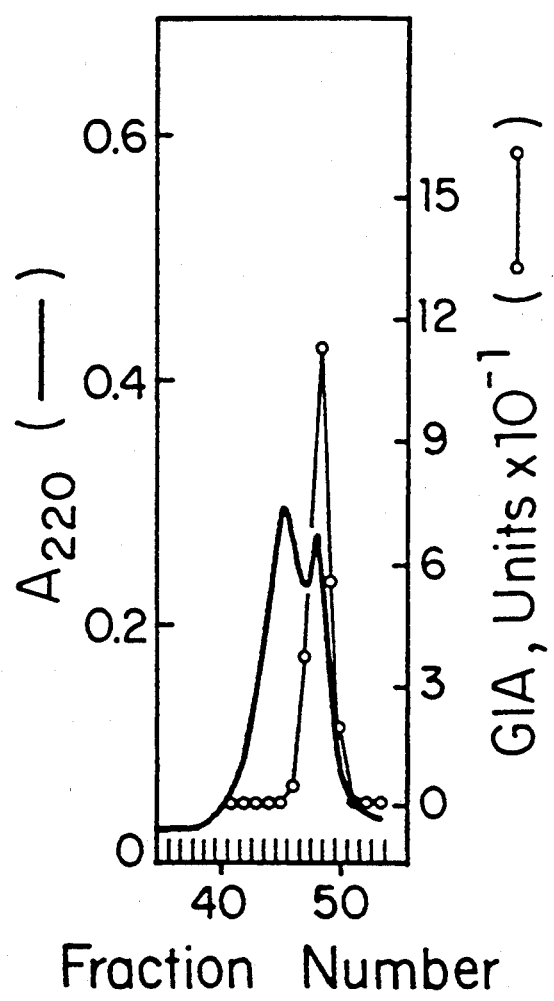
Figure 10C:
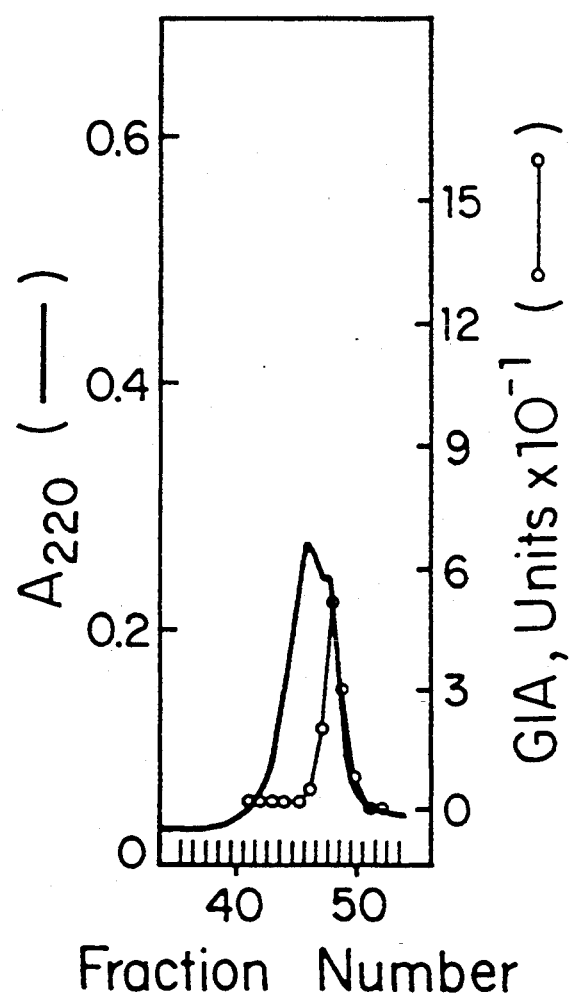
Figure 10D:
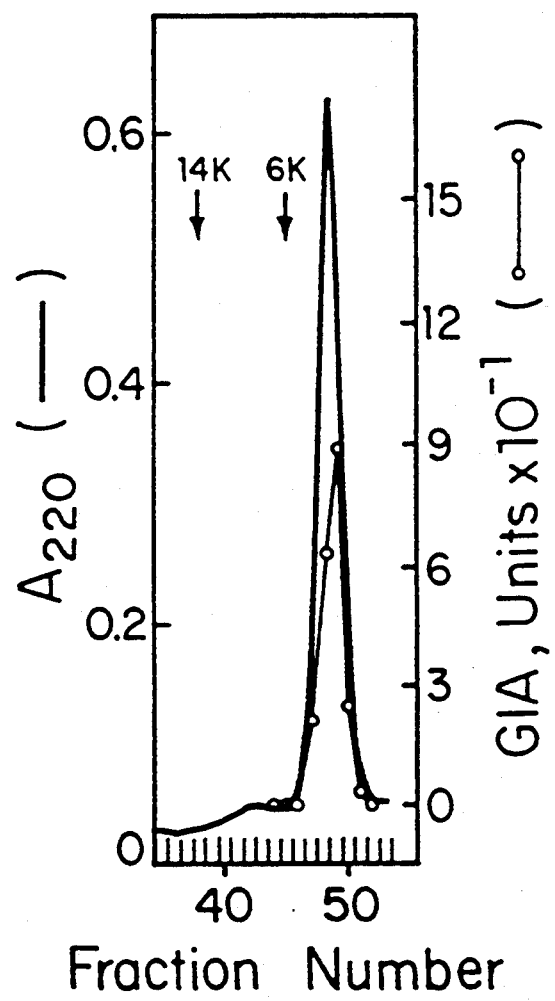

Fractions 48 and 49 from FIG. 10A–C were pooled and concentrated to about 70 µl and then subjected to gel permeation chromatography as described above. The rechromatographic profile is presented in FIG. 10D.

6.2. Bioassays

6.2.1. Cell Growth Inhibitory Activity Using $^{125}$I-Deoxyuridine Incorporation into DNA The cell growth inhibitory activity (GIA) assays were performed in flat-bottom 96 well plates (Falcon 3072). Human epidermoid carcinoma of vulva cells (A431) were used as test cells for GIA. 3.5×10³ cells in 50 µl of test medium (DMEM supplemented with 5% heat inactivated fetal bovine serum (FBS), penicillin/-streptomycin (PS) and glutamine) were placed in all wells except peripheral wells. The peripheral wells received 50 µl PBS. Three hours later, 50 µl of test sample in test medium was added to each well, while control wells received only 50 µl of test medium. Three wells were used for each concentration of test sample. Plates were incubated at 37° C. for 2–3 days. Then, 100 µl of a solution of $^{125}$I-iodo-2'-$^{125}$I-deoxyuridine ($^{125}$I-IUdR, 4Ci/mg-0.5 mCi/ml, 2 µl/ml in test medium) was added to each well and plates were incubated at 37° C. After 4–6 hours, the medium was aspirated from the wells, which were then washed once with 200 µl PBS. Then, 200 µl methanol was added to each well, plates were incubated for 10 minutes at room temperature, and the methanol was removed by aspiration. 200 µl of 1M sodium hydroxide was added to each well, the plates were incubated for 30 minutes at 37° C. Sodium hydroxide was removed with titertek plugs (Flow Labs). The plugs were transferred into 12×75 mm plastic tubes and counted in a gamma counter to quantify $^{125}$I-IUdR incorporation.

6.2.2. Cell Growth Inhibitory and Stimulatory Activity Assays Using Murine Keratinocytes Balb/MK cells were plated at 1×10⁴ cells per well in 1 ml of low calcium medium (Weissman and Aaronson, 1983, Cell 32:599–606; Carpenter and Zendegut, 1985, Anal. Biochem. 153:279–282) in 24-well Costar plates and incubated at 37° C. for 4–6 hours. Then media were removed and replaced with 1 ml of medium containing various concentrations of the test compound in triplicate. The control wells received only medium without any test material. The plates were incubated at 37° C. for 4 days, then medium was removed, wells were rinsed two times with 1 ml of phosphate-buffered saline, and the cells were detached with trypsin-EDTA and counted.

Balb/MK cells were also used as indicator cells in 96 well plates to assess the growth inhibitory activity (GIA) or growth stimulatory activity (GSA) of a test material using $^{125}$I-deoxyuridine incorporation into DNA as described in the previous section.

6.2.3. Soft Agar Colony Assay

A 0.38 ml base layer of 0.5% agar (Agar Noble; Difco Laboratories, Detroit, Mich.) in DMEM containing 10% heat inactivated FBS was added to 24 well Costar tissue culture plates. 0.38 ml of 0.3% agar containing the same medium-FBS mixture, 6–12×10³ test cells, and the test proteins at various concentrations were overlaid on the basal layer of agar. The plates were incubated at 37° C. in a humidified atmosphere of 5% CO₂ in air. Colonies were enumerated unfixed and unstained, and the number of colonies was scored between days 7 and 10. Colonies were defined as a cluster of at least eight cells.

6.3. Primary Structure Determinations

6.3.1. Reduction and S-Pyridylethylation

Protein (10–20 µg) was dried in a 1.5 ml microfuge polypropylene tube, suspended in 100 µl of 3M urea in 0.05M Tris-HCl, pH 7.5. Then, 4 µl of 2-mercaptoethanol was added to the mixture, the contents were mixed, flushed with nitrogen, and incubated at 25° C. After 2.5 hours, 4.5 µl of freshly distilled 4-vinylpyridine was added to the mixture, the tube was again flushed with nitrogen and incubated for 2 hours at 25° C. The reaction mixture was acidified to pH 2.0 with 10% TFA. S-pyridylethylated protein was purified by reversed phase HPLC using a Partisil 5 ODS-3 column (4.6×100 mm, Whatman). The concentration of acetonitrile was increased linearly (1%/min) during 55 minutes at a flow rate of 1 ml/min. The primary solvent was 0.1% TFA/H₂O. S-pyridylethylated-epithelin 1 (SPE-Epithelin 1) and SPE-Epithelin 2 eluted at about 25% and 23% of acetonitrile, respectively, approximately 2–3% higher acetonitrile concentrations than the untreated epithelins.

6.3.2. Enzymatic Cleavage of SPE-Epithelin 1 and SPE-Epithelin 2

Cleavage with endopeptidase Lys-C and TPCK-trypsin was performed in 60 μl of 0.1M Tris-acetic acid buffer, pH 8.0 at 25° C. for 16 hours. The enzyme/substrate ratio was 1 to 5 (w/w). Endopeptidase-Arg and *S. aureus* V8 protease digestions were done in 80 μl of 0.05M Tris-HCl, pH 8.0, 0.1M ammonium-bicarbonate at 37° C. for 16 hours. The enzyme/substrate ratio was again 1 to 5.

6.3.3. Peptide Isolation

Peptides were separated on a reversed phase HPLC C18 column (4.6×100 mm, Whatman) attached to a HPLC system (Waters). Acidified sample (pH 2.0) was applied onto a column equilibriated with 0.1% TFA (primary solvent) at a flow rate of 1 min/ml and the column was further washed with about 15 ml of 0.1% TFA. Linear gradients were used between the primary solvent and the secondary solvent (acetonitrile with 0.1% TFA). The gradient conditions were 0 to 50% in 125 minutes at a flow rate of 0.5 ml/min.

6.3.4. Amino Acid Analysis

Dried samples were hydrolyzed with constant boiling HCl (5.7M, Pierce) containing 1% (v/v) phenol under reduced pressure in a Teflon-sealed glass hydrolysis bulb (Pierce) at 105° C. for 16 hr. The hydrolysates were dried in a Speed Vac concentrator (Savant Instruments) and derivitized with phenylisothiocyanate for 20 minutes at room temperature. Phenylthiocarbamyl amino acid derivatives were analyzed by reversed phase HPLC on a Octadecyl column (4.5×250 mm, IBM). The linear gradient was performed between primary solvent 0.15M sodium acetate pH 6.4, 0.05% triethylamine titrated to pH 6.4 with acetic acid and the secondary solent 60% acetonitrile at a flow rate of 1 ml/min at 38° C.

6.3.5. Amino Acid Sequence Determination

Peptide sequences were determined with an Applied Biosystem model 475 gas phase sequencer as described (Hewick et al., 1981, J. Biol. Chem. 256:7990–7997). Three precycles of Edman degradation were performed prior to sample application for each run. 25% TFA was used to convert the Triazoline derivatives to phenylthiohydantoin amino acids. Identification of phenylthiohydantoin amino acids was carried out, on-line, on a Model 120A PTH analyzer (Applied Biosystem) as described (Hunkapiller and Hood, 1983, Science 219:650–659).

6.3.6. Tricine-sodium Dodecyl Sulfate-polyacrylamide Gel Electrophoresis

Proteins were analyzed on tricine/sodium dodecyl sulfate/polyacrylamide slab gels (normal or mini Bio-Rad system) by the method of Schager and Gebhard, 1987, Biochem. 166:368–379. Proteins were detected by silver staining (Wray et al., 1981, Anal. Biochem. 118:197–203).

6.4. Characteristics of the Epithelins 1 and 2
6.4.1. Physical and Chemical Properties Epithelin 1 and epithelin 2 are resistant to treatment with 1M acetic acid, 1M ammonium hydroxide, 6M urea, 0.01M sodium metaperiodate, to heating at 56° C. for 30 minutes, and to treatment with various glycosidases or lipases. However, epithelin activity was sensitive to reduction, to reduction and 4-vinylpyridine treatment, and to digestion with proteinases such as trypsin, endoproteinase Lys-C, and endoproteinase Glu-C (V8). These results suggest that these factors are proteins containing cysteines in disulfide linkage(s) that are essential for biological activity. These proteins do not contain oligosaccharides and/or lipid moieties that are obligatory for biological activities.

6.4.2. Purification of Epithelin 1 and Epithelin 2 and Certain Physical Properties Summaries of the purification of epithelin 1 and epithelin 2 are presented in Table I and Table II, respectively. Both factors were purified to apparent homogeneity by a similar six-step protocol. The early step fractions contain a multiple of growth inhibitory activities on A431 cells. Epithelins 1 and 2 constitute only a very minor fraction of total GIA in early fractions, making it very difficult to quantitate their specific activities at early stages of purification. The specific activity of purified epithelin 1 was about $2.1 \times 10^4$ units/mg protein, whereas purified epithelin 2 had a much lower specific activity of $3.8 \times 10^3$ units/mg protein

TABLE II

Summary of Purification of Epithelin 1 (GIA)

| Fraction | Protein μg | GIA Units[1] | Specific Activity Units/mg | Yield (%) |
|---|---|---|---|---|
| Crude | 4,550,000 | 1,283,100[2] | 282 | — |
| Prep TSK-250 | 473,000 | 112,200[2] | 237 | — |
| Prep. ODS (b) | 17,600 | 14,100 | 801 | 100 |
| Semi Prep. C18 | | | | |
| 1b | 1,510 | 2,080 | 1,377 | 14.8 |
| 2b | 3,460 | 5,460 | 1,578 | 38.7 |
| Anal. Cyano | | | | |
| 1b | 60 | 713 | 11,889 | 3.4 |
| 2b | 73 | 1,190 | 16,301 | 8.4 |
| Anal. Tsk-250 | | | | |
| 1b | 41 | 845 | 20,609 | 6.0 |
| 2b | 62 | 1,305 | 21,048 | 9.3 |

[1] One unit of GIA is the amount of factor required to inhibit $^{125}$I-labeled deoxyuridine incorporation into A431 cells by 50%.
[2] Other growth inhibitory activities are present in these fractions. These values include all activites.

TABLE III

Summary of Purification of Epithelin 2 (GIA)

| Fraction | Protein μg | GIA Units[1] | Specific Activity Units/mg | Yield % |
|---|---|---|---|---|
| Crude | 4,550,000 | 1,283,100[2] | 282 | — |
| Prep TSK-250 | 473,000 | 112,200[2] | 237 | — |
| Prep. ODS (b) | 24,500 | 9,567 | 432 | 100 |
| Semi Prep. C18 | 4,760 | 1,190 | 250 | 12.4 |
| Anal. Cyano | 169 | 460 | 2,741 | 4.8 |
| Anal TSK-250 | 37 | 141 | 3,810 | 1.5 |

[1] One unit of GIA is the amount of factor required to inhibit $^{125}$I-labeled deoxyuridine incorporation into A431 cells by 50%.
[2] Other growth inhibitory activities are present in these fractions. These values include all activites.

The molecular weight of epithelin 1 and epithelin 2, as determined by gel permeation chromatography on TSK-250 columns, was ~4,500 and ~3,700, respectively (FIGS. 6, 7 and 10). SPE-epithelin 1 or 2 exhibited a molecular weight of ~13,000 by similar gel permeation chromatography.

FIG. 11 shows an analysis of epithelin 1 and epithelin 2 in an 18% polyacrylamide gel under reducing conditions. Epithelin 1 and epithelin 2 migrated in the gel as single bands with median relative molecular weights of about 5,500 and 6,000, respectively. Similar results were obtained when proteins were electrophoresed under nonreducing conditions. Thus, epithelins are single chain, low molecular weight proteins.

6.4.3. Chemical Structure of Epithelin 1 and Epithelin 2

The amino acid sequences of epithelin 1 and epithelin 2 were deduced from microsequence analysis of S-pyridylethylated proteins, and fragments generated by endoproteinase Lys-C, Staphylococcal aureus V8 and TPCK trypsin. The amino acid sequences of epithelin 1 and epithelin 2 are presented in FIG. 12.

The protein sequences of epithelin 1 and epithelin 2 were compared with all proteins in the National Biomedical Research Foundation data base (release 22), Genetic Sequence Data Bank (Bolt Beranek and Newman, Los Alamos National Laboratory; release 61) and the European Molecular Biology Laboratory data base (release 20). These computer aided searches revealed that both proteins are novel and do not share any significant homology to any protein in the three data bases.

Epithelin 1 and epithelin 2 are single chain polypeptides of 56 and 57 amino acid residues, respectively, having calculated molecular weights of 6060 and 6094, respectively. Epithelin 1 and epithelin 2 share 47% homology at the amino acid level. Both proteins contain 12 cysteine residues with four double cysteine residues. Thus about 21% of amino acid residues in both proteins are cysteines. Moreover, the spacing of single cysteine residues and double cysteine residues in epithelin 1 and epithelin 2 is identical. Although the number or position of intrachain disulfide bonds in these proteins is not presently known, a similar or identical pattern is expected. Both proteins also contain about 13% hydroxy amino acids (serine and threonine together). The amino acid alignment of epithelin 1 and epithelin 2 is shown in FIG. 12. In addition the conservation of cysteine residues, 15 other residues are conserved between epithelin 1 and epithelin 2.

The hydropathy profiles of epithelins 1 and 2 are presented in FIG. 13. The hydropathy profile of epithelin 1 exhibits some similarity to that of epithelin 2, although epithelin 2 appears to be more hydrophilic than epithelin 1.

6.4.4. Biological Properties of Epithelin 1 and Epithelin 2

The inhibition of $^{125}$I-deoxyuridine incorporation into DNA of human epidermoid carcinoma A431 cells by different concentrations of purified epithelin 1 and epithelin 2 is given in FIG. 14. A 50% inhibition of DNA synthesis was seen at 12.8 ng/well of epithelin 1 and 450 ng/well of epithelin 2. Thus, a 50% inhibition occurred at approximately 21 nM concentration of epithelin 1 and approximately 0.75 µm concentration of epithelin 2. Epithelin 1 is therefore about 36 times more potent than epithelin 2 in this assay.

The effect of epithelin on the incorporation of $^{125}$I-deoxyuridine into DNA of various tumor and non-tumor human cell lines, as well as several non-human cell lines, was investigated. Epithelin 1 (20 ng/ml, maximum dose tested) slighly inhibited the growth of human colon carcinoma cell line HCT 116, while epithelin 2 (270 ng/ml, maximum dose tested) did not show any effect on this cell line. Both proteins significantly inhibited the $^{125}$I-deoxyuridine incorporation into DNA of mink lung CCL 64 cells and monkey kidney COS1 cells. Neither protein exhibited any significant effect on human fibroblasts and several other human tumor cells at the maximum dose tested (20 ng/ml for epithelin 1 and 270 ng/ml for epithelin 2).

Figure 15B:
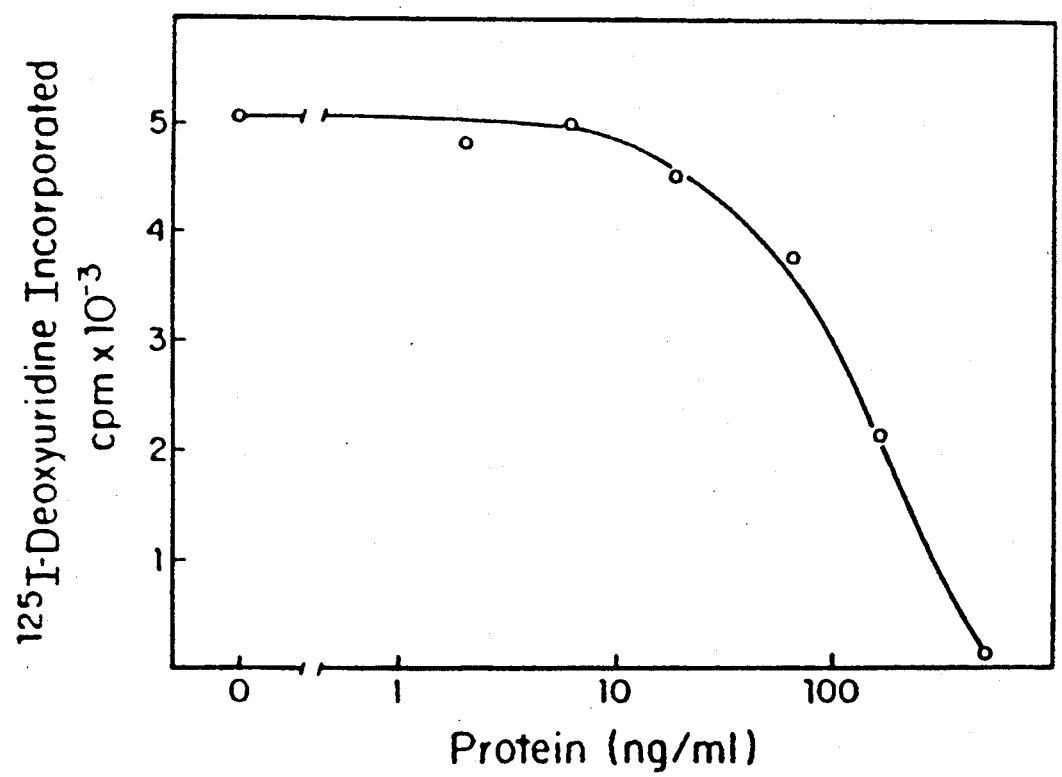

The effects of various concentrations of epithelin 1 and epithelin 2 on the incorporation of $^{125}$I-deoxyuridine into DNA of murine keratinocytes (Balb/MK cells) was investigated. Data are presented in FIG. 15A. Epithelin 1 stimulated the $^{125}$I-deoxyuridine incorporation in a dose-dependent manner, while epithelin 2 did not show any significant effect. However, epithelin 2 inhibited epithelin 1 elicited incorporation of $^{125}$I-deoxyuridine incorporation to Balb/MK cells (FIG. 15B). In this regard, a 50% inhibition was observed at ~21 nM epithelin 2. Thus, epithelin 2 antagonizes the effect of epithelin 1 in this system.

The continued growth of a murine keratinocyte cell line, Balb/MK, is dependent on EGF, TGFα or amphiregulin (AR). Balb/MK cells did not proliferate in the absence of EGF or epithelin 1 (FIG. 16A), whereas epithelin 2 did not exhibit any significant effect on the growth of these cells. However, epithelin 2 inhibited the epithelin 1-induced growth of Balb/MK cells in a dose-dependent manner (FIG. 16B); a 50% inhibition was observed at ~7 nM epithelin 2. EGF or TGFα induces anchorage-independent growth of rat kidney cells NRK-SA6 in the presence of TFGβ (Roberts et al., 1981, Proc. Natl. Acad. Sci. U.S.A. 78:5339–5344). Like EGF, epithelin 1 induced the anchorage-independent growth of NRK cells in a dose-dependent manner (FIG. 17), while epithelin 2 did not. Epithelin 2 (at a concentration of ~85 nM) inhibited about 50% of the epithelin 1-induced colony formation in soft agar. Furthermore, epithelin 1, but not epithelin 2, exhibited mitogenic activity on NRK cells in monolayer.

Neither epithelin 1 nor epithelin 2 significantly affected the binding of $^{125}$I-EGF to its receptors, suggesting that the epithelins do not mediate their biological effects through EGF receptors.

7. Example: cDNA Cloning of the Epithelin Precursor and Transient Expression of Precursor and Mature Forms

7.1. PCR cDNA Cloning

Two pools of degenerate oligonucleotides were synthesized based on the peptide sequences KTQCPDD and HCCPQDT from epithelin 2 (the pools contained 256 and 128 degenerate oligonucleotides in the sense and antisense orientation, respectively). These oligonucletides were used as primers in a 40 cycle PCR amplification with a single stranded cDNA template derived from rat kidney RNA primed with XSCT17, an oligonucleotide containing a $T_{17}$ track on its 3'-end (Plowman et al, 1990, Proc. Natl. Acad. Sci. U.S.A. 87:4905–08). An oligonucleotide probe, based on the epithelin 2 sequence KYGCCPMP (256 fold degenerate 23-mer), was labeled with [γ-$^{32}$P]ATP and used to screen the PCR products.

Hybridization of this probe to a Southern blot of the PCR products revealed two major bands of 120 base pairs (bp) and 600 bp, and a minor band of 325 bp. These fragments were subcloned and sequenced, revealing that they all had a common 5' end encoding epithelin 2. The 325 bp fragment had an open reading frame that encoded both epithelin 1 and 2, whereas the 600 bp band extended further 3' and contained an additional copy of the cysteine-rich motif. Therefore, epithelin 1 and 2 appear to be tandemly arranged products of a single transcript. These same PCR primers were used to isolate similar fragments of the epithelin precursor from human, bovine, mouse, and chicken cDNA, demonstrating strong evolutionary conservation of the cysteine-rich motif.

The complete epithelin cDNAs were obtained from rat, mouse, and human sources by using a PCR protocol to isolate the 5' and 3' ends of messages that have a known central sequence, and by screening λgt10 libraries. In particular, a PCR strategy with exact epithelin primers oriented in the 3' and 5' directions in combination with primers that anneal to the natural poly(A) tail, or a synthetic poly(A) track added onto the 5' extended cDNA was employed (Plowman et al., 1990, Proc. Natl. Acad. Sci. U.S.A. 87:4905–08). A rat kidney cDNA library was constructed in λgt10 (Plowman et al., 1990, Mol. Cell Biol. 10:1969–81), and a full length rat epithelin cDNA was isolated by screening $2.0 \times 10^5$ recombinants with PCR generated epithelin probes. These probes were also used to obtain the mouse epithelin gene from a mouse T-cell genomic library (Stratagene, La Jolla, Calif.). Several PCR-generated clones, rat cDNA clones, and the mouse genomic clones were sequenced on both strands by using T7 polymerase with oligonucleotide primers (Tabor and Richardson 1987, Proc. Natl. Acad. Sci. U.S.A. 84:4767–71.

The composite sequence of the rat epithelin cDNA (SEQ ID NO: 1) is 2150 bp long, which closely approximates the 2.3 kilobase transcript seen by northern analysis with rat kidney mRNA. The sequence predicts a 589-residue preprotein with a 30 bp 5'-untranslated region and a 343 bp 3'-untranslated region. The first AUG is followed by an N-terminal hydrophobic signal peptide of 16 amino acids and the 573 amino acid mature epithelin precursor with a predicted $M_r$ of 61,597. The precursor has no transmembrane domain, 3 potential N-linked glycosylation sites, and 88 cysteine residues. The epithelin precursor has a highly repetitive organization (FIG. 18) containing 7 tandem copies of a 55–57 amino acid consensus motif: $VXCX_{5-6}CX_5CCX_8CCX_6CCXDX_2HCCPX_4CX_{5-6}CX_2$. Two of the repeats represent the known active molecules, epithelin 1 and 2. The predicted amino acid sequences of the mouse and human epithelin precursors contain 589 and 593 residues, respectively, and exhibit 86% (mouse) and 75% (human) sequence identity with the rat protein (FIG. 20A); (SEQ ID NOS: 6 (mouse), 4 (human) and 2 (rat)). Additional isoforms of epithelin may also exist, since one rat cDNA clone has a deletion of 234bp (FIG. 20A, amino acids 398–475), maintained the reading frame, and generated a chimeric motif. This deletion is likely the result of alternative splicing since its boundaries map precisely to the location of exon-intron junctions in the mouse epithelin gene.

Comparison of the epithelin sequence with available protein and DNA sequence databases reveals three regions with homology to known proteins. The first 41 amino acids following the signal sequence of the epithelin precursor contains 6 cysteine residues arranged in a pattern similar to the N-terminal half of the other seven cystein-rich motifs. The sequence CPDGQFCPVACC is completely conserved between human, rat and mouse epithelins, and conforms to a consensus pattern present in a family of snake toxins (Dufton, 1984, J. Mol. Evol. 20:128–34). A second region of homology exists within three of the cystein-rich motifs of rat epithelin ($CCX_2HX_2C$), and conforms to a consensus surrounding an active site of phospholipase A2 (Gomez et al., 1989, J. Eur. J. Biochem. 186:23–33). Finally, an extended homology exists between the 12 cysteine motif of epithelin and the C-terminal regulatory domain of a tomato thiol protease (FIG. 20D). This noncatalytic domain has been hypothesized to regulate the protease activity by binding to heavy metals. The alternating cysteine and histidine residues in the epithelin precursor is reminiscent of metal-binding domains of a variety of proteins, although the epithelin motif does not conform to that of any known metal-binding consensus. Northern analysis demonstrates that the 2.3 kilobase epithelin transcript is ubiquitously expressed, and is predominant in the adult kidney, placenta, heart, duodenum, colon, and cerebral cortex. In addition, it is present in a wide variety of epithelial tumor cell lines. Southern analysis indicates that the epithelin precursor is encoded by a single copy gene. These results suggest a post-transcriptional mechanism for the generation of active molecules from the epithelin precursor.

7.2. Expression in COS Cells

The biochemical properties of rat epithelin was determined by inserting its complete coding sequence into an expression vector under the control of the cytomegalovirus immediate-early promoter (Seed and Aruffo, 1987, Proc. Natl. Acad. Sci. U.S.A. 84:3365–69). Specifically, a 1.6 kb fragment containing the complete rat epithelin coding sequence was inserted into a cDM8 based expression vector, generating the expression vector crEPN1.6. A similar construct, crEPN1.4, was prepared by insertion of a 1.35 kb fragment from an epithelin cDNA that has a single exon deletion, thereby eliminating amino acids 398–475. The secretion plasmids, cβrEPN1 and cβrEPN2, were constructed by ligating a synthetic simian TGF-β1 signal sequence (SEQ ID NO: 11) contained on the oligonucleotides

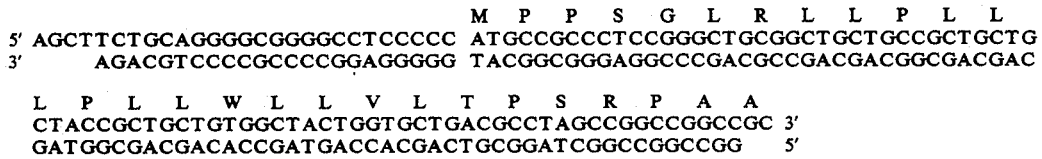

sequences and PCR generated SacII-XbaI fragments containing the coding sequence of epithelin 1 and 2 into the cDM8SII plasmid digested with HindIII and XbaI. cDM8SII is a modified cDM8 vector, where the unique SacII site has been eliminated with Klenow. The new SacII site places a final glycine of the signal peptide in frame with the epithelin coding sequence. The expression plasmids were grown in competent MC1061/P3 bacteria, and introduced into COS-1 cells using the DEAE-dextran method (Seed and Aruffo, 1987, Proc. Natl. Acad. Sci. U.S.A. 84:3365–69). Forty-eight hours after transfection, the cells were washed with phosphate buffered saline, and labeled for 16 hours in serum free MEM (4 ml per 100 mm plate) supplemented with 250 μCi/ml $^{35}$S-cysteine (1100 Ci/mmole, New England Nuclear). Labeled supernatants were dialyzed against 0.1N acetic acid, dried, and 1 ml equivalents run on 10% or 15% SDS-polyacrylamide gels.

The transiently expressed protein was readily detected by SDS-PAGE analysis of $^{35}$S-cysteine labeled supernatants. The recombinant protein had a molecular mass of about 75K, slightly more than the predicted 62K, possibly due to glycosylation (FIG. 21A, lane 1). A similar construct encoding an epithelin isoform, but lacking an exon in the C-terminal region, migrated with average $M_r$ of 68K, commensurate with the deletion of 78 amino acids. There was no evidence of the precursor being processed into smaller forms. To express the mature recombinant epithelin 1 and 2 proteins, their coding regions were placed into an expression vector behind a synthetic signal peptide sequence (cβrEPN1 and cβrEPN2, respectively), which resulted in secretion of the 6K proteins from COS cells (FIG. 21B). The cells transfected with these constructs were growth inhibited and exhibited an altered morphology with many cells showing a signet ring appearance, compared with the intact monolayer seen on a mock transfection. Supernatant from the cβrEPN1 transfection was partially purified on a Bio-Sil TSK-250 column (Shoyab et al., 1990, 87:4905–09) and fractions were assayed for growth inhibitory activity (GIA) on A431 cells. These cells secreted active epithelin 1 (approximately 25 GIA units/100 mm plate) whereas the supernatant from mock transfected cells had no detectable activity (one GIA unit corresponds to the amount of material required for 50% inhibition of cell growth).

Epithelin 1 has an inhibitory effect on A431 cells and it acts as mitogen on several normal epithelial cell lines (See Section 6., supra). In addition, epithelin 1 can induce anchorage-independent growth of rat kidney fibroblasts in the presence of transforming growth factor β (FIG. 17). In contrast, epithelin 2 has no effect on the growth of rodent keratinocytes of fibroblasts and it opposed the mitogenic effects of epithelin 1 (in a dose dependent manner) in both of these systems (FIG. 17). The unprocessed epithelin precursor had no activity in any of these assays. Perhaps the intact precursor serves an entirely different role than the processed forms, such as chelating metal ions, or regulation of proteases and phospholipases.

What is claimed is:

1. Isolated human epithelin 1 having the amino acid sequence as depicted in SEQ ID NO: 4 from about amino acid residue numbers 282 to 337.

2. Isolated rat epithelin 1 having the amino acid sequence as depicted in SEQ ID NO: 2 from amino acid residue numbers 280 to 335.

3. Isolated mouse epithelin 1 having the amino acid sequence as depicted in SEQ ID NO: 6 from amino acid residue numbers 280–335.

* * * * *